United States Patent
Zhang

(10) Patent No.: US 12,036,262 B2
(45) Date of Patent: Jul. 16, 2024

(54) EDIBLE PLANT-DERIVED NANOPARTICLES FOR REGULATION OF GUT MICROBIOTA

(71) Applicant: University of Louisville Research Foundation, Inc., Louisville, KY (US)

(72) Inventor: Huang-Ge Zhang, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 490 days.

(21) Appl. No.: 16/766,055

(22) PCT Filed: Nov. 21, 2018

(86) PCT No.: PCT/US2018/062349
§ 371 (c)(1),
(2) Date: May 21, 2020

(87) PCT Pub. No.: WO2019/104242
PCT Pub. Date: May 31, 2019

(65) Prior Publication Data
US 2021/0085744 A1    Mar. 25, 2021

Related U.S. Application Data

(60) Provisional application No. 62/686,421, filed on Jun. 18, 2018, provisional application No. 62/589,901, filed on Nov. 22, 2017.

(51) Int. Cl.
| | |
|---|---|
| *C07H 21/04* | (2006.01) |
| *A61K 9/127* | (2006.01) |
| *A61K 9/14* | (2006.01) |
| *A61K 9/51* | (2006.01) |
| *A61K 36/9068* | (2006.01) |
| *C12N 15/113* | (2010.01) |
| *B82Y 5/00* | (2011.01) |
| *B82Y 40/00* | (2011.01) |

(52) U.S. Cl.
CPC ........ *A61K 36/9068* (2013.01); *A61K 9/1271* (2013.01); *A61K 9/148* (2013.01); *A61K 9/5176* (2013.01); *C12N 15/113* (2013.01); *B82Y 5/00* (2013.01); *B82Y 40/00* (2013.01); *C12N 2310/141* (2013.01); *C12N 2330/10* (2013.01); *C12N 2501/2322* (2013.01)

(58) Field of Classification Search
CPC ........................ C12N 15/113; C12N 2310/141
See application file for complete search history.

(56) References Cited

U.S. PATENT DOCUMENTS

| | | |
|---|---|---|
| 7,897,356 B2 | 3/2011 | Klass et al. |
| 9,717,733 B2 | 8/2017 | Zhang |
| 9,752,148 B2 | 9/2017 | Zhang |
| 10,590,171 B2 | 3/2020 | Silvas et al. |
| 2010/0048888 A1 | 2/2010 | Chen et al. |
| 2010/0209415 A1 | 8/2010 | Smith et al. |
| 2010/0298151 A1 | 11/2010 | Taylor et al. |
| 2011/0010817 A1 | 1/2011 | Théberge et al. |
| 2012/0183575 A1 | 7/2012 | Gabrielsson |
| 2012/0315324 A1 | 12/2012 | Zhang |
| 2013/0115241 A1 | 5/2013 | Gho |
| 2013/0129790 A1 | 5/2013 | Alexis et al. |
| 2014/0308212 A1 | 10/2014 | Zhang |
| 2016/0354313 A1 | 12/2016 | De Beer et al. |
| 2017/0035700 A1 | 2/2017 | Zhang |
| 2018/0140654 A1 | 5/2018 | Zhang |
| 2018/0362974 A1 | 12/2018 | Zhang |
| 2019/0382539 A1 | 12/2019 | Zhang |
| 2020/0046788 A1 | 2/2020 | Zhang |
| 2020/0063208 A1 | 2/2020 | Zhang |
| 2020/0188311 A1 | 6/2020 | Zhang |
| 2020/0206297 A1 | 7/2020 | Zhang |
| 2021/0236612 A1 | 8/2021 | Zhang |
| 2022/0142937 A1 | 5/2022 | Zhang |
| 2023/0149316 A1 | 5/2023 | Zhang |

FOREIGN PATENT DOCUMENTS

| | | |
|---|---|---|
| AU | 2008207735 | 7/2008 |
| CN | 106924730 | 7/2017 |
| EP | 3 129 010 | 12/2019 |
| KR | 10-2013-0087174 | 8/2013 |
| WO | WO 2004/019916 | 3/2004 |
| WO | WO 2008/092153 | 7/2008 |

(Continued)

OTHER PUBLICATIONS

Liu et al. (Cell Host & Microbe, 2016, 19, 32-43).*
Zhang et al. (Nanomedicine (Lond.), 2016, 11, 23, 3035-3037).*
Baier et al. (The Journal of Nutrition, 144, 10, 2014, pp. 1495-1500).*
Ionescu et al. (Frontiers in Cardiovascular Medicine, 2022, 9, Article 856901, 1-14).*
Plotnikova et al., Frontiers in Genetics, 2019, 10, 933, 1-11.*
Alvarez-Erviti et al. Delivery of siRNA to the mouse brain by systemic injection of targeted exosomes. Nat Biotechnol 29, 341-345 (2011).
Antonyak & Cerione. Microvesicles as mediators of intercellular communication in cancer. Methods in molecular biology. 2014; 1165:147-173.
Arora et al. Synthesis, characterization and evaluation of poly (D,L-lactide-co-glycolide)-based nanoformulation of miRNA-150: potential implications for pancreatic cancer therapy. Int J Nanomedicine, Jun. 18, 2014, vol. 9, pp. 2933-2942.

(Continued)

*Primary Examiner* — Amy Rose Hudson
(74) *Attorney, Agent, or Firm* — Meunier Carlin & Curfman LLC

(57) ABSTRACT

Provided are methods for modulating gut microbiota in subjects. In some embodiments, the methods include administering to a subject an effective amount of a composition that includes a first edible plant-derived nanoparticle encapsulating an effective amount of RNA. Also provided are methods for preventing and/or treating gut dysbiosis, methods for modulating bacterial growth, methods for modulating inflammatory cytokines, methods for reducing migration of bacterial from the gut to gut-associated bloodstream, and compositions for use in the presently disclosed methods, including pharmaceutical compositions.

5 Claims, 35 Drawing Sheets

Specification includes a Sequence Listing.

(56) References Cited

FOREIGN PATENT DOCUMENTS

| WO | WO 2009/065561 | 5/2009 |
|---|---|---|
| WO | WO 2009/147519 | 12/2009 |
| WO | WO 2010/096597 | 8/2010 |
| WO | WO 2011/097480 | 8/2011 |
| WO | WO 2013/048734 | 4/2013 |
| WO | WO 2013/070324 | 5/2013 |
| WO | WO 2014/028487 | 2/2014 |
| WO | WO 2015/058148 | 4/2015 |
| WO | WO 2015/157652 A1 | 10/2015 |
| WO | WO 2017/004526 | 1/2017 |
| WO | WO 2017/083068 | 5/2017 |
| WO | WO 2017/176792 | 10/2017 |
| WO | WO 2018/039119 | 3/2018 |
| WO | WO 2018/071806 | 4/2018 |
| WO | WO 2018/098247 | 5/2018 |
| WO | WO-2018/107061 A1 | 6/2018 |
| WO | WO 2019/104242 | 5/2019 |
| WO | WO 2019/173487 | 9/2019 |
| WO | WO-2019/195179 A1 | 10/2019 |
| WO | WO 2019/210189 | 10/2019 |
| WO | WO-2020/041783 A1 | 2/2020 |
| WO | WO-2020/180801 A1 | 9/2020 |
| WO | WO-2021/237215 A1 | 11/2021 |

OTHER PUBLICATIONS

Blaskovich. Discovery of JSI-124, a selective janus kinase signal transducer and activator of transcription 3 signaling pathway inhibitor with potent antitumor activity against human and murine cancer cells in mice, Can Res, 2003, 63, 1270-1279.
Bove et al. The Blossoming of RNA biology: Novel Insights from Plant System, RNA (2006), 12:2035-2046.
Cho (2012) "MicroRNAs as therapeutic targets and their potential applications in cancer therapy," Expert Opinion on Therapeutic Targets, 16(8), pp. 747-759.
Decision to Grant corresponding to European Patent No. 15 776 590.0-1112 dated Nov. 7, 2019.
Devkota, S. et al. (2012) "Dietary-fat-induced taurocholic acid production promotes pathobiont expansion and colitis in IL-10$^{-/-}$ mice," Nature 487:104-108.
European Patent Office, Extended European Search Report, EP Application No. 17875026.1, 20 pgs., dated Jul. 2, 2020.
Examination Report for AU Patent Application No. 2016288643, 5 pages, dated Aug. 18, 2020.
Examination Report for AU Patent Application No. 2016288643 dated Jul. 1, 2021.
Geng et al., MicroRNA-192 suppresses liver metastasis of colon cancer, Oncogene, vol. 33, pp. 5332-5340. (Year: 2014).
Greaney et al. (2016) "Sulforaphane Inhibits Multiple Inflammasomes through an Nrf2-Independent Mechanism," Journal of Leukocyte Biology, vol. 99, pp. 189-199.
He et al. (2014) "MiR-23a Functions as a Tumor Suppressor in Osteosarcoma," Cell Physiol Biochem, vol. 34, pp. 1485-1496.
International Search Report and Written Opinion issued in corresponding Application No. PCT/US15/25337, dated Jul. 1, 2015.
International Search Report and Written Opinion issued in corresponding Application No. PCT/US16/040710, dated Sep. 23, 2016.
International Preliminary Report on Patentability corresponding to International Application No. PCT/US12/056298, dated May 22, 2014.
International Search Report and Written Opinion issued in corresponding Application No. PCT/US2011/023747, completed Mar. 22, 2011.
International Preliminary Report on Patentability corresponding to International Patent Application No. PCT/US2011/023747 dated Aug. 7, 2012.
International Search Report and Written Opinion issued in corresponding International Application No. PCT/US19/29377, dated Sep. 9, 2019.
International Search Report and Written Opinion issued in corresponding Application No. PCT/US19/020971, dated May 23, 2019.
International Search Report and Written Opinion issued in corresponding Application No. PCT/US18/062349, dated Apr. 29, 2019.
International Preliminary Report on Patentability corresponding to International Application No. PCT/US18/062349, dated May 26, 2020.
International Preliminary Report on Patentability corresponding to International Application No. PCT/US17/056570, dated Apr. 25, 2019.
International Preliminary Report on Patentability corresponding to International Application No. PCT/US17/062970, dated Jun. 6, 2019.
Liu et al. (2016) "The Host Shapes the Gut Microbiota via Fecal MicroRNA," Cell Host & Microbe, vol. 19, pp. 32-43.
Long et al. (2009) "Let-7a MicroRNA Functions as a Potential Tumor Suppressor in Human Laryngeal Cancer," Oncology Reports, vol. 22, pp. 1189-1195.
Notice of Allowance corresponding to U.S. Appl. No. 16/523,761 dated Jun. 11, 2020.
Notice of Allowance corresponding to U.S. Appl. No. 15/948,218 dated Apr. 27, 2020.
Office Action corresponding with Chinese Patent Application No. 201680049762.8 dated Jul. 1, 2021.
Office Action corresponding with European Patent Application No. 15 776 590.0-1112 dated Nov. 6, 2018.
Office Action corresponding with European Patent Application No. 16818891.0 dated Jan. 9, 2019.
Office Action corresponding with European Patent Application No. 16818891.0 dated Feb. 1, 2021.
Office Action corresponding with European Patent Application No. 17875026.1 dated Apr. 9, 2021.
Office Action corresponding to U.S. Appl. No. 15/821,408 dated Nov. 12, 2019.
Office action (Restriction Requirement) corresponding to U.S. Appl. No. 13/576,907 dated Mar. 27, 2013.
Office Action corresponding to U.S. Appl. No. 13/576,907 dated Jun. 18, 2013.
Office action (Restriction Requirement) corresponding to U.S. Appl. No. 14/107,691 dated Feb. 13, 2014.
Office Action corresponding to U.S. Appl. No. 14/107,691 dated Jun. 19, 2014.
Office Action corresponding to U.S. Appl. No. 14/107,691 dated Feb. 6, 2015.
Office Action corresponding to U.S. Appl. No. 14/107,691 dated Oct. 6, 2015.
Office Action corresponding to U.S. Appl. No. 14/107,691 dated Jun. 28, 2016.
Office Action corresponding to U.S. Appl. No. 14/107,691 dated Mar. 14, 2017.
Office Action corresponding to U.S. Appl. No. 14/107,691 dated Sep. 13, 2017.
Office Action (Restriction Requirement) corresponding to U.S. Appl. No. 15/917,151 dated Apr. 20, 2018.
Office Action corresponding to U.S. Appl. No. 15/917,151 dated Sep. 21, 2018.
Office Action corresponding to U.S. Appl. No. 15/740,591 dated Apr. 24, 2019.
Office Action corresponding to U.S. Appl. No. 15/740,591 dated Aug. 13, 2019.
Office Action corresponding to U.S. Appl. No. 15/740,591 dated Mar. 9, 2020.
Office Action corresponding to U.S. Appl. No. 15/740,591 dated May 26, 2021.
Office Action corresponding to U.S. Appl. No. 16/340,457 dated Mar. 22, 2021.
Office Action corresponding to U.S. Appl. No. 16/359,618 dated Aug. 10, 2020.
Office Action corresponding to U.S. Appl. No. 16/359,618 dated Apr. 26, 2021.
Office Action corresponding to U.S. Appl. No. 16/377,800 dated Oct. 16, 2019.

(56) References Cited

OTHER PUBLICATIONS

Office Action corresponding to U.S. Appl. No. 16/377,800 dated Apr. 20, 2020.
Office Action corresponding to U.S. Appl. No. 16/377,800 dated Dec. 21, 2020.
Office Action (Restriction Requirement) corresponding to U.S. Appl. No. 16/383,085 dated Dec. 15, 2020.
Office Action (Restriction Requirement) corresponding to U.S. Appl. No. 16/462,715 dated Nov. 20, 2020.
Office Action (Restriction Requirement) corresponding to U.S. Appl. No. 16/462,715 dated Apr. 9, 2021.
Office Action (Restriction Requirement) corresponding to U.S. Appl. No. 16/523,761 dated Nov. 5, 2019.
Office Action corresponding to U.S. Appl. No. 16/523,761 dated Jan. 31, 2020.
Ogata-Kawata et al. (2014) "Circulating Exosomal MicroRNAs as Biomarkers of Colon Cancer," PLOS One, vol. 9, No. 4, pp. 1-9.
Powell, J.J., Faria, N., Thomas-Mckay, E. et al. Origin and fate of dietary nanoparticles and microparticles in the gastrointestinal tract. J Autoimmun 2010;34:J226-33.
Powell, J.J., Thoree, V., Pele, L.C. Dietary microparticles and their impact on tolerance and immune responsiveness of the gastrointestinal tract. Br J Nutr 2007;98 Suppl 1:S59-63.
Tristan-Ramos (2020) "The Tumor Suppressor MicroRNA let-7 Inhibits Human LINE-1 Retrotransposition," Nature Communications, vol. 11, No. 5712, pp. 1-14.
Wagner et al. (2013) "DSS-Induced Acute Colitis in C57BL/6 Mice is Mitigated by Sulforaphane Pre-Treatment," Journal of Nutritional Biochemistry, vol. 24, pp. 2085-2091.
Xue et al., Solid lipid-PEI hybrid nanocarrier: An integrated approach to provide extended, targeted, and safer siRNA therapy of prostate cancer in an all-in-one manner, ACS Nano, vol. 5, pp. 7034-7047. (Year: 2011).
Yanaka et al. (2007) Daily intake of sulphoraphane-rich broccoli sprouts prevents colon tumor formation in mice treated with dextran sodium sulfate and azoxymethane via stimulating nrf2-dependent antioxidant enzymes. Gastroenterology, vol. 132, No. 4 (Suppl. 2), p. A23.
Zhang et al. (2016) "Plant derived edible nanoparticles as a new therapeutic approach against diseases," Tissue Barriers, vol. 4, No. 2, pp. 1-9, specif. p. 1.
Deng et al. "Exosomes miR-126a Released 1-1 from MDSC Induced by DOX Treatment Promotes Lung Metastasis," Oncogene, 2017, vol. 36, No. 5, pp. 639-651.
Dryden (2011) "Phase I Clinical Trial Investigating the Ability of Plant Exosomes to Deliver Curcumin to Normal and Malignant Colon Tissue."
European Patent Office, Extended European Search Report, EP Application No. 19793847.5, 8 pgs., dated Apr. 8, 2022.
Examination Report for IN Patent Application No. 201817004051 dated Nov. 25, 2021.
Office Action corresponding with European Patent Application No. 16818891.0 dated Oct. 4, 2021.
Office Action (Restriction Requirement) corresponding to U.S. Appl. No. 16/816,214 dated Sep. 28, 2021.
Office Action corresponding to U.S. Appl. No. 17/050,200 dated Feb. 17, 2022.
Office Action corresponding to U.S. Appl. No. 16/359,618 dated Feb. 10, 2022.
Office Action corresponding to U.S. Appl. No. 16/377,800 dated Aug. 18, 2021.
Office Action corresponding to U.S. Appl. No. 16/383,085 dated Sep. 24, 2021.
Office Action corresponding to U.S. Appl. No. 16/383,085 dated Apr. 7, 2022.
Office Action corresponding to U.S. Appl. No. 16/383,085 dated Sep. 15, 2022.
Office Action corresponding to U.S. Appl. No. 16/462,715 dated Dec. 27, 2021.
Office Action corresponding to U.S. Appl. No. 16/462,715 dated Aug. 2, 2022.
Office Action corresponding to U.S. Appl. No. 16/816,214 dated May 13, 2022.
Teng et al. 2018 "Plant-Derived Exosomal MicroRNAs Shape the Gut Microbiota," Cell Host & Microbe, vol. 24, pp. 637-652 plus Methods Addendum, pp. e1-e8; specifically p. 637, 639, and e3.
Zhang et al. (2016) "Edible ginger-derived nanoparticles: A novel therapeutic approach for the prevention and treatment of inflammatory bowel disease and colitis-associated cancer," Biomaterials, vol. 101, pp. 321-340.
Zhang et al. (2016) "Do ginger-derived nanoparticles represent an attractive treatment strategy for inflammatory bowel disease?" website article published on Nov. 4, 2016 and/or Nanomedicine (Lond.), vol. 11(23), pp. 3035-3037.
Aftab et al. (2020) "Analysis of SARS-CoV-2 RNA-dependent RNA polymerase as a potential therapeutic drug target using a computational approach.," J Transl Med 18:275.
Arienti et al. (2019) "Regulation of Apoptotic Cell Clearance During Resolution of Inflammation,". Front Pharmacol 10:891; 12 Pages.
Examination Report for CA Patent Application No. 3,029,602 dated Aug. 26, 2022.
Examination Report for CA Patent Application No. 3,029,602 dated May 5, 2023.
Godoy et al. (2018) "Large Differences in Small RNA Composition Between Human Biofluids," Cell Rep 25:pp. 1346-1358.
International Preliminary Report corresponding to International Patent Application Serial No. PCT/US2021/033913 dated Nov. 17, 2022.
International Search Report and Written Opinion corresponding to International Patent Application Serial No. PCT/US2021/033913 dated Oct. 6, 2021.
Interview Summary corresponding to U.S. Appl. No. 16/383,085 dated Mar. 18, 2022.
Interview Summary corresponding to U.S. Appl. No. 16/383,085 dated May 19, 2022.
Interview Summary corresponding to U.S. Appl. No. 16/383,085 dated Nov. 1, 2022.
Interview Summary corresponding to U.S. Appl. No. 16/383,085 dated Mar. 3, 2023.
Lee et al. (2018) "Extracellular Vesicle: An Emerging Mediator ofIntercellular Crosstalk in Lung Inflammation and Injury.," Front Immunol vol. 9: article 92; 8 Pages.
Masvekar et al. (2019) "Quantifications of CSF Apoptotic Bodies Do Not Provide Clinical Value in Multiple Sclerosis," Front Neurol 10, 1241, doi:10.3389/fneur.2019.01241. 11 Pages.
Miura (2019) "Respiratory epithelial cells as master communicators during viral infections,". Curr Clin Mi crobi ol Rep 6: pp. 10-17.
Miyamoto et al. (2010) "Inhibitor of IkappaB kinase activity, BAY 11-7082, interferes with interferon regulatory factor 7 nuclear translocation and type I interferon production by plasmacytoid dendritic cells.," Arthritis Res Ther 12:R87.13 Pages.
Mukhamedova et al. (2019) "Exosomes containing HIV protein Nef reorganize lipid rafts potentiating inflammatory response in bystander cells.," PLoS Pathogens 15:el007907.30 Pages.
Murphy et al. (2008) Suppression of immediate-early viral gene expression by herpesviruscoded microRNAs: implications for latency. Proceedings of the National Academy of Sciences USA 105: pp. 5453-5458.
Nahand et al. (2020) "Exosomal miRNAs: novel players in viral infection.," Epigenomics 12: pp. 353-370.
Office Action corresponding to U.S. Appl. No. 16/377,800 dated Apr. 24, 2023.
Office Action corresponding to U.S. Appl. No. 16/383,085 dated Mar. 20, 2023.
Office Action corresponding to U.S. Appl. No. 16/462,715 dated Apr. 4, 2023.
Office Action corresponding with European Patent Application No. 16818891.0 dated Mar. 23, 2023.
Pastuzyn et al. (2018) "The Neuronal Gene Arc Encodes a Repurposed Retrotransposon Gag Protein that Mediates Intercellular RNA Transfer.," Cell 172: pp. 275-288.

(56) References Cited

OTHER PUBLICATIONS

Raab-Traub & Dittmer (2017) "Viral effects on the content and function of extracellular vesicles.," Nature Reviews Microbiology 15:pp. 559-572.
Robinson & Oshlack (2010) "A scaling normalization method for differential expression analysis of RNA-seq data," Genome Biology 11: 9 pages.
Sampey et al. (2016) "Exosomes from HIV-I-infected Cells Stimulate Production of Pro-inflammatory Cytokines through Trans-activating Response (TAR) RNA," The Journal ofBiological Chemistry 291:pp. 1251-1266.
Santiana et al. (2018) "Vesicle-Cloaked Virus Clusters Are Optimal Units for Interorganismal Viral Transmission.," Cell Host & Microbe 24:pp. 208-220.
Sundaram et al. (2019) "Plant-Derived Exosomal Nanoparticles Inhibit Pathogenicity of Porphyromonas gingivalis,". iScience 21 :pp. 308-327.
Teng et al. (2016) "Grapefruit-derived nanovectors deliver miR-18a for treatment of liver metastasis of colon cancer by induction of MI macrophages,". Oncotarget 7: pp. 25683-25697.
Teng et al. (2017) "MVP-mediated exosomal sorting of miR-193a promotes colon cancer progression,". Nat Commun 8:14448; 16 Pages.
Velandia-Romero et al. (2020) "Extracellular vesicles ofU937 macrophage cell line infected with DENV-2 induce activation in endothelial cells," EA.hy926. PloS One 15:e0227030.25 pages.
Xiao et al. (2018) "Identification of exosome-like nanoparticle-derived microRNAs from 11 edible fruits and vegetables.," PeerJ 6:e5186. 19 Pages.
Zhang et al. (2008) "Inhibition of the tumor necrosis factor-alpha pathway is radioprotective for the lung.," Clin Cancer Res 14: pp. 1868-1876.

\* cited by examiner

1. GELNs
2. PA 36:2
3. PA 36:4
4. PA 34:1
5. PA 34:2
6. PC 34:2
7. Grapefruit ELNs

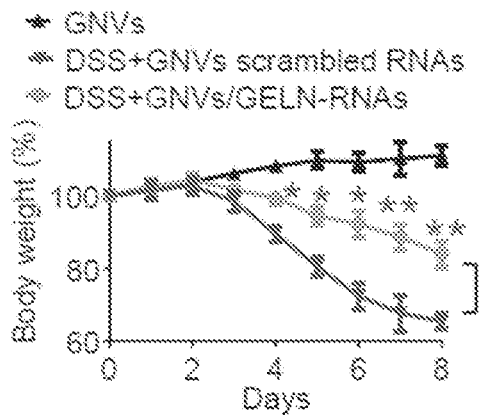 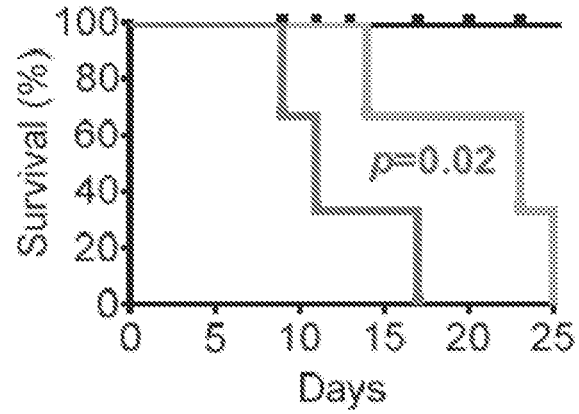
FIG. 30  FIG. 31
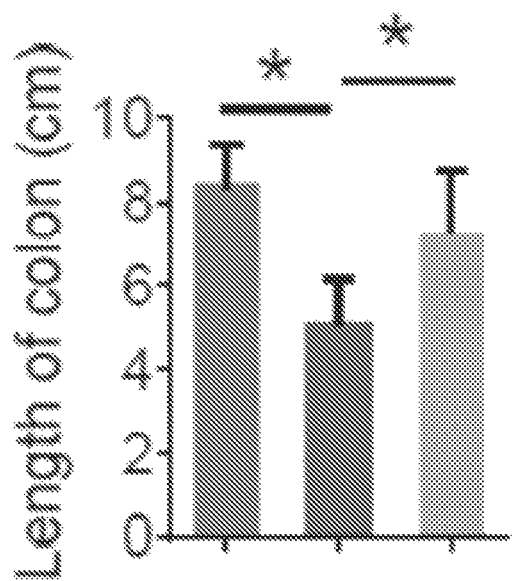
FIG. 32

EDIBLE PLANT-DERIVED NANOPARTICLES FOR REGULATION OF GUT MICROBIOTA

CROSS REFERENCE TO RELATED APPLICATION

This application is based on and claims priority to U.S. Provisional Patent Application Ser. No. 62/589,901, filed Nov. 22, 2017, and U.S. Provisional Patent Application Ser. No. 62/686,421, filed Jun. 18, 2018, the disclosure of each of which is incorporated herein by reference in its entirety.

GOVERNMENT INTEREST

This invention was made with government support under grant numbers UH3TR000875 and R01AT008617 awarded by the National Institutes of Health. The government has certain rights in the invention.

BACKGROUND

The interaction of diet and the gut microbiota to health have emerged in recent years. First, unlike other factors including disease and disease treatment, diet has been clearly demonstrated to have a considerable effect on the composition of the gut microbiota throughout human life (Sonnenburg & Bäckhed, 2016; Sonnenburg et al., 2016; Glenwright et al., 2017). Different human populations can have vastly different intestinal microbiomes, and changes in diet lead to changes in microbiota composition (Maslowski & Mackay, 2011). Second, owing to the essential role of the gut microbiota in maintaining host physiology, its alteration as a result of unhealthy diet can trigger a wide range of physiological disorders, including low-grade inflammation, metabolic disorders, and loss of insulin sensitivity, which increase the risk of developing metabolic diseases (Chassaing et al., 2012; Chassaing & Gewirtz, 2014; Huttenhower et al., 2014; Arrieta et al., 2015; Usami et al., 2015; Patterson et al., 2016; Tang et al., 2017). Third, vegetable and meat are mostly made of cells that contain high levels of nucleic acids including RNA (Hess & Greenberg, 2012; Garcia-Segura et al., 2013). Although it is well known that food, including edible plants, are the main carbon and energy source for gut microbes, the impact of dietary-derived RNA on the gut microbiota are not defined. If the interactions between diet-derived RNA and the microbiome in a sequence-specific manner are determined and understood, manipulation of the microbiome could be optimized for development of food-derived factor-based therapeutic strategies in restoring gut microbiota homeostasis with minimum side effects. Lastly, gene sequencing data have shown that the gut metagenome (that is, all the genes in the community of gut microorganisms) is involved in core functions, such as the digestion and degradation of otherwise indigestible nutrients (Tschop et al., 2009). Whether diet-derived RNA plays a dominate role during communication with gut microbiota rather than being utilized as a nutrient to health is less defined.

Well over half of the animal and human transcriptome is predicted to be under miRNA regulation. miRNA from edible plants has been detected in human blood (Zhang et al., 2012). Whether the expression of gut bacterial genes is regulated by edible plant miRNA is not known. An exosome-like nanoparticle (ELNs) complex (Ju et al., 2013; Record, 2013; Wang et al., 2013; Mu et al., 2014; Wang et al., 2014; Zhuang et al., 2015; Deng et al., 2017) that is present in foods has been described. The published data (Mu et al., 2014; Wang et al., 2014; Deng et al., 2017) further indicate that edible ELNs contain miRNAs (Mu et al., 2014). Little is known about whether the diet-derived ELN RNA communicates with gut bacteria to shape microbiota.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides methods for modulating gut microbiota. In some embodiments, the methods comprise administering to a subject an effective amount of a composition comprising a first edible plant-derived nanoparticle encapsulating an effective amount of RNA, optionally wherein the RNA is obtained from a second edible-plant derived nanoparticle, wherein the effective amount results in a change in the makeup of the subject's gut microbiota relative to that present prior to the administering step. In some embodiments, the first edible plant-derived ELN, the second edible plant-derived ELN, or both are derived from an edible plant selected from the group consisting of ginger, grapefruit, carrot, garlic, and turmeric. In some embodiments, the edible plant is ginger. In some embodiments, effective amount of RNA comprises and effective amount of an miRNA. In some embodiments, the miRNA is selected from the group consisting of miR166c, miRNA167a, miR319a, miR396e, miR842, and miR827. In some embodiments, the gut microbiota that is modulated is a Lactobacillaceae, a Bacteroidaceae, a Clostridiaceae, a Ruminococcaceae, or any combination thereof. In some embodiments, the modulating comprises increasing numbers of Lactobacillaceae and/or Bacteroidaceae, decreasing numbers of Clostridiaceae and/or Ruminococcaceae, or both in the gut microbiota of the subject.

In some embodiments, the presently disclosed subject matter also provides methods for preventing and/or treating gut dysbiosis. In some embodiments, the methods comprise administering to a subject an effective amount of a composition comprising a first edible plant-derived nanoparticle encapsulating an effective amount of RNA, optionally wherein the RNA obtained from a second edible-plant derived nanoparticle, wherein the effective amount results in a change in the makeup of the subject's gut microbiota relative to that present prior to the administering step, thereby preventing and/or treating gut dysbiosis in the subject. In some embodiments, the first edible plant-derived ELN, the second edible plant-derived ELN, or both are derived from an edible plant selected from the group consisting of ginger, grapefruit, carrot, garlic, and turmeric. In some embodiments, the edible plant is ginger. In some embodiments, effective amount of RNA comprises and effective amount of an miRNA. In some embodiments, the miRNA is selected from the group consisting of miR166c, miRNA167a, miR319a, miR396e, miR842, and miR827. In some embodiments, the gut microbiota that is modulated is a Lactobacillaceae, a Bacteroidaceae, a Clostridiaceae, a Ruminococcaceae, or any combination thereof. In some embodiments, the gut dysbiosis comprises inflammation. In some embodiments, the gut dysbiosis is colitis. In some embodiments, the first edible plant-derived nanoparticle is a ginger exosome-like nanoparticle (ELN) that encapsulates an effective amount of an miRNA. In some embodiments, the ginger ELN is present within a *Lactobacillus rhamnosus* GG (LGG) bacterium that is administered to the subject. In some embodiments, the LGG bacterium comprising the ginger ELN is administered orally to the subject. In some embodiments, the administering step comprises administering to the subject a dose of 1-1000 mg/kg, optionally a dose of 20-400 mg/kg.

In some embodiments, the presently disclosed subject matter provides methods for personalized medicine. In some embodiments, the methods comprise screening a subject for a suboptimal gut microbiota, wherein the suboptimal gut microbiota comprises a profile of gut bacterial that can be improved, identifying one or more gut bacteria that could provide a health benefit to the subject, and administering to the subject one or more compositions comprising a first edible plant-derived nanoparticle encapsulating an effective amount of RNA, optionally wherein the RNA is obtained from a second edible-plant derived nanoparticle, wherein the effective amount results in a desirable change in the makeup of the subject's gut microbiota relative to that present prior to the administering step.

The presently disclosed subject matter also provides in some embodiments methods for modulating growth of a bacterium in a subject's digestive system. In some embodiments, the methods comprise administering to the subject an exosome-like nanoparticle (ELN) in an amount and by a route sufficient to modulate the growth of the *Lactobacillus* bacterium in the subject's digestive system. In some embodiments, the ELN is a ginger ELN (GELN) and the administering results in an increase in the number of Lactobacillaceae and/or Bacteroidaceae in the subject's digestive system, a decrease in the number of Clostridiaceae and/or Ruminococcaceae in the subject's digestive system, or both. In some embodiments, the ELN is a grapefruit ELN (GFELN) and the administering results in a decrease in the number of Lactobacillaceae in the subject's digestive system. In some embodiments, the bacterium is a Lactobacillaceae and the ELN comprises an miR396 microRNA.

In some embodiments, the presently disclosed subject matter also provides methods for modulating one or more inflammatory cytokines in the gut of a subject. In some embodiments, the methods comprise administering to the subject an effective amount of an edible plant-derived nanoparticle encapsulating an effective amount of RNA and/or an RNA isolated therefrom, whereby an inflammatory cytokine in the gut of the subject is modulated. In some embodiments, the inflammatory cytokine is selected from the group consisting of tumor necrosis factor α (TNFα), interleukin 1β (IL-1β), interleukin 22 (IL-22), or a combination thereof. In some embodiments, the administering reduces TNFα and/or IL-1β in the gut of the subject. In some embodiments, the administering increases IL-22 expression in the gut of the subject. In some embodiments, the administering protects against and/or reduces inflammation in the gut of the subject.

The presently disclosed subject matter also provides in some embodiments methods for reducing migration of Lactobacillaceae from the gut to gut-associated bloodstream of a subject. In some embodiments, the methods comprise contacting Lactobacillaceae with a plurality of ginger exosome-like nanoparticles (GELNs) and/or RNA derived therefrom under conditions sufficient for the GELNs and/or RNA derived therefrom to be taken up by the Lactobacillaceae; and administering the Lactobacillaceae in an amount sufficient for the Lactobacillaceae to colonize the gut of the subject, whereby migration of the Lactobacillaceae from the gut to the gut-associated bloodstream of the subject is reduced. In some embodiments, the GELNs and/or the RNA derived therefrom comprise an microRNA selected from the group consisting of a miR167a species or a precursor thereof, an miR842 species or a precursor thereof, an miR827 species or a precursor thereof, or any combination thereof. In some embodiments, the miRNA167a microRNA and/or the precursor thereof is present in an amount sufficient to reduce expression of a spaC gene product in the Lactobacillaceae.

In some embodiments of all of the presently disclosed methods, the subject is a mammal, optionally a human.

The presently disclosed subject matter also provides in some embodiments compositions comprising a first edible plant-derived exosome-like nanoparticle (ELN) encapsulating an effective amount of an RNA, the RNA obtained from a second edible-plant derived nanoparticle. In some embodiments, the first edible plant-derived ELN, the second edible 33plant-derived ELN, or both are derived from an edible plant selected from the group consisting of ginger, grapefruit, carrot, garlic, and turmeric. In some embodiments, the edible plant is ginger. In some embodiments, the effective amount of RNA comprises and effective amount of an miRNA. In some embodiments, the miRNA is selected from the group consisting of miR166c, miRNA167a, miR319a, miR396e, miR842, and miR827. In some embodiments, the effective amount of the RNA is sufficient to modulate gut microbiota in a subject when the composition is administered to a subject. In some embodiments, the gut microbiota that is modulated is from a member of Lactobacillaceae, Bacteroidaceae, Clostridiaceae, or Ruminococcaceae.

The presently disclosed subject matter also provides in some embodiments pharmaceutical compositions comprising the compositions as disclosed herein and at least one pharmaceutically acceptable carrier, diluent, and/or excipient. In some embodiments, the pharmaceutical composition is pharmaceutically acceptable for use in a human. In some embodiments, the pharmaceutical composition is formulated for oral administration.

Thus, it is an object of the presently disclosed subject matter to provide compositions and methods for regulating and modifying the gut microbiota.

An object of the presently disclosed subject matter having been stated hereinabove, and which is achieved in whole or in part by the presently disclosed subject matter, other objects will become evident as the description proceeds when taken in connection with the accompanying Figures as best described herein below.

BRIEF DESCRIPTION OF THE FIGURES

FIG. 30 is a bar graph of body weight at days 0-8 (GELN-RNAs vs. scrambled RNAs: *p<0.05 and **p<0.01).

FIG. 31 is a plot of survival of mice after administration of 2.5% DSS in drinking water. In FIG. 1E, the left plot is DSS+GNVs with scrambled RNAs, and the right blot is DSS+GNVs/GELN-RNAs.

FIG. 32 is a bar graph of the quantification of colon length in mice treated as indicated. *p<0.05.

in colon mucus are shown. The data are representative of three independent experiments (n=5; Error bars are ±SD). *p<0.05 and **p<0.01 by two-tailed t-test. NS, not significant. Error bars are ±SD).

Figure 40:
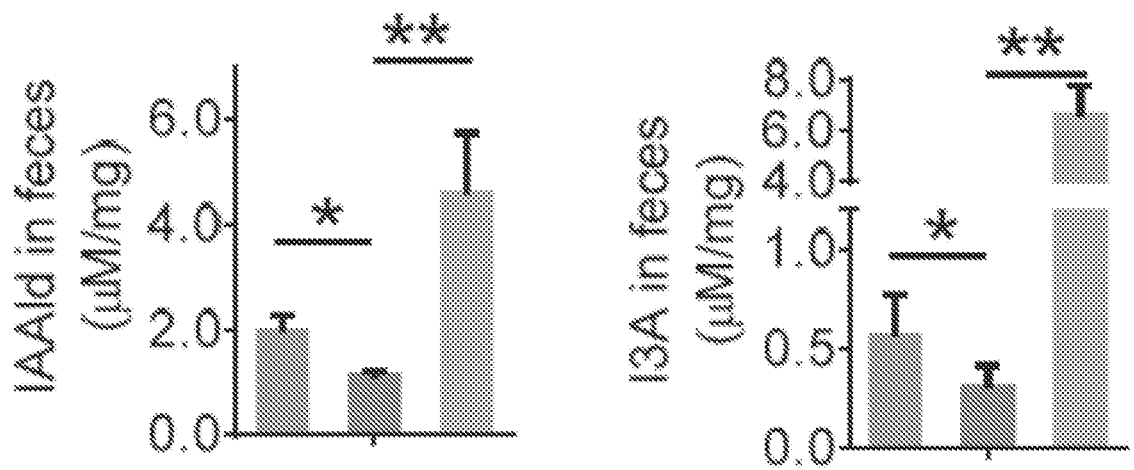
Figure 41:
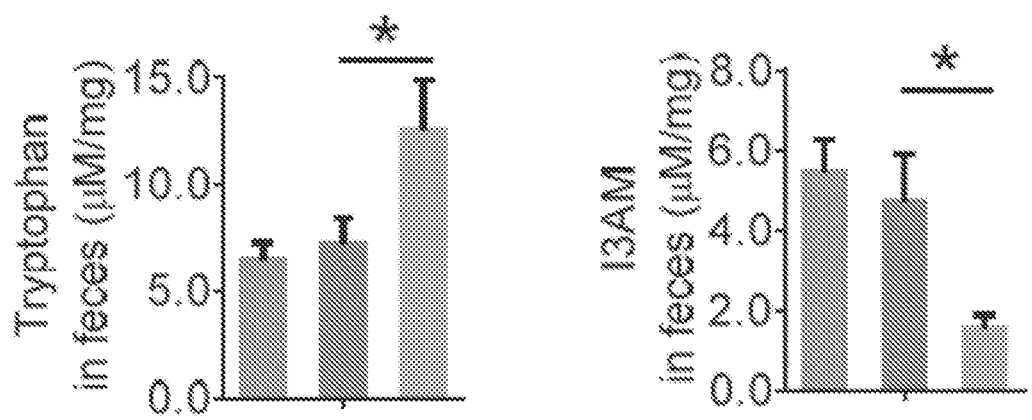

FIGS. 40 and 41 are a series of bar graphs showing the results of high-performance liquid chromatography (HPLC) analyses indicated that the level of I3A in the feces of GELN-RNA-treated C57BL/6 mice dramatically increased (FIG. 40) compared with that in feces from mice treated with GELN-scrambled RNA, whereas the level of indole-3 acetamide (I3AM), another metabolite of tryptophan, decreased (FIG. 41). Arrows point to the peak of the standard. *P<0.05; **P<0.01.

Figure 42:
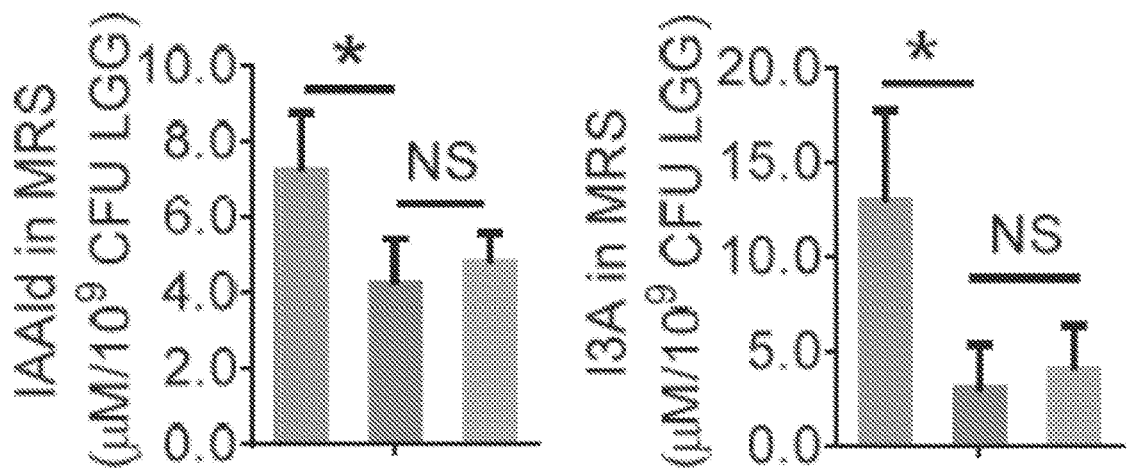

FIG. 42 is a pair of bar graphs quantifying the concentrations of the metabolites listed in LGG grown in MRS medium with I3AM and GNV/scrambled RNAs or GNV/GELN-RNAs for 6 hours determined by HPLC analysis of IAAld and I3A in the MRS medium*p<0.05.

Figure 43:
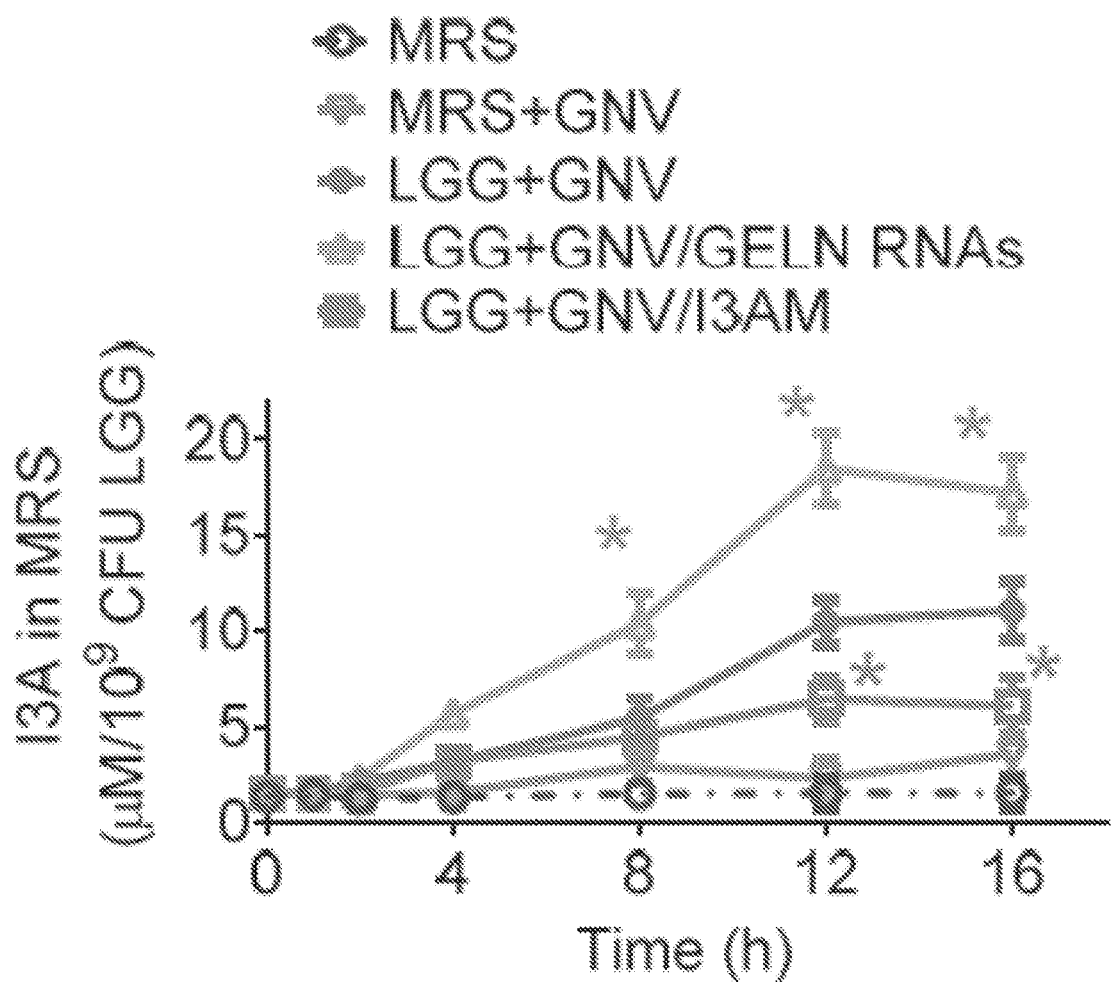

FIG. 43 is a graph summarizing the results of HPLC analysis of I3A in LGG cultures in the presence of I3AM at the times indicated. GNV/GELN-RNAs vs. GNV and GNV/I3AM vs. GNV where both *p<0.05.

Figure 44:
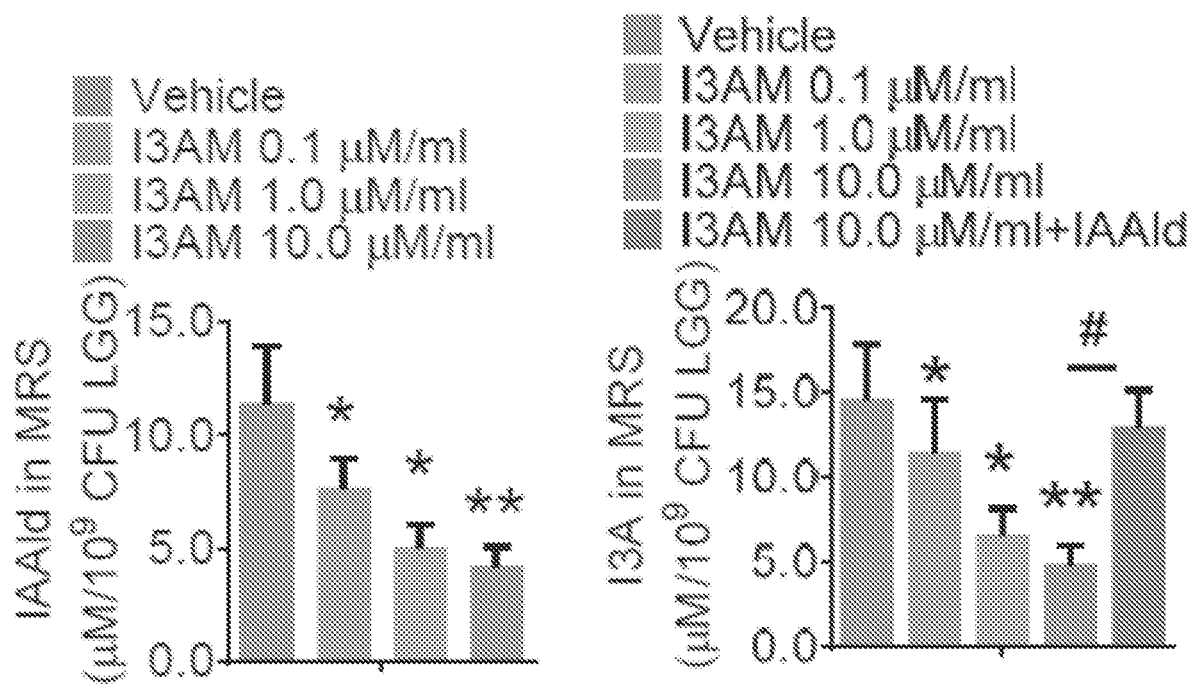

FIG. 44 is a pair of bar graphs of HPLC analyses of IAAld (left panel) and I3A (right panel) in MRS medium from LGG treated with I3AM at the different concentrations indicated without or with IAAld. *P<0.05; **P<0.01.

Figure 45:
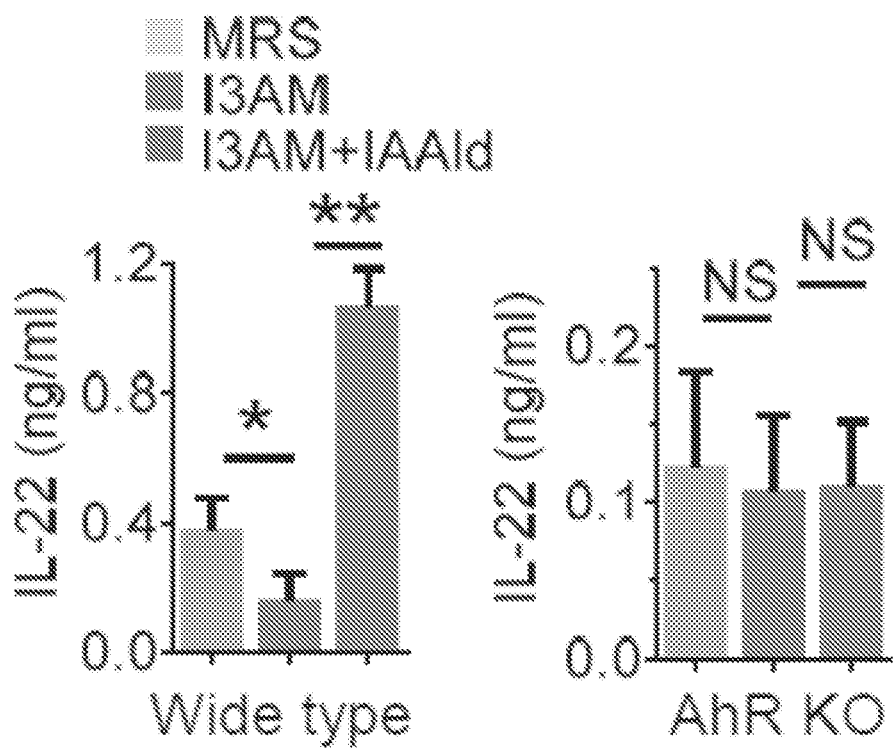

FIG. 45 is a pair of bar graphs showing the results of ELISA analyses of IL-22 in colon mucus of wild type mice (WT; left panel) or AHR KO mice (right panel) gavaged with MRS medium from LGG treated with I3AM. The data are representative of three independent experiments. Error bars are ±SD. *p<0.05; **p<0.01.

Figure 46:
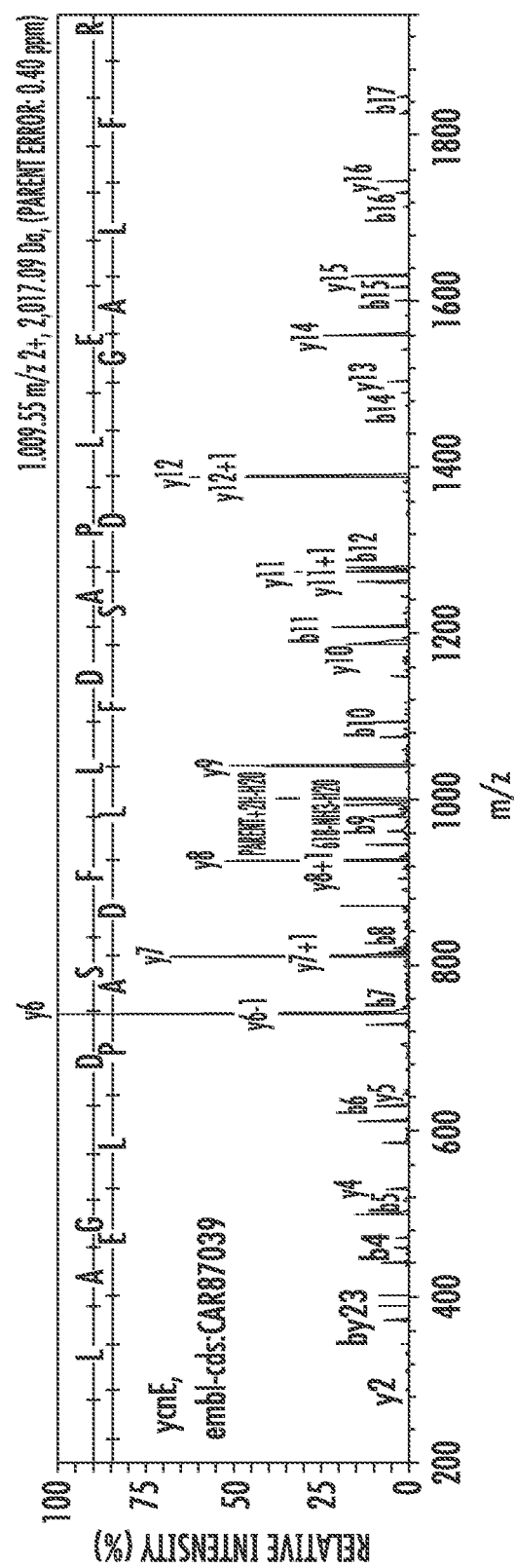

FIG. 46 is an exemplary LC-MS spectra of monooxygenase ycnE from LGG.

Figure 47:
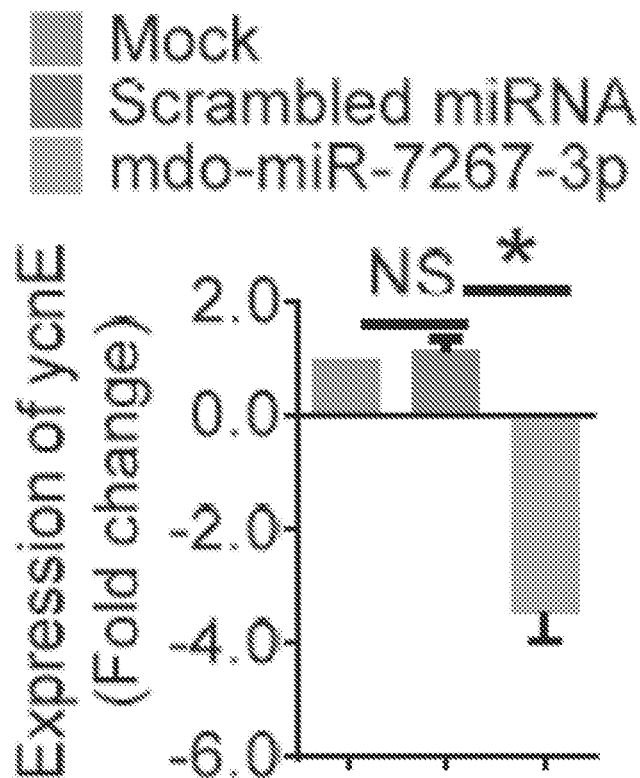

FIG. 47 is a bar graph of qPCR analysis of ycnE expression in LGG treated with mdo-miR7267-3p or scrambled miRNA. Error bars are ±SD. NS: not significant. *p<0.05.

Figure 48:
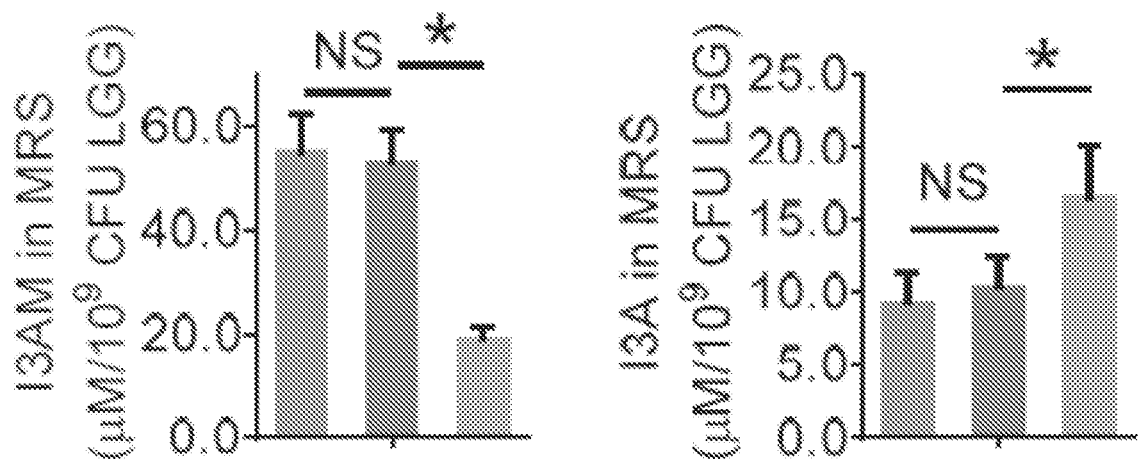

FIG. 48 is a pair of bar graphs of HPLC analyses of I3AM (left panel) and I3A (right panel) in LGG cultures treated with mdo-miR7267-3p. Error bars are ±SD. NS: not significant. *p<0.05.

Figure 49:
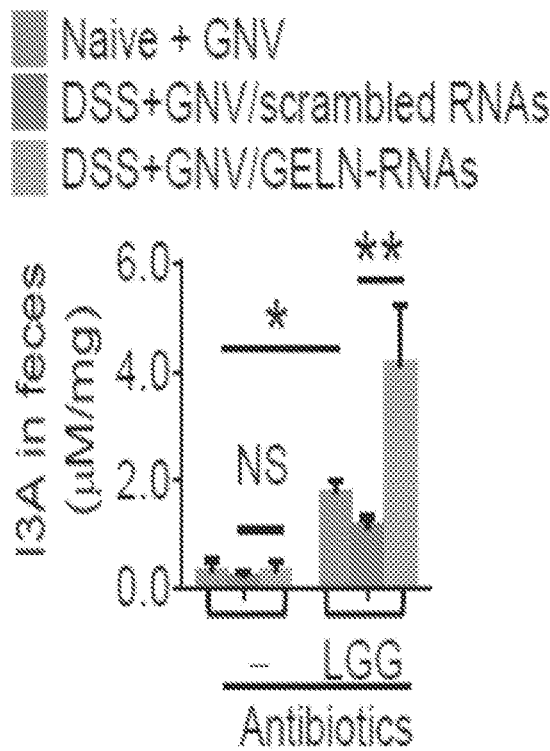

FIG. 49 is a bar graph of HPLC analysis of I3A in feces of mice treated with antibiotics in drinking water for one week followed by an oral gavage treatment as indicated (n=5). Error bars are ±SD. NS: not significant. *p<0.05. **p<0.01.

Figure 50:
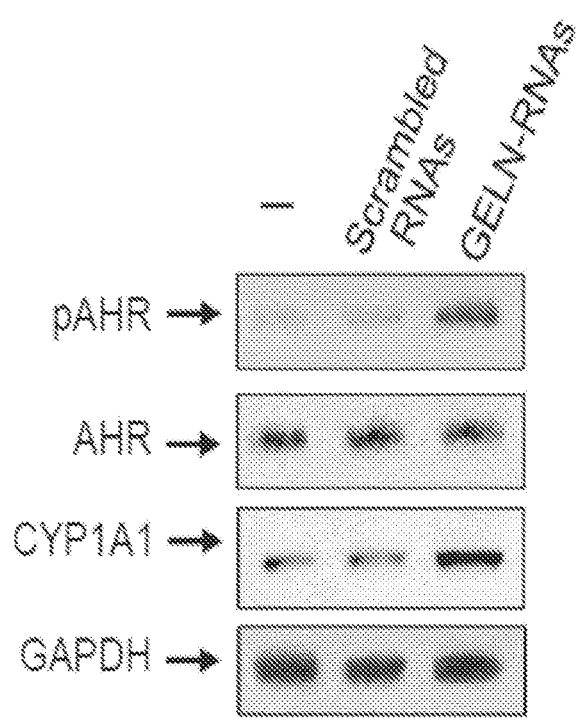

FIG. 50 is a representative Western blot of AHR, AHR phosphorylated at Ser36 (pAHR), CYP1A1, and GAPDH (loading control) in colon lymphocytes.

Figure 51:
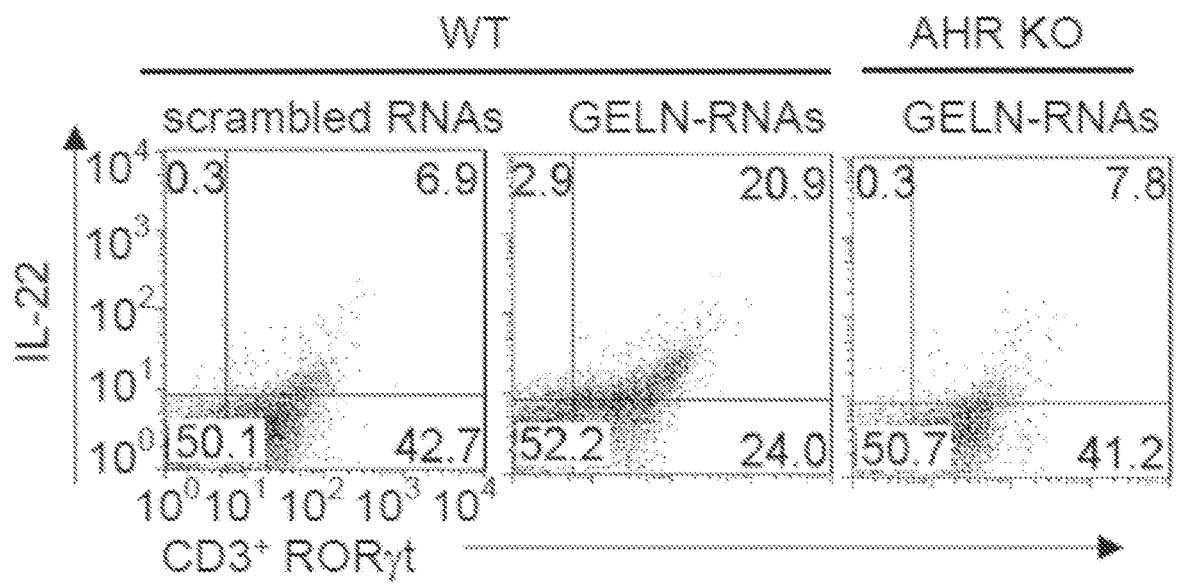

FIG. 51 is a series of representative FACS plots of IL-22, CD3, and the RAR-related orphan receptor gamma t isoform (RORγt) expression in colon lymphocytes. The numbers in quadrants indicate the percentage of cells in each.

Figure 52:
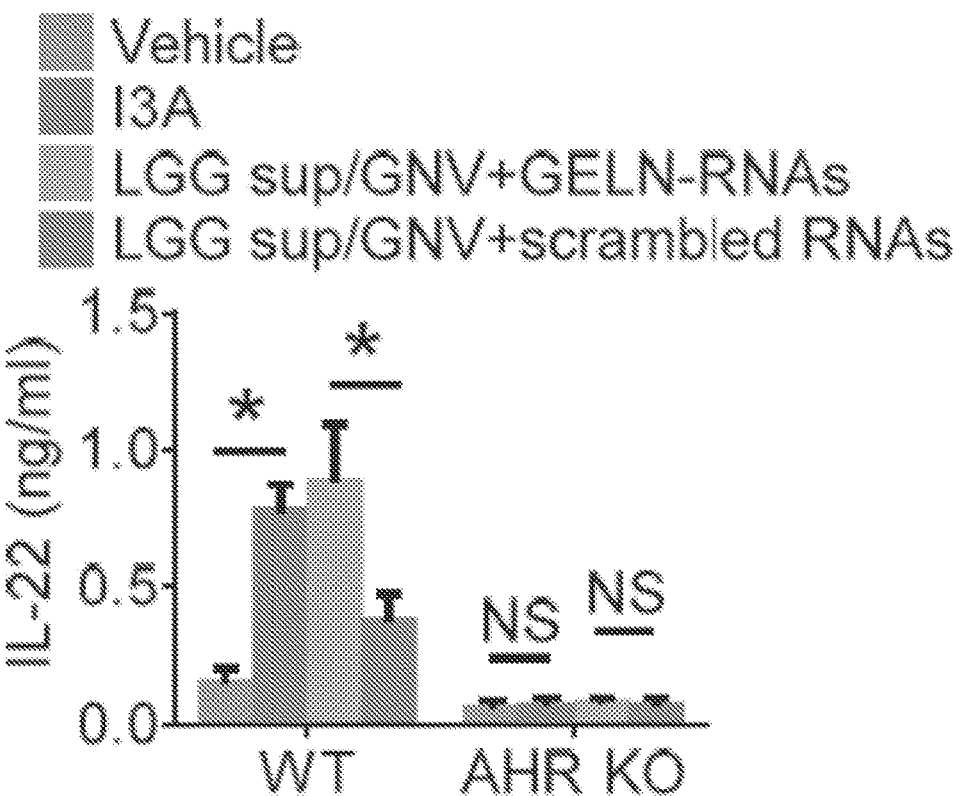

FIG. 52 is a bar graph of ELISA analysis of IL-22 concentration in cell supernatants of colon lymphocytes isolated from WT and AHR KO mice (n=5 each) and incubated with I3A or supernatant from LGG treated with the agents listed. Error bars are ±SD. NS: not significant. *p<0.05.

Figure 53:
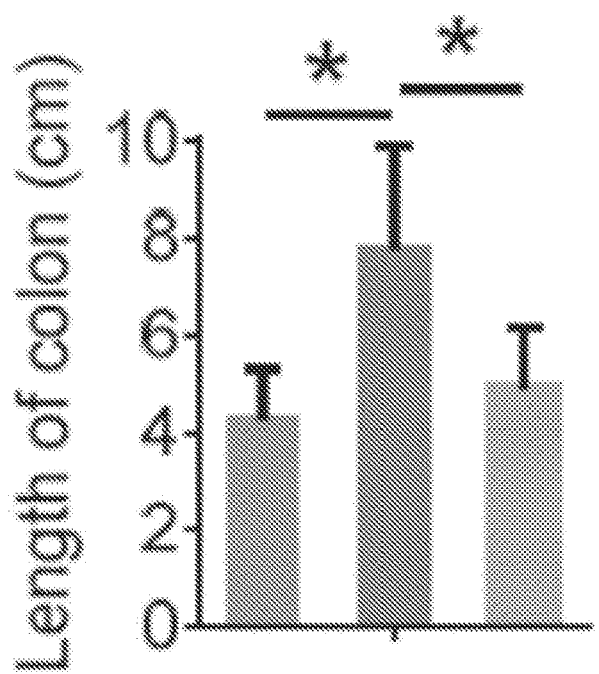

FIG. 53 is a bar graph of representative colon lengths from WT mice treated with GNV (left bar), treated with GNV/GELN-RNAs (middle bar) or IL-22 KO mice treated with GNV/GELN-RNAs (right bar). Error bars are ±SD. *p<0.05.

Figure 54:
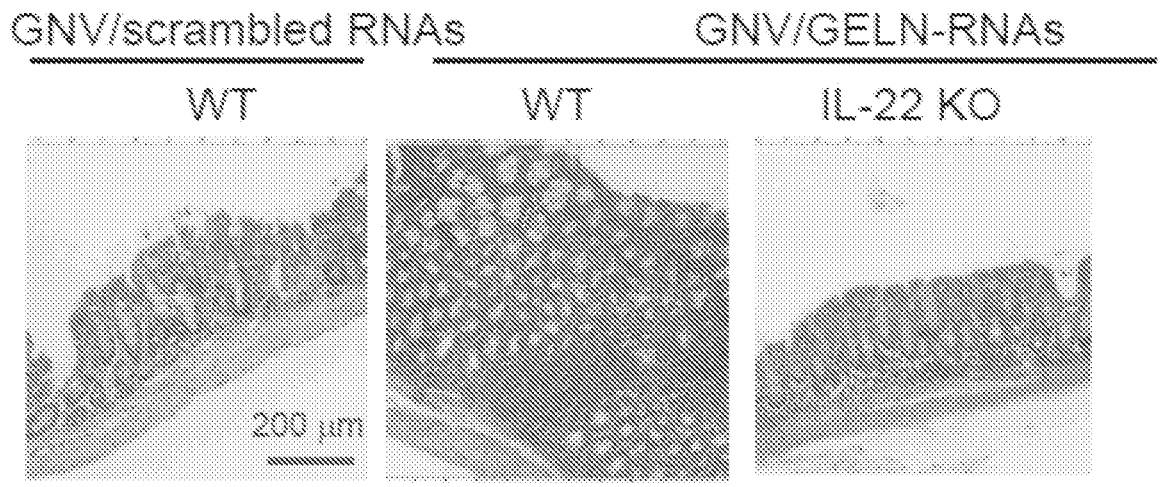

FIG. 54 is a series of H&E-stained sections of colon (400× magnification) from WT and IL-22 KO mice treated as indicated.

Figure 55:
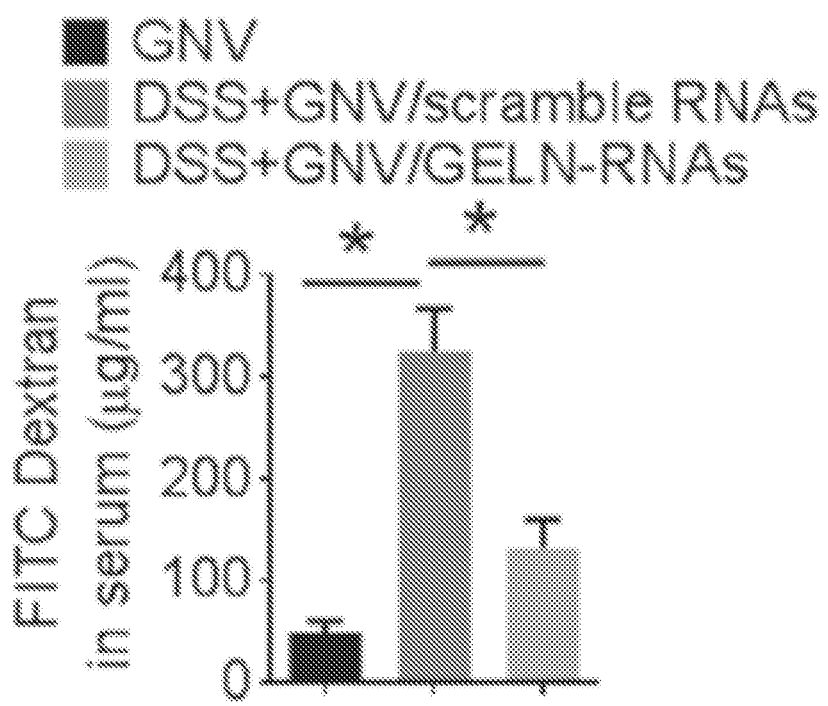

FIG. 55 is a bar graph showing the results of C57BL/6 mice (n=5) treated with GNV/GELN-RNA via oral gavage for one week along with 2.5% DSS in the drinking water; 2.5% DSS supplied in drinking water was continued for an additional week. Then, the mice were orally gavaged with FITC-Dextral 4000 (60 mg 100/g of body weight) and serum collected 5 hours after gavage to estimate intestinal permeability. Error bars are ±SD. *p<0.05.

Figure 56:
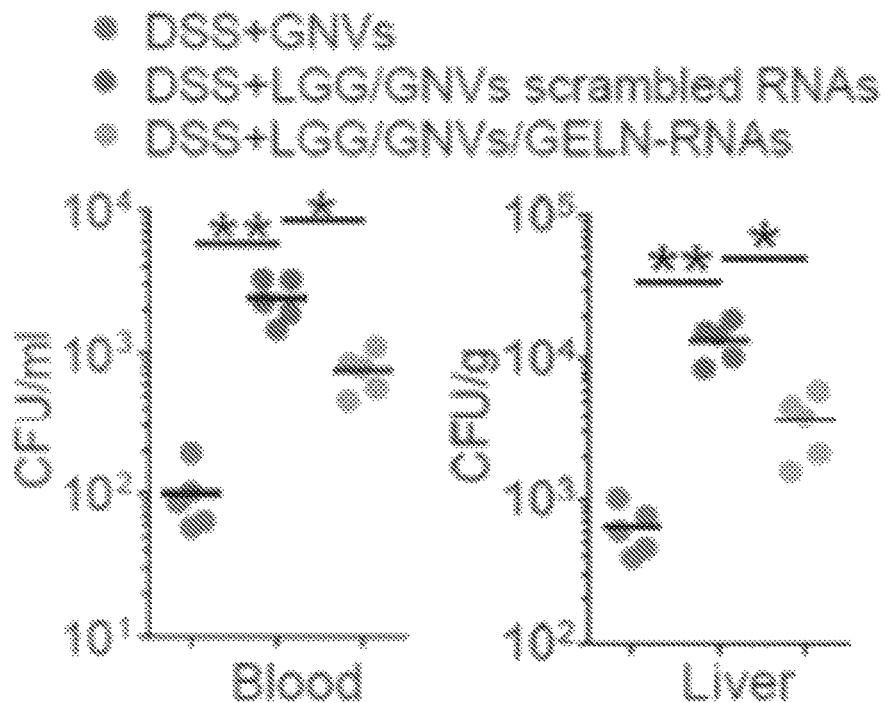

FIG. 56 is a series of plots of C57BL/6 mice supplemented with 2.5% DSS following gavage with $10^9$ CFU LGG treated with GNV/GELN-RNA or GNV/scrambled RNA. Representative numbers of bacteria colonies in the blood and liver cultured on MRS agar plates were quantified as bacteria CFU; each symbol represents an individual mouse (n=5). *p<0.05 and **p<0.01 (two-tailed t-test).

Figure 57:
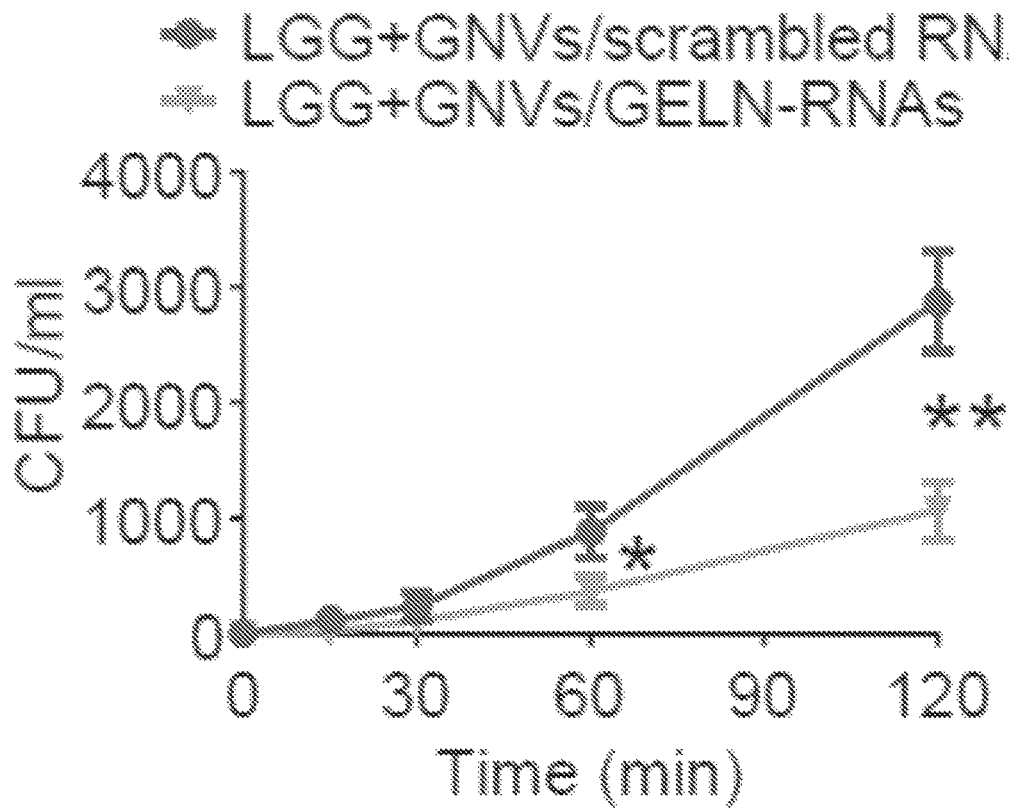

FIG. 57 shows a graph quantifying the results of blood cultured on MRS agar plates at different time points after gavage as indicated. *p<0.05.

Figure 58:
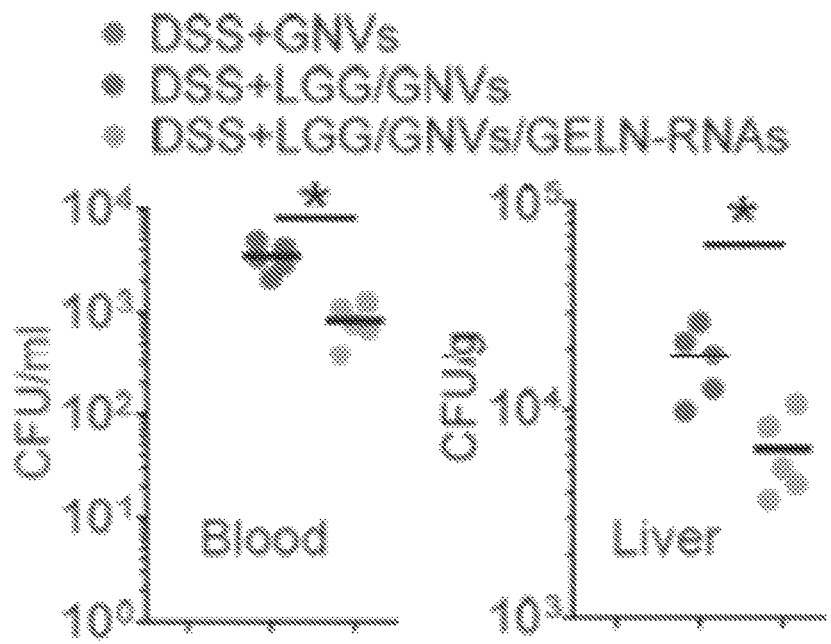

FIG. 58 is a graph showing the results of germ-free mice treated using the same procedure as in FIG. 57.

Figure 59:
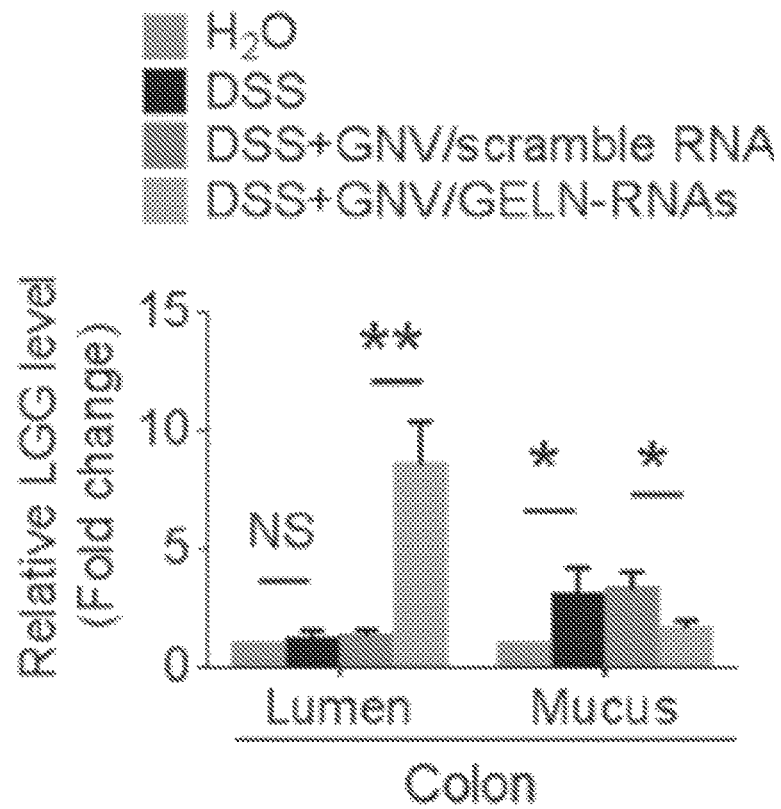

FIG. 59 is a pair of bar graphs after oral gavage with GNV/GELN-RNA daily for one week, mice (n=5) were continually treated with GNV/GELN-RNAs or GNV/scramble RNAs while provided 2.5% DSS in drinking water for one additional week. Mice were sacrificed and LGG in lumen and mucus of colon was analyzed by qPCR. The relative LGG level normalized to 16s universal PCR product was calculated and presented. Data are representative of three independent experiments. Error bars are ±SD. *p<0.05. ** p<0.01 (two-tailed t-test).

Figures 60A, 60B:
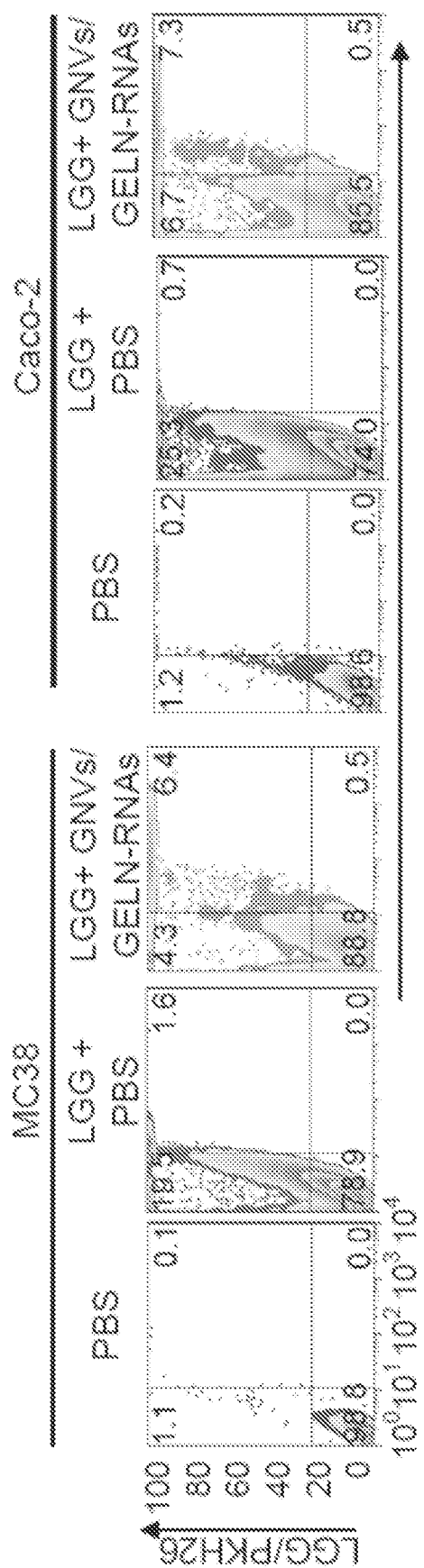

FIGS. 60A and 60B are a series of FACS plots of MC38 cells (FIG. 60A) or Caco-2 cells (FIG. 60B) inoculated with LGG treated with GNVs/GELN-RNAs, and the frequency of PKH26-labeled LGG and PKH67-labeled GNVs/GELN-RNAs was assessed using flow cytometry. The numbers in quadrants indicate the percentage of LGG in each.

Figure 61:
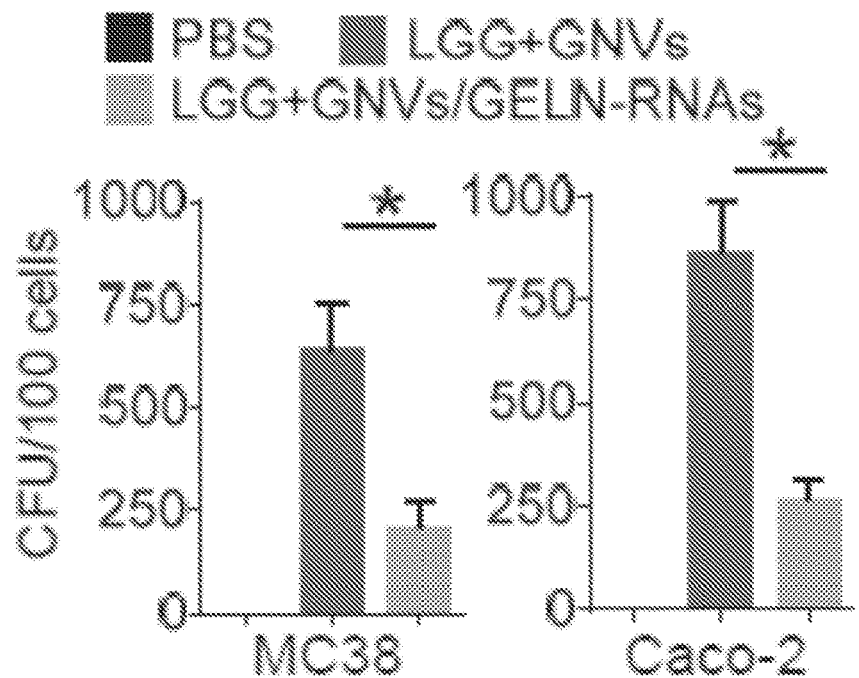

FIG. 61 is a pair of bar graphs quantifying the number of CFUs of intracellular bacteria determined by plating on MRS plates. Error bars are ±SD. *p<0.05.

Figure 62:
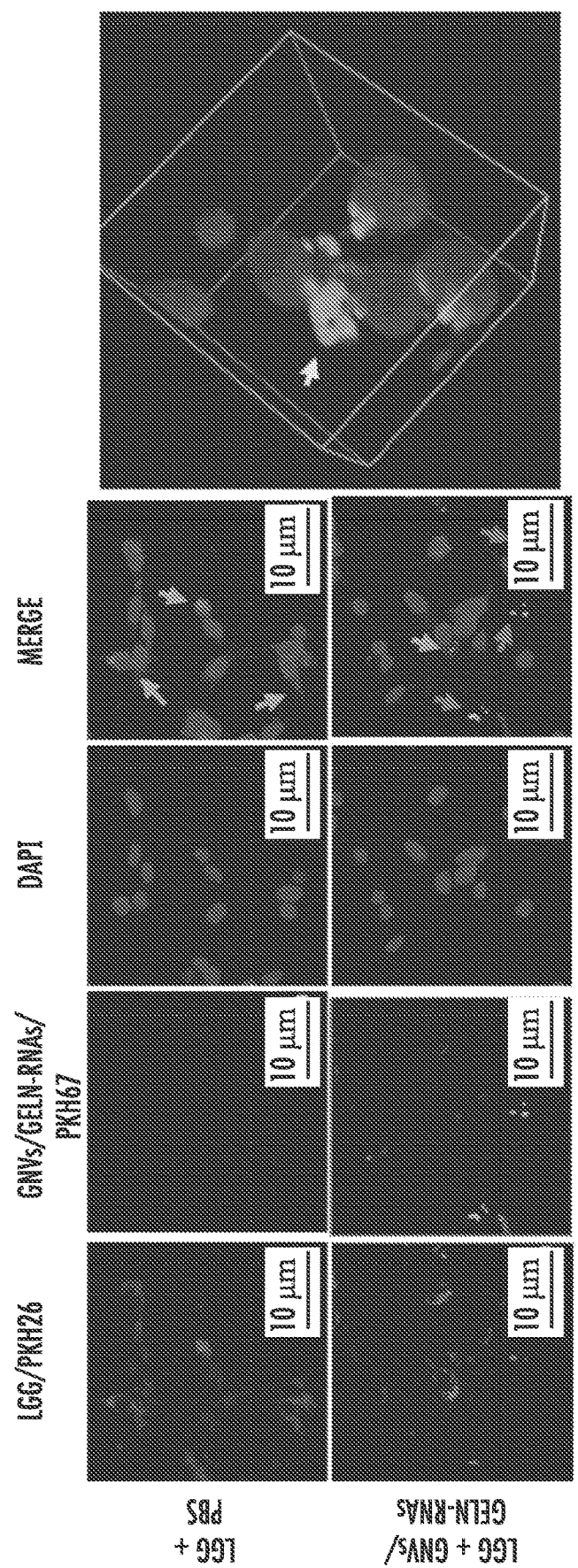

FIG. 62 is a visualization via confocal microscopy of MC38 cells presented with LGG and LGG/GELN-RNAs. Dark gray arrows indicate LGG/PKH26; light gray arrows in green indicate GNVs/GELN-RNAs/PKH67. Scale bars are 10 mm. The rightmost panel is a 3D image showing colocalization of LGG/PKH26 and GNVs/GELN-RNAs/PKH67 in MC38 cells (white arrow). The data are representative of three independent experiments. Error bars are ±SD.

Figure 63:
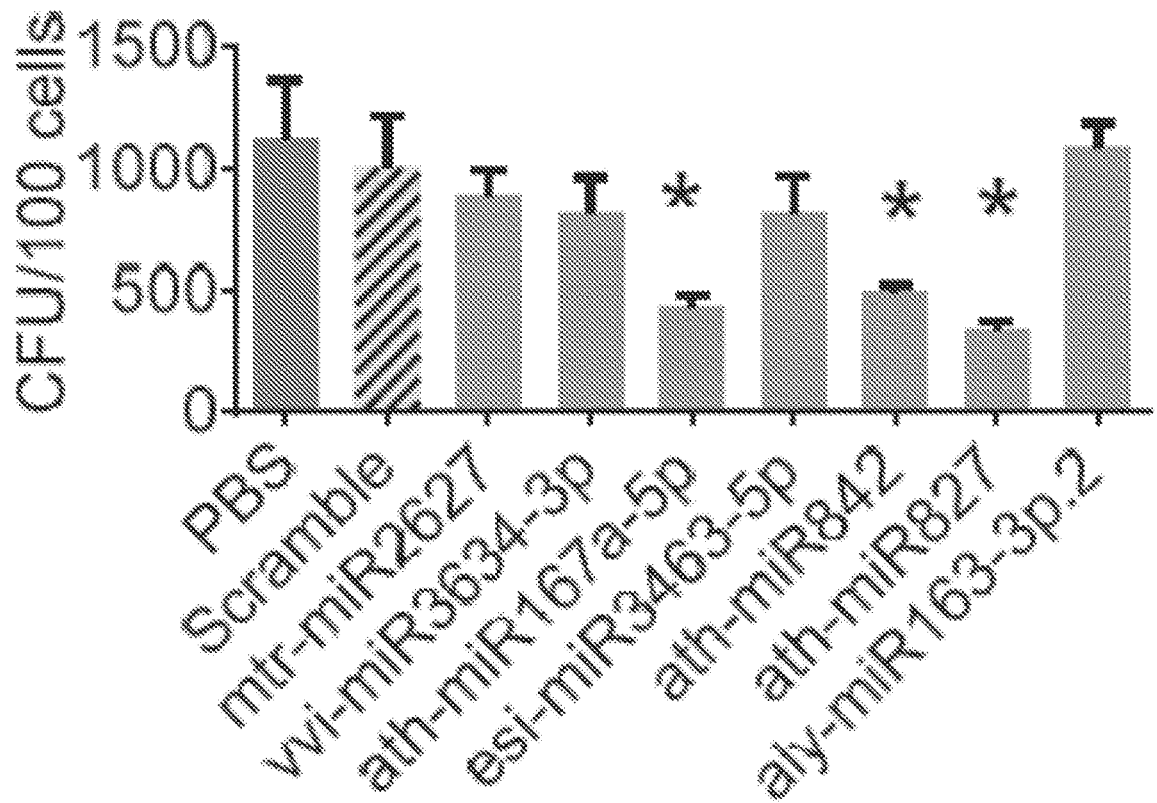

FIG. 63 is a bar graph of CFU number on MRS plates of MC38 cells inoculated with $10^7$ LGG prior to being presented with selected ginger ELN miRNAs as indicated. The number of intracellular LGG is presented. Error bars are ±SD. *p<0.05.

Figure 64:
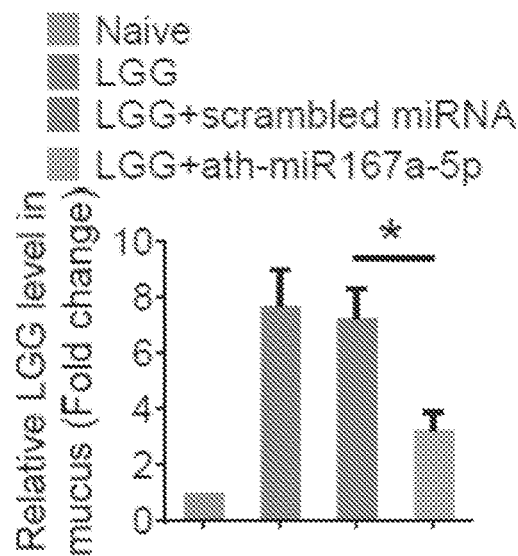

FIG. 64 is a bar graph of qPCR quantification of LGG on mucus. *p<0.05.

Figure 65:
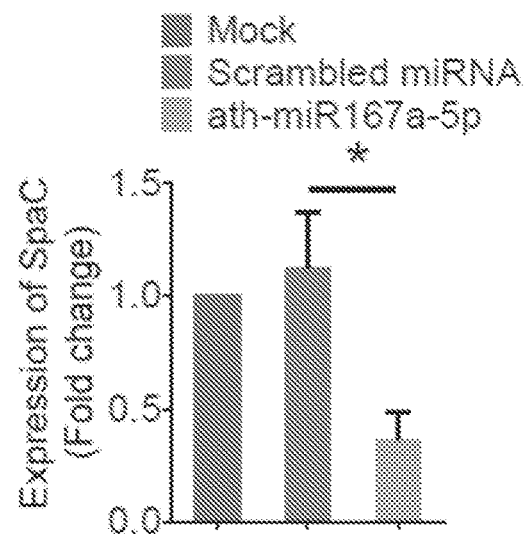

FIG. 65 is a bar graph showing ath-miR167a mimic knock-down of SpaC in LGG evaluated by qPCR. *p<0.05.

Figure 66:
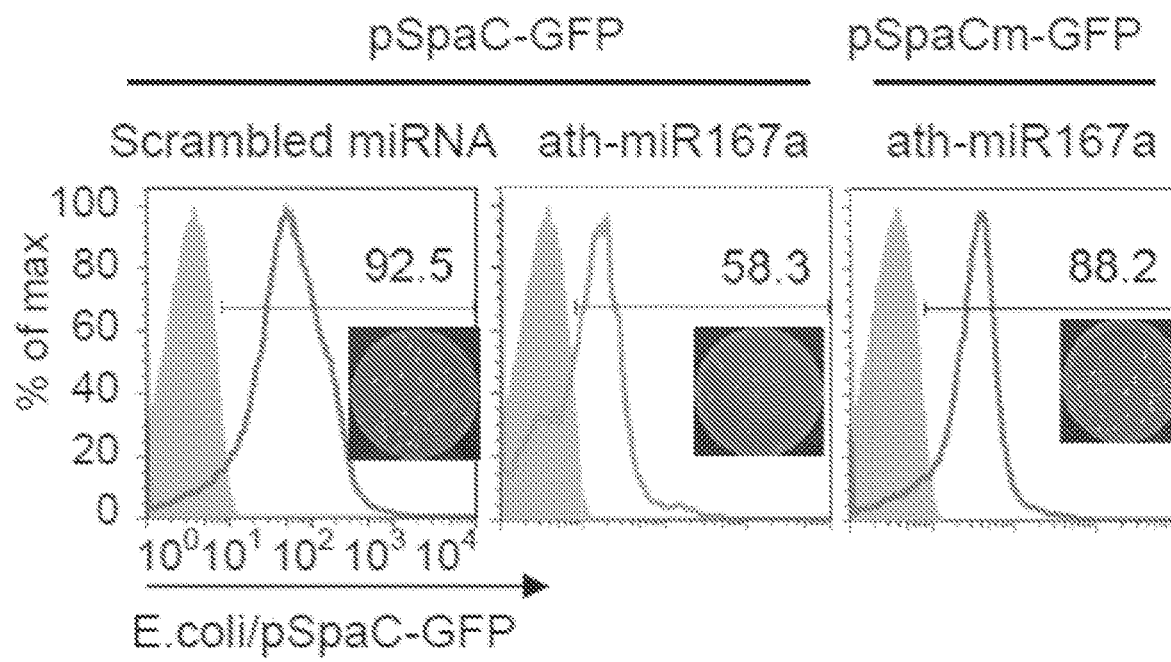

FIG. 66 is a series of FACS plots of fluorescence of *E. coli* containing the constructs when treated as indicated.

Figure 67:
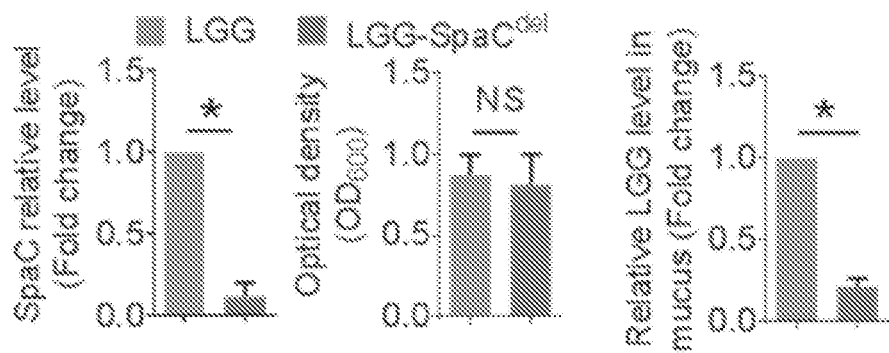

FIG. 67 is a series of bar graphs of expression of SpaC in LGG and LGG-SpaCdel using qPCR (left panel); viability of LGG and LGG-SpaCdel after 8 hours growth in MRS at 37° C. as shown by optical density at 600 nm (middle panel); and LGG level in mucus of mice fed with LGG and LGG-SpaCdel (right panel) using qPCR. Error bars are ±SD. *p<0.05.

Figure 68:
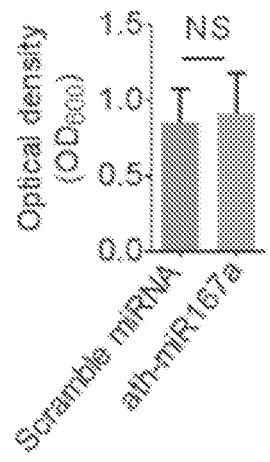

FIG. 68 is a bar graph of optical density of LGG treated with ath-miR167a and scramble miRNA at $OD_{600}$. Error bars are ±SD. NS: not significant.

Figure 69:
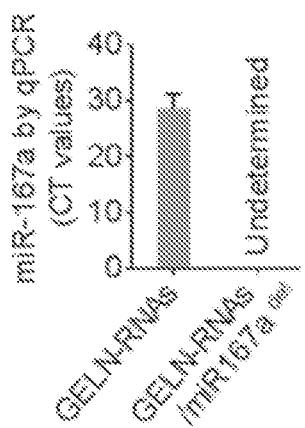

FIG. 69 is a bar graph of miR-167a evaluated by qPCR. miR167a-5p was depleted from the pooled GELN RNAs with biotinylated anti-sense miR167a-5p (miR167a$^{del}$) and packed in GELN-derived lipid. Error bars are ±SD.

Figure 70:
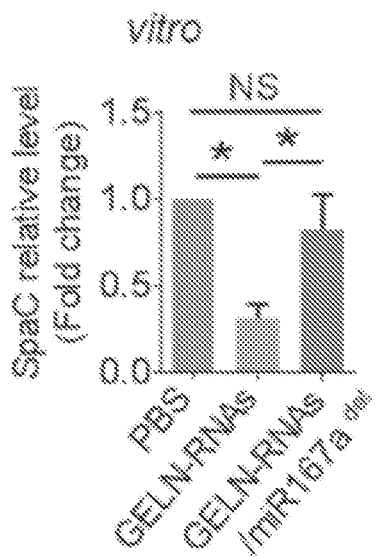

FIG. 70 is a bar graph of SpaC expression estimated with qPCR for LGG treated with GELN-RNAs and GELN-RNAs/miR167a$^{del}$ for 2 hours. Error bars are ±SD. NS: not significant. *p<0.05.

Figure 71:
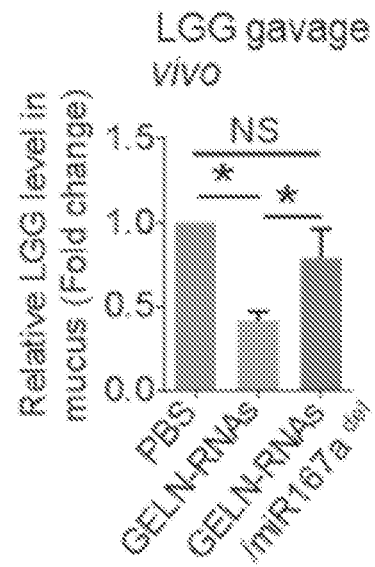

FIG. 71 is a bar graph of LGG in mucus using qPCR for ginger-derived GNVs packed with GELN-RNAs and GELN-RNAs/miR167a$^{del}$, following administration of gavage for C57BL/6 mice. Data are representative of three independent experiments. error bars±SD. *p<0.05 by two-tailed t-test.NS: not significant.

BRIEF DESCRIPTION OF THE SEQUENCE LISTING

SEQ ID NOs: 1 and 2 are the nucleotide sequences of exemplary oligonucleotides that can be employed for amplifying a SpaC fragment that includes the ginger ELN (GELN) ath-miR167a target sequence.

SEQ ID NOs: 3 and 4 are the nucleotide sequences of exemplary oligonucleotides that can be employed for mutating the GELN ath-miR167a target sequence.

SEQ ID NOs: 5 and 6 are the nucleotide sequences of exemplary oligonucleotides that can be employed for amplifying v1-v3 regions of bacterial 16S rRNA genes.

SEQ ID NOs: 7 and 8 are the nucleotide sequences of exemplary oligonucleotide adaptors that can be employed for anchoring oligonucleotides for multiplexing.

SEQ ID NO: 9 is the nucleotide sequence of the mature ath-miR167a-5p.

SEQ ID NO: 10 is the nucleotide sequence of an exemplary oligonucleotide primer that can be employed along with the QIAGEN Universal Reverse Primer in a quantitative PCR (qPCR) reaction of an osa-miR820a (SEQ ID NO: 141) nucleic acid.

SEQ ID NO: 11 is the nucleotide sequence of an exemplary oligonucleotide primer that can be employed along with the QIAGEN Universal Reverse Primer in a quantitative PCR (qPCR) reaction of an ath-miR167a-5p nucleic acid.

SEQ ID NO: 12 is the nucleotide sequence of an exemplary oligonucleotide primer that can be employed along with the QIAGEN Universal Reverse Primer in a quantitative PCR (qPCR) reaction of an osa-miR820a (SEQ ID NO: 141) nucleic acid.

SEQ ID NO: 13 is the nucleotide sequence of an exemplary oligonucleotide primer that can be employed along with the QIAGEN Universal Reverse Primer in a quantitative PCR (qPCR) reaction of a vvi-miR3634-3p (SEQ ID NO: 159) nucleic acid.

SEQ ID NO: 14 is the nucleotide sequence of an exemplary oligonucleotide primer that can be employed along with the QIAGEN Universal Reverse Primer in a quantitative PCR (qPCR) reaction of an ath-miR842 (SEQ ID NO: 82) nucleic acid.

SEQ ID NO: 15 is the nucleotide sequence of an exemplary oligonucleotide primer that can be employed along with the QIAGEN Universal Reverse Primer in a quantitative PCR (qPCR) reaction of a ppt-miR1028a-3p (SEQ ID NO: 144) nucleic acid.

SEQ ID NO: 16 is the nucleotide sequence of an exemplary oligonucleotide primer that can be employed along with the QIAGEN Universal Reverse Primer in a quantitative PCR (qPCR) reaction of an osa-miR2865 (SEQ ID NO: 137) nucleic acid.

SEQ ID NO: 17 is the nucleotide sequence of an exemplary oligonucleotide primer that can be employed along with the QIAGEN Universal Reverse Primer in a quantitative PCR (qPCR) reaction of an aly-miR163-3p.2 nucleic acid.

SEQ ID NO: 18 is the nucleotide sequence of an exemplary oligonucleotide primer that can be employed along with the QIAGEN Universal Reverse Primer in a quantitative PCR (qPCR) reaction of an osa-miR166j-5p (SEQ ID NO: 136) nucleic acid.

SEQ ID NO: 19 is the nucleotide sequence of an exemplary oligonucleotide primer that can be employed along with the QIAGEN Universal Reverse Primer in a quantitative PCR (qPCR) reaction of an esi-miR3463-5p (SEQ ID NO: 97) nucleic acid.

SEQ ID NO: 20 is the nucleotide sequence of an exemplary oligonucleotide primer that can be employed along with the QIAGEN Universal Reverse Primer in a quantitative PCR (qPCR) reaction of an aly-miR3447-5p (SEQ ID NO: 66) nucleic acid.

SEQ ID NO: 21 is the nucleotide sequence of an exemplary oligonucleotide primer that can be employed along with the QIAGEN Universal Reverse Primer in a quantitative PCR (qPCR) reaction of an esi-miR3469-3p (SEQ ID NO: 98) nucleic acid.

SEQ ID NO: 22 is the nucleotide sequence of an exemplary oligonucleotide primer that can be employed along with the QIAGEN Universal Reverse Primer in a quantitative PCR (qPCR) reaction of a cre-miR1153-5p.2 (SEQ ID NO: 96) nucleic acid.

SEQ ID NO: 23 is the nucleotide sequence of an exemplary oligonucleotide primer that can be employed along with the QIAGEN Universal Reverse Primer in a quantitative PCR (qPCR) reaction of an ath-miR827 (SEQ ID NO: 81) nucleic acid.

SEQ ID NO: 24 is the nucleotide sequence of an exemplary oligonucleotide primer that can be employed along with the QIAGEN Universal Reverse Primer in a quantitative PCR (qPCR) reaction of an mdo-miR-7267-3p (SEQ ID NO: 129) nucleic acid.

SEQ ID NOs: 25 and 26 are the nucleotide sequences of exemplary oligonucleotides primer that can be employed together in a quantitative PCR (qPCR) reaction of a ycnE nucleic acid.

SEQ ID NOs: 27 and 28 are the nucleotide sequences of exemplary oligonucleotides primer that can be employed together in a quantitative PCR (qPCR) reaction of spaC nucleic acid.

SEQ ID NOs: 29 and 30 are the nucleotide sequences of exemplary oligonucleotides primer that can be employed together in a quantitative PCR (qPCR) reaction of lexA nucleic acid.

SEQ ID NOs: 31 and 32 are the nucleotide sequences of exemplary oligonucleotides primer that can be employed together in a quantitative PCR (qPCR) reaction of a Bacteroidetes-specific nucleic acid.

SEQ ID NOs: 33 and 34 are the nucleotide sequences of exemplary oligonucleotides primer that can be employed together in a quantitative PCR (qPCR) reaction of a Clostridial-specific nucleic acid.

SEQ ID NOs: 35 and 36 are the nucleotide sequences of exemplary oligonucleotides primer that can be employed together in a quantitative PCR (qPCR) reaction of a Bacteria-specific nucleic acid.

SEQ ID NOs: 37 and 38 are the nucleotide sequences of exemplary oligonucleotides primer that can be employed together in a quantitative PCR (qPCR) reaction of a Lactobacilli-specific nucleic acid.

SEQ ID NOs: 39 and 40 are the nucleotide sequences of exemplary oligonucleotides primer that can be employed together in a quantitative PCR (qPCR) reaction of a Enterobacteria-specific nucleic acid.

SEQ ID NOs: 41 and 42 are the nucleotide sequences of exemplary oligonucleotides primer that can be employed together in a quantitative PCR (qPCR) reaction of an LGG-dnaJ-specific nucleic acid.

SEQ ID NOs: 43 and 44 are the nucleotide sequences of exemplary oligonucleotides primer that can be employed together in a quantitative PCR (qPCR) reaction of a Ruminococcaceae-specific nucleic acid.

SEQ ID NOs: 45 and 46 are the nucleotide sequences of exemplary oligonucleotides primer that can be employed together in a quantitative PCR (qPCR) reaction of a universal 16S rRNA.

SEQ ID NOs: 47-164 arfe the nucleotide sequences of exemplary mature miRNAs disclosed herein, particularly those disclosed in the Tables.

DETAILED DESCRIPTION

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC—IUB Commission on Bio-Chemical Nomenclature Symbols for Amino-Acid Derivatives and Peptides, 1972.

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter includes edible plant-derived nanoparticles for regulation of gut microbiota. In some embodiments, a composition is provided that comprises a first edible plant-derived nanoparticle encapsulating an effective amount of RNA. In some embodiments, the RNA encapsulated by the first edible plant-derived nanoparticle is obtained from a second edible-plant derived nanoparticle.

The term "nanoparticle" as used herein in reference to the edible plant-derived nanoparticles of the presently disclosed subject matter, refers to nanoparticles that are in some embodiments in the form of small assemblies of lipid particles, in some embodiments are about 50 to 1000 nm in size, and are not only secreted by many types of in vitro cell cultures and in vivo cells, but are also commonly found in vivo in body fluids, such as blood, urine and malignant ascites. Indeed, such nanoparticles include, but are not limited to, particles such as microvesicles, exosomes, epididimosomes, argosomes, exosome-like vesicles, microparticles, promininosomes, prostasomes, dexosomes, texosomes, dex, tex, archeosomes, and oncosomes.

Such nanoparticles can be formed by a variety of processes, including the release of apoptotic bodies, the budding of microvesicles directly from the cytoplasmic membrane of a cell, and exocytosis from multivesicular bodies. For example, exosomes are commonly formed by their secretion from the endosomal membrane compartments of cells as a consequence of the fusion of multivesicular bodies with the plasma membrane. The multivesicular bodies are formed by inward budding from the endosomal membrane and subsequent pinching off of small vesicles into the luminal space. The internal vesicles present in the multivesicular bodies are then released into the extracellular fluid as so-called exosomes. Nanoparticles can also be engineered to be similar to these isolatable entities.

As part of the formation and release of nanoparticles, unwanted molecules are eliminated from cells. However, cytosolic and plasma membrane proteins are also incorporated during these processes into the microvesicles, resulting in microvesicles having particle size properties, lipid bilayer functional properties, and other unique functional properties that allow the nanoparticles to potentially function as effective nanoparticle carriers of therapeutic agents. In this regard, in some embodiments, the term "nanoparticle" is used interchangeably herein with the terms "microvesicle," "liposome," "exosome," "exosome-like particle," "nanovector" and grammatical variations of each of the foregoing.

The term "edible plant" is used herein to describe organisms from the kingdom Plantae that are capable of producing their own food, at least in part, from inorganic matter through photosynthesis, and that are fit for consumption by a subject, as defined herein below. Such edible plants include, but are not limited to, vegetables, fruits, nuts, and the like. In some embodiments of the nanoparticle compositions described herein, the edible plant is a fruit. In some embodiments, the fruit is selected from a grape, a grapefruit, and a tomato. In some embodiments, the edible plant is selected from a ginger, a grapefruit, and a carrot. In some embodiments, the edible plant is ginger.

The phrases "derived from an edible plant" and "edible plant-derived", when used in the context of a nanoparticle, refers to a nanoparticle that, by the hand of man, exists apart from its native environment and is therefore not a product of nature. In this regard, in some embodiments, the phrase "derived from an edible plant" can be used interchangeably with the phrase "isolated from an edible plant" to describe a nanoparticle of the presently-disclosed subject matter that is useful for encapsulating therapeutic agents. However, in some embodiments the phrases "derived from an edible plant" and "edible plant-derived" refer to a nanoparticle that has been created from total lipids extracted from an isolated planbt derived nanoparticle. In such embodiments, the "edible plant-derived nanoparticle" is a nanoparticle that is constructed to have a particular lipid bilayer composition that is substantially similar to that of an edible plant-derived nanoparticle that can be isolated from an edible plant. As discussed in more detail here below, different edible plant-derived nanoparticles preferentially target different types of bacteria based at least in part on the types of lipids present in their bilayers. By way of example and not limitation, exosome-like nanoparticle (ELNs) derived from ginger (GELNs) or from turmeric (TELNs) have lipid bilayers that are enriched for phosphatidic acids (PAs), primarily 1,2-dilinoleoyl-sn-glycero-3-phosphate, C18:1/C18:3 (36:4) and 1-palmitoyl-2-linoleoyl-sn-glycero-3-phosphate, C16:0/C18:2 (34:2). ELNs from grapefruit and garlic have relatively low levels of PAs (only 3.5% and 5.5%, respectively), with the majority of the lipid in grapefruit (GFELNs) and garlic (GaELNs) being phosphatidylcholine (PC; 36.2% and 52.6%, respectively). Manufactured nanoparticles (also referred to herein as "nanovectors" (NVs)) can be designed to have particular lipid bilayer compositions (including but not limited to enriched for PAs or PC) depending on which bacterial genera are of interest to target. By way of example and not limitation, if the bacteria to be targeted are Lactobacillaceae, an nanovector can be designed to have a bilayer enriched in PA since GELNs and garlic NVs (GNVs) have a bilayer enriched in PA and are been shown to preferentially target Lactobacillaceae. Bacterial genera that are preferentially targeted by GFELNs or GaELNs can also be targeted with NVs that comprise a lipid bilayer enriched for PC. Accordingly, the phrase "edible plant-derived nanoparticle" includes both isolatable nanoparticles as well as manufactured nanoparticles.

The phrase "encapsulated by a nanoparticle," or grammatical variations thereof is used herein to refer to nanoparticles whose lipid bilayer surrounds a therapeutic agent. For example, a reference to "nanoparticle RNA" refers to a nanoparticle whose lipid bilayer encapsulates or surrounds an effective amount of RNA. In some embodiments, the encapsulation of various therapeutic agents within nanoparticles can be achieved by first mixing one or more therapeutic agents with isolated nanoparticles in a suitable buffered solution, such as phosphate-buffered saline (PBS). After a period of incubation sufficient to allow the therapeutic agent to become encapsulated during the incubation period, the nanoparticle/therapeutic agent mixture is then subjected to a sucrose gradient (e.g., an 8, 30, 45, and 60% sucrose gradient) to separate the free therapeutic agent and free microvesicles from the therapeutic agents encapsulated within the microvesicles, and a centrifugation step to isolate the nanoparticles encapsulating the therapeutic agents. After this centrifugation step, the nanoparticles including the therapeutic agents are seen as a band in the sucrose gradient such that they can then be collected, washed, and dissolved in a suitable solution for use as described herein below.

In some embodiments, the effective amount of RNA that is encapsulated by the first edible plant-derived nanoparticle and that is obtained from the second-edible plant derived nanoparticle comprises and effective amount of miRNA. In some embodiments, the miRNA comprises miRNA167a. Of course, microRNAs are naturally occurring, small non-coding RNAs that are about 17 to about 25 nucleotide bases (nt) in length in their biologically active form. miRNAs post-transcriptionally regulate gene expression by repressing target mRNA translation. It is thought that miRNAs function as negative regulators of gene expression and/or of a biological activity of a gene product, i.e. greater amounts of a particular miRNA will correlate with lower levels of target gene expression. There are three forms of miRNAs existing in vivo: primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nt overhang at the 3' end. The cleavage product, the premature miRNA (pre-miRNA) is about 60 to about 110 nt long with a hairpin structure formed in a fold-back manner. Pre-miRNA is transported from the nucleus to the cytoplasm by Ran-GTP and Exportin-5.

Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nt in length.

In some embodiments of the presently disclosed subject matter, a pharmaceutical composition is provided that comprises an edible plant-derived nanoparticle composition disclosed herein and a pharmaceutical vehicle, carrier, or excipient. In some embodiments, the pharmaceutical composition is pharmaceutically-acceptable for use in humans. Also, as described further below, in some embodiments, the pharmaceutical composition can be formulated as a therapeutic composition for delivery to a subject, including but not limited to a human subject.

A pharmaceutical composition as described herein in some embodiments comprises a composition that includes pharmaceutical carrier such as aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The pharmaceutical compositions used can take such forms as suspensions, solutions or emulsions in oily or aqueous vehicles, and can contain formulatory agents such as suspending, stabilizing and/or dispersing agents. Additionally, the formulations can be presented in unit-dose or multi-dose containers, for example sealed ampoules and vials, and can be stored in a frozen or freeze-dried or room temperature (lyophilized) condition requiring only the addition of sterile liquid carrier immediately prior to use.

In some embodiments, solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, but are not limited to, microcrystalline cellulose, corn starch, sodium starch glycolate, and alginic acid. Tablet binders that can be used include acacia, methylcellulose, sodium carboxymethylcellulose, polyvinylpyrrolidone, hydroxypropyl methylcellulose, sucrose, starch, and ethylcellulose. Lubricants that can be used include magnesium stearates, stearic acid, silicone fluid, talc, waxes, oils, and colloidal silica. Further, the solid formulations can be uncoated or they can be coated by known techniques to delay disintegration and absorption in the gastrointestinal tract and thereby provide a sustained/extended action over a longer period of time. For example, glyceryl monostearate or glyceryl distearate can be employed to provide a sustained-/extended-release formulation. Numerous techniques for formulating sustained release preparations are known to those of ordinary skill in the art and can be used in accordance with the present invention, including the techniques described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013; 5,897,876; 5,824,638; 5,464,633; 5,422,123; and 4,839,177; and WO 98/47491, each of which is incorporated herein by this reference.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically-acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of capsules, tablets or lozenges formulated in conventional manner.

Various liquid and powder formulations can also be prepared by conventional methods for inhalation into the lungs of the subject to be treated or for intranasal administration into the nose and sinus cavities of a subject to be treated. For example, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. Capsules and cartridges of, for example, gelatin for use in an inhaler or insufflator may be formulated containing a powder mix of the desired compound and a suitable powder base such as lactose or starch.

The compositions can also be formulated as a preparation for implantation or injection. Thus, for example, the compositions can be formulated with suitable polymeric or hydrophobic materials (e.g., as an emulsion in an acceptable oil) or ion exchange resins, or as sparingly soluble derivatives (e.g., as a sparingly soluble salt).

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol), and the like. For intravenous injections, water soluble versions of the compositions can be administered by the drip method, whereby a formulation including a pharmaceutical composition of the presently-disclosed subject matter and a physiologically-acceptable excipient is infused. Physiologically-acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the composition can be prepared and administered as a suspension in an aqueous base or a pharmaceutically-acceptable oil base, such as an ester of a long chain fatty acid, (e.g., ethyl oleate).

In addition to the formulations described above, the microvesicle compositions of the presently-disclosed subject matter can also be formulated as rectal compositions, such as suppositories or retention enemas, e.g., containing conventional suppository bases such as cocoa butter or other glycerides. Further, the nanoparticle compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt.

Further provided, in some embodiments of the presently-disclosed subject matter, are methods for regulating gut microbiota and/or treating gut dysbiosis that comprise administering to a subject an effective amount of a composition comprising a first edible plant-derived nanoparticle encapsulating an effective amount of RNA, where the RNA is obtained from a second edible-plant derived nanoparticle.

As used herein, the terms "treatment" or "treating" relate to any treatment of a condition of interest (e.g., an inflammatory disorder or a cancer), including but not limited to prophylactic treatment and therapeutic treatment. As such, the terms "treatment" or "treating" include, but are not limited to: preventing a condition of interest or the to development of a condition of interest; inhibiting the progression of a condition of interest; arresting or preventing the further development of a condition of interest; reducing the severity of a condition of interest; ameliorating or relieving symptoms associated with a condition of interest; and causing a regression of a condition of interest or one or more of the symptoms associated with a condition of interest.

For administration of a therapeutic composition as disclosed herein (e.g., an edible plant-derived nanoparticle encapsulating a RNA), conventional methods of extrapolating human dosage based on doses administered to a murine animal model can be carried out using the conversion factor for converting the mouse dosage to human dosage: Dose Human per kg=Dose Mouse per kg/12 (Freireich et al., 1966). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich et al. 1966. Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, intratracheal installation, surgical implantation, transdermal delivery, local injection, intranasal delivery, and hyper-velocity injection/bombardment. Where applicable, continuous infusion can enhance drug accumulation at a target site (see e.g., U.S. Pat. No. 6,180,082).

Regardless of the route of administration, the compositions of the presently-disclosed subject matter are typically administered in amount effective to achieve the desired response. As such, the term "effective amount" is used herein to refer to an amount of the therapeutic composition (e.g., a nanoparticle encapsulating a therapeutic agent, and a pharmaceutically vehicle, carrier, or excipient) sufficient to produce a measurable biological response (e.g., a decrease in inflammation). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. In some embodiments, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Patent Application Publication No. WO 93/25521; Berkow et al., 1997; Goodman et al., 1996; Ebadi, 1998; Katzung, 2001; Remington et al., 1975; Speight et al., 1997; and Duch et al., 1998.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Sambrook et al., 1989 (Chapters 16 and 17); U.S. Pat. No. 4,683,195; Glover & Hames, 1985; Glover & Hames, 1995; Gait, 1984; Hames & Higgins, eds., 1984; Hames & Higgins, eds., 1985; Freshney, 1987; *Immobilized Cells And Enzymes*, IRL Press, 1986; Perbal, 1984; Abelson & Simon, 1988a; Abelson & Simon, 1988b; Miller & Calos, 1987; Mayer & Walker, 1987; Weir et al., 1986.

The presently-disclosed subject matter is further illustrated by the following particular but non-limiting examples.

EXAMPLES

The following EXAMPLES provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Herein is shown that edible plant exosome-like nanoparticles, such as ginger ELN, were taken up by gut bacteria, leading to altering the composition of gut bacteria. It is further demonstrated that edible plant RNAs play a role in the ELN mediated change of composition of gut microbiota. *Lactobacillus rhamnosus* (LGG), a gut bacterium that takes up ginger ELNs (GELNs), was used as a proof-of-concept to study the molecular mechanisms whereby LGG prevents gut inflammation in a mouse colitis model. *Lactobacillus* colonizes gut mucosal sites using pili (fimbriae) to adhere to intestinal epithelial cells. The pili are formed by the polymerization of 3 subunits, SpaA, B, and C (called SpaCBA). SpaC is a key factor for adhesion between LGG and human intestinal mucus (Segers & Lebeer, 2014). Whether the expression of SpaC is regulated by GELN miRNA is not known. While not wishing to be bound by any particular theory of operation, it is hypothesized that GELNs shape gut microbiota and prevent the invasion of gut microbiota via GELN miRNA interaction with gut bacterial mRNA.

Materials and Methods of the EXAMPLES

Mice. Eight- to twelve-week-old male specific-pathogen-free (SPF) C57BL/6 mice and IL-22 knockout mice (C57BL/6-IL-22$^{tm1.1(icre)Stck}$/J) were purchased from the Jackson Laboratory (Bar Harbor, Maine, United States of America). AHR knockout mice were purchased from Taconic Biosciences, Inc. (Rensselaer, New York, United States of America). All mice were housed under specific-pathogen-free conditions. Germ-free mice were purchased from the National Gnotobiotic Rodent Resource Center (University of North Carolina at Chapel Hill, Chapel Hill, North Carolina, United States of America) and maintained in flexible film isolators (Taconic Biosciences, Inc.) at the Clean Mouse Facility of the University of Louisville (Louisville, Kentucky, United States of America). Animal care was performed following the Institute for Laboratory Animal Research (ILAR) guidelines, and all animal experiments were conducted in accordance with protocols approved by the University of Louisville Institutional Animal Care and Use Committee (Louisville, Kentucky, United States of America).

Clinical Samples. The study involved 58 healthy volunteers between the ages of 25 and 46 years (30 males, 28 females) who were randomly assigned to a GELN group (14 males, 14 females) or a control group (16 males, 14 females) using simple randomization (Kim & Shin, 2014). The sample size for human subjects was determined by a one-way ANOVA-based power analysis (http://www.biostathandbook.com/power.html). Given a power of 0.8, effect size of 0.4 and significance level of 0.05, the sample size needed in each group was 25.52458 (rounded=26) and resource equation method (Festing & Altman, 2002). The participants in the two groups were matched for age and gender. All clinical fecal samples from healthy volunteers were collected in the Department of Surgery, Huai'an First People's Hospital, Huai'an, Jiangsu, China with written informed consent from patients. Approval for the study was granted by the Institutional Research Ethics Committee at the Health Department of Huai'an, Jiangsu, China. All subjects provided signed informed consent for participation in the study. Volunteers were recruited from the population in 2017 in Huai'an, Jiangsu, China. No subjects had a history of chronic gastrointestinal disease, antibiotic use within three months prior to testing, alcohol abuse, or smoking. To prevent bias in study results, participants were kept blinded to the allocation. Both researchers and participants were kept blinded to the treatment groups. Before taking GELNs, volunteers provided fecal samples at day 0. Participants drank GELNs in the amount of 200 mg in 10 ml of sterile 0.9% sodium chloride (GELNs group; n=28) or 10 ml of sterile 0.9% sodium chloride only (control group; n=30) on days 2, 4, and 6. The feces of all enrolled subjects were collected at day 7.

Cells. C57BL/6 murine colon adenocarcinoma MC-38 cells (gender unknown; Kerafast, Inc., Boston, Massachusetts, United States of America) or human epithelial colorectal adenocarcinoma Caco-2 cells (male karyotype; American Type Culture Collection, ATCC®, Manassas, Virginia, United States of America) were grown in tissue culture plates with Dulbecco's modified Eagle's medium (DMEM) supplemented with 10% heat-inactivated fetal bovine serum (FBS), 100 U/mL penicillin, and 100 µg/mL streptomycin at 37° C. in a 5% $CO_2$ atmosphere.

Bacteria. *Lactobacillus rhamnosus* (LGG) was obtained from ATCC® (Catalog No. 53103). The SpaC-deleted LGG was cultured in Lysogeny broth (LB; ISC BioExpress, Kaysville, Utah, United States of America) at 37° C. Ruminococcaceae sp. (ATCC® Catalog No. TSD-27) was grown in GS2+cellobiose medium (Biddle et al., 2013). *Listeria monocytogenes* (*Listeria*; ATCC® Catalog No. 15313) and *Bacteroides fragilis* (*Fragilis*, NCTC 9343) were cultured in brain heart infusion (BHI) broth (Hardy Diagnostics, Santa Maria, California, United States of America) as described in Zhang & Wang, 2015 and Deng et al., 2015, respectively. LGG was grown in MRS broth media at 37° C. in anaerobic conditions for 14-16 hours to an $OD_{600}$ of 0.8-1.0. Bacterial viability and concentration were checked by MRS agar platting. Cultures were centrifuged and the bacterial pellet was diluted in MRS for in vitro experiments and in PBS for gavaging at $10^9$ CFU/mouse per day.

Preparation of Plant ELNs. To prepare plant exosome-like nanoparticles (ELNs), peeled Hawaiian ginger roots (Simply ginger, PLU #:4612), carrot, garlic, turmeric roots, and grapefruit were used for isolation and purification of ELNs using a previously described method (Mu et al., 2014). Briefly, the plants listed above were peeled and then homogenized in a high-speed blender for 1 minute. The juice was collected after net filtration. The supernatant was collected after centrifugation at 1,000×g for 10 minutes, 2,000×g for 20 minutes, 4,000×g for 30 minutes, and 10,000×g for 1 hour. The pellets containing nanoparticles derived from each plant were spun down at 100,000×g for 1.5 hours at 4° C. The isolated exosomes were further purified in a sucrose gradient (8, 30, 45, and 60% sucrose in 20 mM Tri-Cl, pH 7.2), followed by centrifugation at 100,000×g for 1.5 hours at 4° C. Purified GELNs were fixed in 2% paraformaldehyde and imaged under a Zeiss EM 900 electron microscope using a previously described method (Mu et al., 2014). The purity of GELNs was evaluated by calculating the ratio of particle to protein (Webber & Clayton, 2013). The size distribution of GELNs was analyzed using a Zetasizer Nano ZS (Malvern Instrument, United Kingdom) at a flow rate of 0.03 ml per minute. The protein concentration of GELNs was determined using a Bio-Rad Protein Quantitation Assay kit with bovine serum albumin as the standard.

RNA Extraction. Total RNA containing miRNA was isolated from ELNs and murine tissue using a miRNeasy mini kit (QIAGEN) according to the manufacturer's instructions. In brief, 50 mg of plant-derived ELNs or tissue was disrupted in QIAzol Lysis Reagent. Tissue was homogenized using a tissue grinder before disruption. The homogenate was mixed with 140 µl of chloroform and centrifuged. The upper aqueous phase was mixed with 1.5 volumes of ethanol and loaded into an RNeasy spin column. The flow-through was discarded after centrifugation, and the column was washed with RWT and RPE sequentially. Total RNA was eluted with RNase-free water. Bacterial mRNA was isolated using RiboPure Bacteria and MICROBExpress kits (Thermo Fisher Scientific) according to the manufacturers' instructions. The quality and quantity of the isolated RNA were analyzed using a NanoDrop spectrophotometer and Agilent Bioanalyzer.

Preparation of Plant Nanovectors. To prepare GELN nanovectors (GNVs) and grapefruit ELN nanovectors (GFNVs), the GELN or grapefruit ELN-derived lipids were extracted with chloroform and dried under vacuum. To generate GNVs and GFNVs, 200 nmol of lipid was suspended in 200-400 µl of 155 mM NaCl with or without 10 µg of ELN-derived RNA. After UV irradiation at 500 mJ/cm$^2$ in a Spectrolinker crosslinker (Spectronic Corp., Westbury, New York, United States of America) and a bath sonication (F S60 bath sonicator; Thermo Fisher Scientific, Hampton, New Hampshire, United States of America) for 30 minutes, the pelleted particles were collected by centrifugation at 100,000×g for 1 hour at 4° C. The RNA encapsulation efficiency of GNVs (68±5%) was determined using a previously described method (Teng et al., 2016).

Plant ELN Distribution in Vivo. Plant ELNs labeled with DiR dye were administered to C57BL/6 mice (n=5) by oral gavage at 500 mg/kg. The labeled plant ELNs in the gut of mice were visualized using an Odyssey CLx Imaging System (LI-COR, Inc., Lincoln, Nebraska, United States of America).

Migration Assays. MC-38 or Caco-2 cells (ATCC) were seeded at 1×10$^5$ cells per well in a 12-well tissue culture plate with Dulbecco's modified Eagle's medium (DMEM) without antibiotics. The cells were inoculated with 1×10$^7$ bacteria per well for 90 minutes at 37° C. in a 5% CO$_2$ atmosphere to allow bacterial adhesion and entry. The number of intracellular bacteria was quantified as described in Zhang & Wang, 1998.

DSS Colitis Model. Colitis was induced by addition of dextran sulfate sodium (DSS; MP Biomedicals, Santa Ana, California, United States of America) to autoclaved drinking water at 2.5%. Colitis development was monitored daily by assessing body weight and presence of blood in the stool.

Bacterial Translocation. Bacterial translocation from the murine gut to peripheral blood and liver was determined at the indicated times presented in the relevant figures after oral bacterial administration. Fifty microliters of anticoagulant blood were cultured on MRS agar for 48 h at 37° C. in an anaerobic chamber. Liver tissue samples were homogenized in 0.5% Triton X-100/PBS, and 100 µl of the homogenates were cultured on MRS agar plates. After 48 hours of incubation, CFUs were counted, and the results are expressed as number of bacteria detected/mL of blood or gram of liver.

Labeling of Bacteria and Nanoparticles. Bacteria, ELNs, or ELN nanovectors were labeled with PKH26 or PKH67 Fluorescent Cell Linker Kits (Sigma-Aldrich Co., St. Louis, Missouri, United States of America) in accordance with the manufacturer's instructions. After a wash with PBS, bacteria pellets, ELNs or ELN nanovectors were suspended in 250-500 µl of diluent C with 2-4 µl of PKH26/67 and subsequently incubated for 30 minutes at room temperature. After centrifugation for 5 minutes at 13,000×g, labeled LGG, ELNs, or ELN nanovectors were resuspended for further use.

Bacteria GELN Uptake Assay. Briefly, 1×10$^7$ LGG cells were incubated for 30 minutes at room temperature with 1 mg of PKH26-labeled GELNs or 1 µg of GELN RNA encapsulated in GNVs. After two washes with PBS, LGG uptake of GELNs was visualized using a confocal microscope. To exclude the possibility of detecting GELNs remaining (adhering) on the outside of bacteria, the bacteria were washed three times with medium and treated with 100 µl of 0.5% Triton X-100 for eight minutes, followed by the immediate addition of bacteria broth to wash bacteria twice before the bacteria were imaged using confocal microscopy. (Note: 0.5% Triton X-100 did not affect bacterial viability for at least 30 minutes after addition).

Immunogold Labeling of LGG Pili and TEM. To visualize LGG pili via transmission electron microscopy (TEM), LGG cultures were grown overnight (OD$_{600}$<1.0) and washed once with PBS. Formvar-carbon-coated copper grids (Electron Microscopy Sciences, Hatfield, Pennsylvania, United States of America) first were floated for 1 hour on droplets of the diluted LGG at 10$^7$/mL in PBS, washed several times with 0.02 M glycine in PBS, and then treated with a blocking solution of 1% bovine serum albumin (BSA) in PBS. The grids were then floated for 1 hour on droplets of anti-SpaC serum (1:100) in blocking solution. After a wash with 0.1% BSA in PBS, the grids were incubated for 20 minutes with protein A-conjugated 10-nm-diameter gold particles (Cytodiagnostics, Burlington, Ontario, Canada) diluted 1:55 in blocking solution. After one wash in PBS, the grids were fixed with 1% glutaraldehyde, washed with distilled water, and then stained with 1% ammonium molybdate on the surface of the EM grid. After excess ammonium molybdate was removed from the grid, images were visualized using a Thermo-Fisher TEM Tecnai Spirit at 80 kV, and images were collected with an AMT XR60 digital camera.

Quantitative Real-Time PCR for RNA Expression. The quantity of mature miRNAs was determined with quantitative real-time PCR (qPCR) using a miScript II RT kit (QIAGEN Inc., Germantown, Maryland, United States of America) and miScript SYBR Green PCR Kit (QIAGEN) with QIAGEN 3' universal primers. The 5' specific miRNA primers used are listed in Table 1. For analysis of gene mRNA expression, 1 µg of total RNA was reverse transcribed using SuperScript III reverse transcriptase (Invitrogen, Waltham, Massachusetts, United States of America), and quantitation was performed using SsoAdvanced™ Universal SYBR Green Supermix (Bio-Rad Laboratories, Inc., Hercules, California, United States of America) and the listed primers (Table 1) with SsoAdvanced™ Universal SYBR Green Supermix (Bio-Rad). qPCR was performed using a Bio-Rad CFX96 qPCR System with each reaction run in triplicate. Analysis and fold-changes were determined using the comparative threshold cycle (Ct) method. Changes in miRNA or mRNA expression were calculated as fold-change.

Quantification of Gut Bacteria Using QPCR. For gut bacteria identification, qPCR was performed from gut microbiota-derived DNA extracted with a QIAamp DNA Stool Mini Kit (QIAGEN). All kits were used according to the manufacturer's instructions. Quantitation was performed using SsoAdvanced™ Universal SYBR Green Supermix (Bio-Rad), and the bacterial specific primers are listed in Table 1. qPCR was performed using the Bio-Rad CFX96 qPCR System with each reaction run in triplicate. Analysis and fold-change were determined using the comparative threshold cycle (Ct) method.

Plasmid Construction and Mutagenesis. The SpaC fragment (339-800, LGG RS02140) spanning the sequences of the potential target (710-717) of GELN ath-miR167a was obtained by PCR with cDNA from LGG RNA. PCR was performed using a Bio-Rad thermal cycler T100. The 462-bp PCR product amplified by the primer pair SpaC-pGFPuv-F: 5'-GCGCATGCCTGCAACTAATTTTGTCGCAAACG-3' (SEQ ID NO: 1) and SpaC-pGFPuv-R: 5'-CCTCTAGAACAGTTTTCAGCAGGCATCC-3' (SEQ ID NO: 2) was ligated into the Sphl and Xbal restriction enzyme sites of a pGFPuv vector (Takara Bio/Clontech, Mountain View, California, United States of America) to obtain a green fluorescent protein (GFP) expression reporter. SpaC-pGFPuv fused with the SpaC gene fragment, which can be expressed in prokaryotic cells. To generate mutants of SpaC, the oligonucleotide primers SpaCMut-F, 5'-CTGTAGGTGCTGTAACTGCCTGAATA CCGTAATAC-3' (SEQ ID NO: 3), and SpaCMut-R, 5'-GT-ATTACGGTATTCAGGCAG TTACAGCACCTACAG-3' (SEQ ID NO: 4), were designed to specifically disrupt the putative ath-miR167a binding site. A GENEART® brand Site-Directed Mutagenesis System (#A13282, Invitrogen) was used in conjunction with specific primers to introduce a SpaC mutation in the pGFPuv construct according to the manufacturer's instructions. After mutant strand synthesis (using T4 DNA polymerase) and ligation, the resultant plasmids were introduced into *E. coli*, and transformants were selected using ampicillin resistance. Further restriction endonuclease Sphl and Xbal analysis was performed to screen clones, and all of the constructs were confirmed by DNA sequencing.

Microbiota 16S rRNA Gene Sequencing. GELNs were administered by gavage to C57BL/6 mice (500 mg/kg of body weight) three times in seven days (n=5). To identify bacterial strains that preferentially take up GELNs, PKH26-labeled GELNs were administered by gavage, and PKH26-positive microbiota from fecal samples were sorted using a BD FACSARIA™ III brand cell sorter (BD Biosciences, San Jose, California, United States of America). Bacterial DNA from fecal samples was isolated with QIAamp DNA Stool Mini Kits (QIAGEN), and bacterial strains were investigated using 16S rRNA gene sequencing. DNA (15 ng) was used as a template to amplify the 16S rRNA gene using a High Fidelity PCR system kit (Roche Molecular Systems, Inc., Branchburg, New Jersey, United States of America). The v1-v3 regions of 16S ribosomal RNA gene were amplified using 27f (5'-AGAGTTTGATCCTGGCTCAG-3'; SEQ ID NO: 5) and 534r (5'-ATTACCGCGGCTGCTGG-3'; SEQ ID NO: 6) primers (1 µM). The primers were anchored with adaptors (adapter A: 5'-CCATCT-CATCCCTGCGTGTCTCCGACTCAG-3'; SEQ ID NO: 7 and adapter B: 5'-CC-TATCCCCTGTGTGCCTTGGCAGTCTCAG-3'; SEQ ID NO: 8) and Multiplex Identifiers (MIDs; 10 bp long). The multiplexed amplicons were purified using a QIAquick Gel Extraction Kit (QIAGEN). The amplicon sequence was conducted using the 454 Jr. Sequencing platform. The 16S rRNA gene sequences were analyzed using QIIME platform scripts (www.qiime.org). The microbial classification was performed with the GreenGenes reference database (Version gg_otus-13_8; The Greengenes Database Consortium, Second Genome, Inc., University of Colorado, Boulder, Colorado, United States of America, University of Queensland, Brisbane, Australia) using QIIME tools (Caporaso et al., 2010a). By applying hierarchical clustering algorithms (HCAs), the species clustering based on the operational taxonomic unit (OTU) using amplicon sequencing of 16S RNA was determined. The reference sequences allowed sorting of the results into OTUs by clustering 97% sequence similarity (uclust) and classification according to various taxonomic ranks (phylum, order, class, family, genus, and species). The percentage of each bacterial species was virtualized with Interactive Tree Of Life (iTOL) and R software (Letunic & Bork, 2007).

Mouse Cytokine Array. To investigate effects of GELN RNAs on the regulation of cytokine expression in colon epithelia, germ-free mice with DSS-induced colitis were administered $10^9$ LGG pretreated with GNVs or GNVs with GELN RNAs. The colon tissue extracts were prepared in modified radioimmunoprecipitation assay (RIPA) buffer (Sigma) with the addition of protease and phosphatase inhibitors (Roche). Cytokine proteins were analyzed with a Proteome Profiler Mouse XL Cytokine Array Kit (Catalog No. ARY028; R&D Systems, Inc., Minneapolis, Minnesota, United States of America). Quantification of the spot intensity in the arrays was conducted with background subtraction using ImageJ.

Proteomic LGG Sample Preparation. Briefly, $1\times10^7$ LGG were incubated with 1 mg GELNs for 2 hours and then harvested by centrifugation at 13,000×g for 5 minutes. Bacteria were suspended in lysis buffer (2% SDS, 100 mM DTT, 20 mM Tris-HCl pH 8.8) for 20 minutes at 95° C. LGG lysate was collected from supernatants after centrifugation, and concentrations were estimated using an RC DC Protein Assay Kit (Bio-Rad). Protein aliquots (50 µg) were diluted into 4% SDS/0.1 M Tris-HCl pH 8.5 and 1 M DTT and processed according to the filter-aided sample preparation (FASP) method as described in Teng et al., 2017. The digested, ultrafiltered samples were trap-cleaned with C18 PROTO™, 300 Å Ultra MicroSpin columns; lyophilized by vacuum centrifugation; and redissolved in 16 µl of 2% v/v acetonitrile. Concentrations were estimated based on absorption at 205 nm using a NanoDrop 2000 spectrophotometer (Thermo Fisher Scientific, San Jose, California, United States of America).

LC-MS Analysis of LGG Protein. Liquid chromatography-mass spectrometry (LC-MS) was carried out using a method described in Teng et al., 2017. Proteome Discoverer v1.4.1.114 (Thermo) was used to analyze the data collected by MS. The database used in Mascot v2.5.1 and SequestHT searches was the Feb. 17, 2017 version of the LGG proteome from UniprotKB (Proteome ID UP000000955; https://www.uniprot.org). Scaffold was used to calculate the false discovery rate using the Peptide and Protein Prophet algorithms. Proteins were grouped to satisfy the parsimony principle. The proteins were clustered based on differential expression, and heat maps representing differentially regulated proteins by GELNs were generated using R software.

Coomassie Blue Staining. The LGG proteins were separated on a 10% SDS-PAGE gel. The gel was fixed and stained for imaging using 0.1% Coomassie Brilliant Blue R-250 (Bio-Rad).

Western Blotting. LGG cells were treated as indicated in each individual Figure and harvested from 100-350 ml cultures by centrifugation at 5,000×g for 10 minutes. The cells were resuspended on ice for 45 minutes in 1 ml of TE buffer (100 mM Tris-Cl, 10 mM EDTA, pH 8.0) supplemented with protease inhibitor cocktail (Roche) and lysozyme (1 mg/mL). The cell lysates were sonicated on ice using three 10-second bursts at medium intensity and then frozen in liquid nitrogen. The lysates were quickly thawed at 37° C., and two more rapid sonication-freeze-thaw cycles were performed. Proteins were separated on 10% SDS-PAGE gels and transferred to PVDF membranes (Bio-Rad Laboratories, Inc., Hercules, California). Mouse anti-SpaC antibody was purchased from PodiCeps (Catalog No. PODI-0063, Netherland) and anti-DnaK antibody was purchased from Abcam (Catalog No. ab69617; Cambridge, Massachusetts, United States of America). After the Alexa Fluor-647 (Invitrogen) conjugated secondary antibody incubation, the bands were visualized and analyzed using an Odyssey Imager (LI-COR, Lincoln, Nebraska, United States of America). For immunoblotting of tissue, mice were treated as indicated in the figure legends, and lysates were prepared in modified RIPA buffer (Sigma) with the addition of protease and phosphatase inhibitors (Roche). Proteins were separated on 10% SDS-PAGE gels and transferred to PVDF membranes (Bio-Rad Laboratories, Inc.). Dual-color precision protein MW markers (Bio-Rad) were separated in parallel. Antibodies were purchased as follows: AHR (PAS-25447) and phosphorylated AHR (PAS-38404) antibodies from Thermo Fisher, CYP1A1 (ab79819) and GAPDH (ab9485) antibodies from Abcam. The secondary antibodies conjugated to Alex Fluor-488 or Alex Fluor-594 were purchased from Invitrogen (Eugene, Oregon, United States of America). The bands were visualized using an Odyssey Imager (LI-COR).

GELN RNA Libraries and Sequencing. Small RNA libraries were generated with 100 ng of total RNA and TruSeq Small RNA Library Preparation Kits (Illumina, Inc., San Diego, California, United States of America) according to the manufacturer's instructions. Following PCR amplification (16 cycles), libraries between 140 and 160 bp in size were gel purified and resuspended in 11 µl of ultrapure water. Equal amounts of libraries were pooled and sequenced on the Illumina HiSeq 2500, followed by demultiplexing and fastq generation with CASAVA v1.8.4. Raw fastqs were adapter and quality score trimmed with cutadapt v1.10. with a minimum length of 15 nt. MicroRNAs were identified using sRNABench Pipeline software (version 05/14). A core set of plant miRNAs from miRBase v21 were used as the reference, and this set included all 14 plant species with at least 200 mature microRNA sequences annotated in miRBase. Within the sRNABench pipeline, mapping was performed with bowtie software (v0.12.9), and microRNA folding was predicted with RNAfold from the Vienna package (v2.1.6).

LGG mRNA Sequencing. LGG cells were treated with fluorescent dye PKH26-labeled GELNs or PBS as indicated in the individual figure legends and harvested from 100-350 ml cultures by centrifugation at 4000×g for 10 minutes. PKH26-positive LGG were sorted with FACS. mRNA was isolated from bacteria using RiboPure Bacteria and MICROBExpress (Thermo Fisher Scientific). For each RNA sample, double-stranded cDNA was synthesized from 10 ng mRNA using a SMARTer Universal Low Input RNA Kit (Catalog No. 634940; Takara Bio Inc., Mountain View, California, United States of America) for sequencing, which included a 16-cycle PCR. Following quantitation with Qubit dsDNA HS Reagent (Catalog No., Q32854; Thermo Scientific,), 10 ng of dscDNA/sample was fragmented with an E220 Focused-ultrasonicator (Covaris, Matthews, North Carolina, United States of America). The fragmented cDNA was then prepared into libraries using a KAPA Hyper Prep Kit (Catalog NO. KK8504; KAPA Biosystems, Wilmington, Massachusetts, United States of America). Libraries were then combined into equimolar pools, which were then measured for size and concentration. The pools were clustered onto a paired-end flowcell with a 20% v/v PhiX spike-in and sequenced on an Illumina HighSeq 2500 sequencer. The first and second reads were each 83 bases.

Species Alignment and Analysis. The mRNA sequencing data were demultiplexed and converted to fastqs with CASAVA v1.8.4, and 7 nt were trimmed from R1 and R2 raw fastqs with cutadapt v1.10 as recommended by the SMARTer kit. Transcript abundance was estimated with salmon v7.2 with the following options: -libType A -num, Bootstraps 100, -seqBias -gcBias -dumpEq -geneMap. For LGG abundance, the transcriptome fasta and annotation from EnsemblBacteria (Genome Assembly ASM2650v1) were used. For *Zingiber officinale* (ginger) abundance, the ESTs from NCBI were used as transcriptome input for salmon. Ginger transcript sequence similarity was determined using NCBI blast v.2.2.26, keeping the top hit against the nucleotide (nt) database with a maximum e-value of 0.001.

Predicting GELN miRNA Targeting to LGG mRNA. After downloading eleven gut bacterial genomes from the RefSeq database available from the website of the National Center for Biotecnology Information (NCBI; U.S. National Library of Medicine, Bethesda Maryland, United States of America), bacterial mRNAs potentially targeted by ginger miRNAs were identified by enrichment analysis of the reverse complement of the miRNA seed sequence in the 300 bp region near the coding sequence (CDS) start site (200 bp before and 100 bp after the site). For the enrichment analysis, two seed subsequences were used: a 7-mer (nt 2-8) and an 8-mer (nt 1-8). The enrichment analysis adopted a framework that utilizes the $1^{st}$ order Markov model (MM). In this framework, the observed k-mer count in the 300-bp region of each bacterial mRNA was compared against the background count derived from the 1' order Markov model. A P-value was then calculated for each miRNA-mRNA pair to estimate the likelihood of having a functional pair. Once all p-values were calculated, the false discovery rate (FDR) was obtained using the Benjamini-Hochberg method (Benjamini & Hochberg, 1995) for multiple P-value correction.

Microbial DNA QPCR Arrays. To determine whether ELN RNA has an effect on the composition of major gut microbial species, mice were gavaged with GELN RNAs and grapefruit and carrot ELN RNAs encapsulated in the GELN lipid-derived liposomes (GNVs; 500 mg/kg mouse weight in 100 µl PBS; n=5). The GNVs were given to mice once every other day for seven days. Three hours after the last dose, the mice were sacrificed, fecal DNA was extracted, and a qPCR array was performed using QIAGEN Custom Microbial DNA qPCR Arrays (Catalog No. 330161) on an Applied Biosystems VIIA™ 7 Real-Time PCR System. Normalization to Pan Bacteria (QIAGEN Catalog No. BPCL00362A) was performed using a threshold cycle (Ct) to correct for potential DNA input or RT efficiency biases. DNA qPCR array data generated from the fecal samples were analyzed using SPSS 16.0 software and are based on fold-changes compared with PBS as a control. Heat maps generated from qPCR data using software R reflect the abundance of the microbial species analyzed.

Thin-Layer Chromatography (TLC) Analysis. Lipids from ELNs were extracted and quantitatively analyzed using a method previously described (Wang et al., 2013). TLC was performed (Zhuang et al., 2015). Briefly, HPTLC-plates (silica gel 60 with a concentrating zone, 20 cm×10 cm; Merck KGaA, Darmstadt, Germany) were used for the separation. After aliquots of concentrated lipid samples were extracted from plant ELNs, they were separated on a plate that had been developed with chloroform/methanol/acetic acid (190:9:1, by vol). After drying in air, the plates were sprayed with a 10% copper sulfate and 8% phosphoric acid solution and then charred by heating at 180° C. for 5 min. The bands of lipid on the plate were imaged using an Odyssey Scanner (LI-COR).

Lipidomic Analysis with Mass Spectrometry. Lipid samples extracted from ELNs were submitted to the Lipidomics Research Center, Kansas State University (Manhattan, Kansas, United States of America) for analysis using a method previously described. In brief, the lipid composition was determined using triple quadrupole MS (Applied Biosystems Q-TRAP, Applied Biosystems, Foster City, California, United States of America). The protocol follows was as described in Wang et al., 2013. The data are reported as the concentration (nmol/mg ELNs) and percentage of each lipid within the total signal for the molecular species determined after normalization of the signals to internal standards of the same lipid class.

Histological Analysis. For hematoxylin and eosin (H&E) staining, tissues were fixed with buffered 10% formalin solution (SF93-20; Fisher Scientific, Fair Lawn, New Jersey, United States of America) overnight at 4° C. Dehydration was achieved by sequential immersion in a graded ethanol series of 70%, 80%, 95%, and 100% ethanol for 40 minutes each. Tissues were embedded in paraffin and subsequently cut into ultrathin slices (5 µm) using a microtome. Tissue sections were deparaffinized in xylene (Fisher), rehydrated in decreasing concentrations of ethanol in PBS, and stained with H&E, and the slides were scanned with an Aperio ScanScope. For frozen sections, tissues were fixed with periodate-lysine-paraformaldehyde (PLP) and dehydrated with 30% sucrose in PBS overnight at 4° C., and nuclei were stained with 4',6-diamidino-2-phenylindole dihydrochloride (DAPI). The slides were scanned using an Aperio ScanScope or visualized via confocal laser scanning microscopy (Nikon, Melville, New York, United States of America) as described in Teng et al., 2017.

HPLC Analysis of Tryptophan Metabolites. The fecal samples and LGG MRS broth were diluted with an equal volume of methanol. After centrifugation at 10,000×g for 30 minutes, 50 µl of supernatant was injected for high-performance liquid chromatography (HPLC) analysis. The HPLC analysis was performed on an Agilent 1260 Infinity system equipped with an Agilent ZORBAX SB-C18 column (4.6× 150 mm, 3.5 µm), with following parameters: mobile phase A: 5 mM $NH_4Ac$ in water modified with 0.1% formic acid (v/v); mobile phase B: 5 mM $NH_4Ac$ in 90% acetonitrile modified with 0.1% formic acid (v/v); gradient: 5% B in first 5 min, 5-20% B for 10 min, hold 20% B for 5 min, 20%-50% B for 5 min, hold 50% B for 5 min, 50%-100% B for 5 min, hold 100% B for 10 min, 100-5% B for 5 min; flow rate: 1.0 ml/min; temperature: 30° C. UV detection at 300 nm was used to monitor indole-3-carboxaldehyde (I3A) and indole-3-acetaldehyde (IAAld); FLD (ex=280 nm; em=350 nm) was used for detection of tryptophan and indole-3-acetamide (I3AM). The standard for I3A (Catalog No. 129445-5g), I3AM (Catalog No. 286281-1G), IAAld (Catalog No. I1000-25MG), and tryptophan (Catalog No. T0254-25g) were purchased from Sigma.

Enzyme-Linked Immunosorbent Assay (ELISA). The cytokine IL-22, IL-1β, and TNFα levels in cell culture supernatants or mouse colon mucus were quantified using ELISA kits (eBioscience) according to the manufacturer's instructions. Briefly, a microtiter plate was coated with anti-mouse IL-22, IL-1β and TNFα antibody at 1:200 overnight at 4° C. Excess binding sites were blocked with 200 µl of 1×ELISA/ELISPoT Diluent (eBioscience, San Diego, California, United States of America) for 1 hour at 22° C. After washing three times with PBS containing 0.05% Tween 20, the plate was incubated with detection antibody in blocking buffer for 1 hour at 22° C. After three washes, avidin conjugated with horseradish peroxidase and substrate were each added sequentially for 1 hour and 30 min at 22° C. An analysis of absorbance at 405 nm using a microtiter plate reader (BioTek Synergy HT, BioTek Instruments, Inc., Winooski, Vermont, United States of America) followed.

Isolation of Lymphoid Cells in the Colon. Intestinal lymphoid cells were isolated from the intestine by incubation in PBS supplemented with 1 mM EDTA, 15 mM HEPES and 10% FCS for 30 minutes at 37° C. Supernatants were discarded, and tissues were then incubated in RPMI supplemented with 15 mM HEPES and 300 units/mL collagenase type VIII (Sigma) for 30 minutes with gentle shaking. Lysates were gently pressed through nylon cell strainers (70 µm in diameter; Fisher Scientific), and mononuclear cells were isolated on a 40%/80% colloidal silica particle (Percoll) gradient. Lymphocytes were recovered from the interface and washed twice.

Antibiotic Treatment. Six- to eight-week-old male mice were provided sterile drinking water supplemented with vancomycin (0.5 mg/mL), streptomycin (1 mg/mL), neomycin (1 mg/mL), chloramphenicol (0.5 mg/mL) or metronidazole (1 mg/mL) for 3 weeks before the beginning of GELN or GNV treatment.

Flow Cytometry. Isolated lymphocytes from colon tissue were seeded into 6-well plates and stimulated for 6 hours with LPS (10 µg/mL) in the presence of brefeldin A (5 µg/mL; Invitrogen). Washed cells were stained for 40 minutes at 4° C. with the appropriate fluorochrome-conjugated antibodies in PBS with 2% FBS. Characterization and phenotyping of the various lymphocyte subsets from the liver or spleen were performed using flow cytometry. Data were acquired using a BD FACSCalibur flow cytometer (BD Biosciences, San Jose, California, United States of America) and analyzed using FlowJo software (Tree Star Inc., Ashland, Oregon, United States of America). To visualize bacteria stained with PKH26/67 and transformed with SpaC-pGFPuv plasmid, the PKH26/67-positive and GFP-positive bacteria were detected by flow cytometry using a BD FACSCalibur flow cytometer (BD Biosciences, San Jose, California, United States of America), and data were analyzed using FlowJo software (Tree Star Inc., Ashland, Oregon, United States of America).

In Vivo Intestinal Permeability Assay. For in vivo intestinal permeability studies, fluorescein-5-isothiocyanate (FITC)-conjugated dextran (MW 4000; Sigma-Aldrich, St. Louis, Missouri, United States of America) was administered by oral gavage at a concentration of 60 mg/100 g of body weight. Serum was collected retro-orbitally five hours later, and fluorescence intensity was determined with a fluorescence spectrophotometer (BioTek) at emission and excitation wavelengths of 485 nm and 528 nm, respectively. FITC concentration was measured from standard curves generated by serial dilution of FITC-dextran.

Quantification and Statistical Analysis. Unless otherwise indicated, all statistical analyses in this study were performed with SPSS 16.0 software. The data are presented as values with standard deviation (as the mean±SD). The significance of differences in mean values between two groups was analyzed using Student's t-test. Differences between individual groups were analyzed via one- or two-way ANOVA. Differences between percentages of bacterial composition were analyzed with a chi-square test. Differences were considered significant when the P-value was less than 0.05 or 0.01. A P value greater than 0.05 was considered not significant (NS). Both animals and human subjects were randomly assigned to a control group and different experimental condition groups matched for age and gender using simple randomization. Double-blinded studies were used for animal and human subject studies. Unless otherwise indicated, the mice used in the in vivo study were male C57BL/6 strain mice. Using one-way ANOVA comparing up to four groups, for a power of 0.7, a large effect size (0.75) and a significance level of 0.05, the minimum sample size needed in each group was 4.992 (rounded=5; Festing & Altman, 2002). The reported "n" in animal and human studies represents the number of animals and human subjects. Data are representative of three independent experiments.

Example 1

GELN RNA Modified Gut Microbiota

Figure 1:
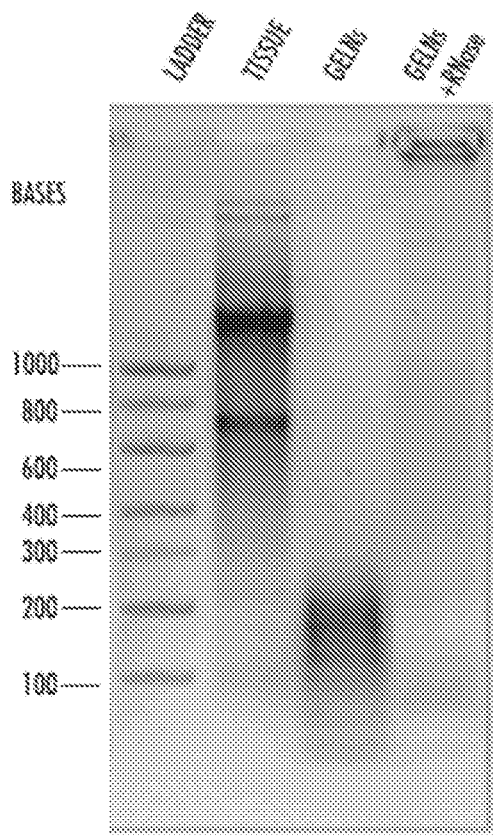
FIG. 1 is a photograph of an ethidium bromide-stained 12% polyacrylamide gel upon which RNA from GELNs pretreated with and without RNase were separated.

A number of edible nanoparticles have been characterized based on electron microscopy (EM) examination (Mu et al., 2014). GELNs were characterized based on size distribution (Mu et al., 2014) and the RNAs and proteins present. Gel electrophoresis demonstrated the presence of substantial amounts of small-sized RNAs (less than 300 nucleotides; FIG. 1). The number of GELNs per gram of ginger tissue ($4.5 \times 10^9$) and yield of GELN RNA per mg of GELNs (1.3 µg/mg) were also quantitatively analyzed. The purity of GELN preparations was determined by comparing the ratio of GELN counts to protein concentration ($1.4 \times 10"$). Next-generation sequencing analysis of GELN RNA (Table 2) further suggested that GELNs contained miRNAs. At a sequencing depth of 20 million reads, 93,679 of the miRNA reads were mapped to 109 mature miRNAs from the NCBI plant miRNA database (Table 2). A number of bacterial mRNAs that could be potentially bound by a seed sequence (7-8 NTs) of GELN miRNAs are listed in Table 3.

Figure 2:
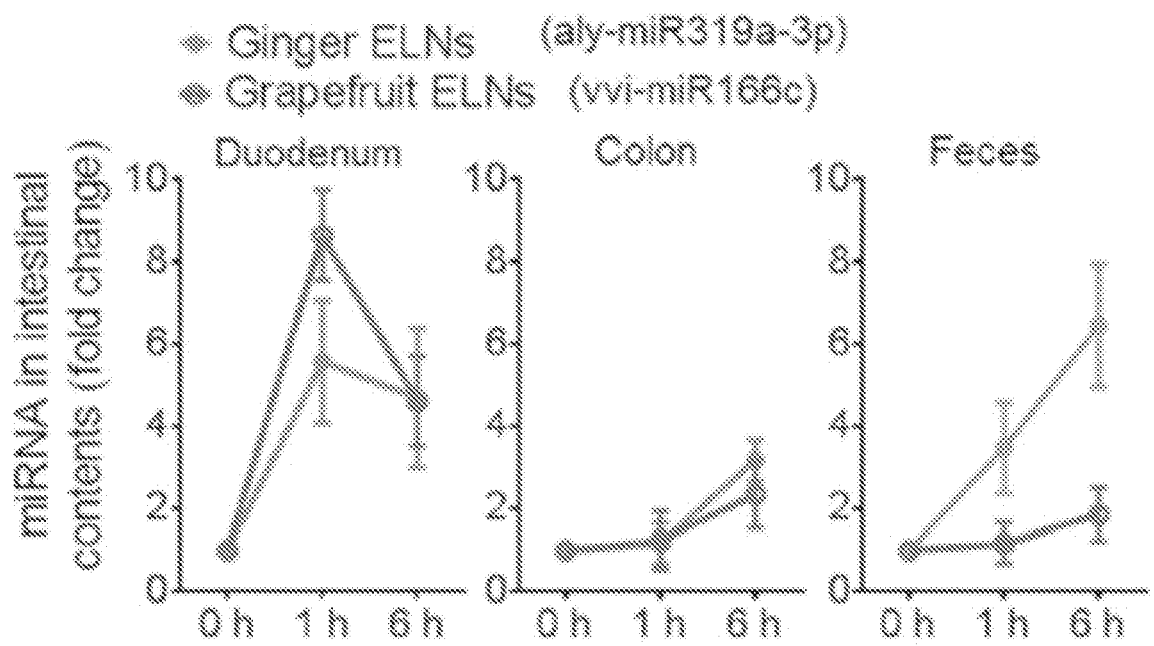
FIG. 2 is a series of graphs of expression of GELN aly-miR319a-3p (SEQ ID NO: 65) and vvi-miR166c (SEQ ID NO: 158) in duodenum, colon, and feces from C57BL/6 mice receiving a single gavage of 10 mg of GELNs or grapefruit ELNs, respectively, at 0 hours, 1 hour, and 6 hours assessed by qPCR.
Figure 3:
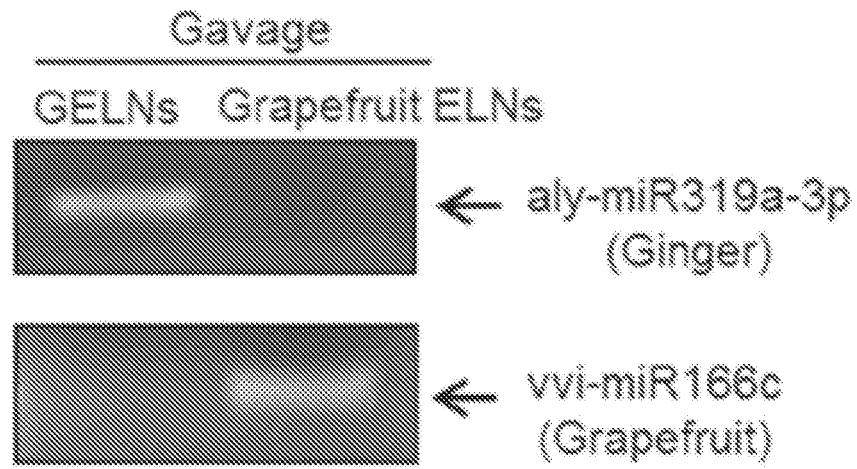
FIG. 3 is a photograph of 2% agarose gel electrophoresis of qPCR analysis for aly-miR319a-3p (SEQ ID NO: 65) and vvi-miR166c (SEQ ID NO: 158) in feces from C57BL/6 mice (n=5) following 10 mg of GELNs or grapefruit ELNs, respectively, at 1 hour.

ELN RNA stability in the gut is required for potential interaction of ELN RNA with gut bacterial mRNA. Analysis of the tissue distribution of ELNs indicated that grapefruit ELNs preferentially migrated to the liver, but GELNs were more likely to stay in the intestine. The evidence of GELNs in the gut and feces over a 6-hour period was further confirmed by quantitative PCR (qPCR) analysis of GELN miRNA aly-miR319a-3p and grapefruit miRNA vvi-miR166c (FIG. 2). The PCR results (FIG. 3) indicated that in fewer than 30 PCR cycles, only aly-miR319a was detected in the feces of mice fed GELNs, whereas vvi-miR166c was only detected in the feces of mice fed with grapefruit ELNs, suggesting that qPCR analysis of fecal samples provided a specific and sensitive approach to investigating the stability of ELNs in the gut.

Figure 4:
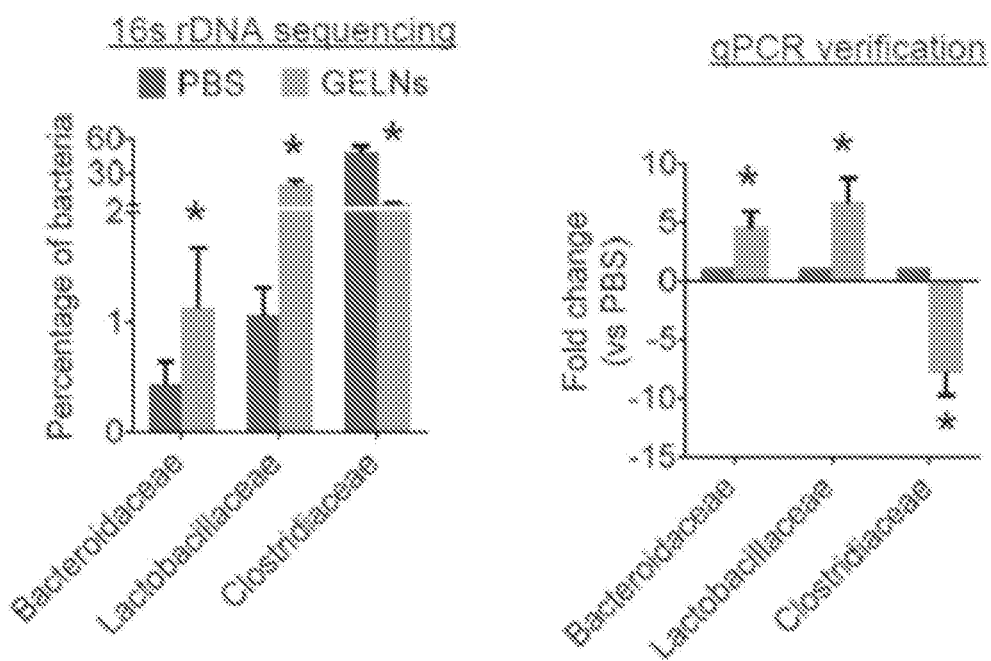
FIG. 4 is a pair of bar graphs for selected bacteria identified by qPCR in feces of mice. Sequencing results (left panel); qPCR results (right panel); GELNs vs PBS, *p<0.05.

Whether GELNs cross-talked with gut microbiota and regulated their composition was thus tested. Fecal samples from C57BL/6 mice that were administered GELNs for a week were collected and the microbial composition was analyzed via 16S rRNA gene (v1-v3 regions) sequencing (the sequencing data were deposited in NCBI Sequence Read Archive (SRA); Accession Number SRP121341). Further downstream analysis was performed using QIIME 1.9.1 pipeline tools (Caporaso et al., 2010). Microbial alignment and classification was performed using the Green Genes reference database (Version gg_13_8_otus) as described herein above. An increase in Lactobacillaceae and Bacteroidales S24-7 and a decrease in Clostridiaceae was observed in GELN-treated mice in comparison with mice treated with PBS. The Lactobacillaceae percentage increased from 0.25±0.15% to 24.80±5.41% (p<0.001) in mice that received GELNs by gavage. The sequencing data were subsequently verified using a qPCR assay (FIG. 4).

Figure 5:
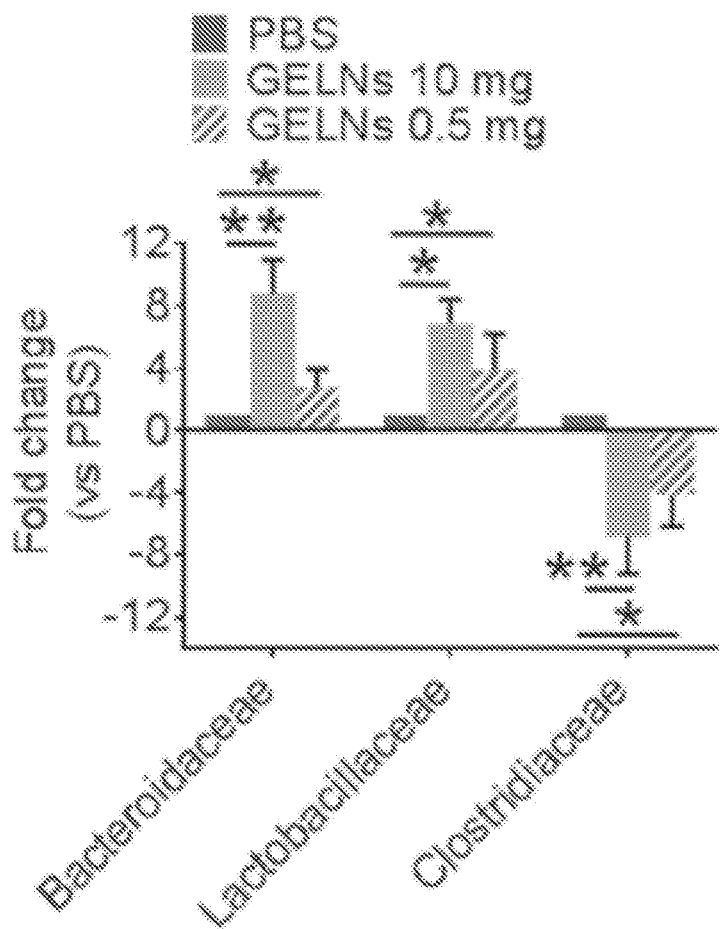
FIG. 5 is a bar graph of the results of 10 mg and 0.5 mg of GELNs or PBS as control fed to C57BL/6 mice (n=5 mice per group) every other day for a total of 3 times. Selected bacteria in feces of C57BL/6 mice treated with PBS and GELNs were identified by qPCR.
Figure 6:
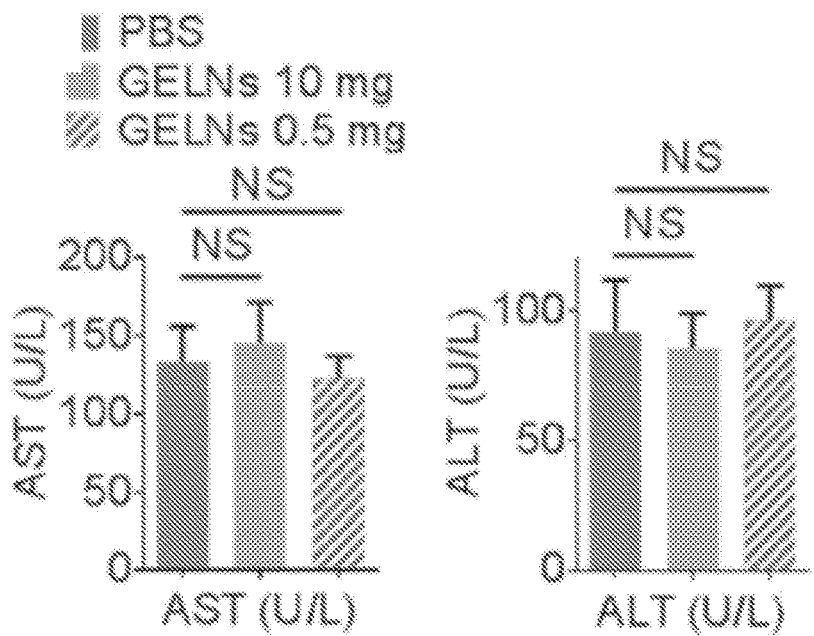
FIG. 6 is a pair of bar graphs showing the results of analysis of AST and ALT in serum of mice. GELNs vs PBS, *p<0.05 by two-tailed t-test; NS, not significant. Data are representative of three independent experiments (error bars, SD).

The effect of GELNs at a high dose of 10 mg/25 g of body weight and at a low dose of 0.5 mg/25 g of body weight (a physiologically relevant dose for human intake; Schwertner et al., 2006) on the composition of gut bacteria was determined. The results generated from both higher and lower doses of GELNs supported the conclusion that GELN treatment increases Lactobacillaceae and Bacteroidaceae and decreases Clostridiaceae compared with PBS (FIG. 5). Neither the higher nor lower doses of GELNs induced any abnormalities in treated mice compared with PBS control mice as determined by serum levels of alanine aminotransferase (ALT) and aspartate aminotransferase (AST; FIG. 6).

To address whether ELN RNAs influenced gut microbiota composition, ELN RNAs from ginger, grapefruit, and carrot were extracted from purified ELNs and encapsulated in GELN nanovectors (GNVs) made with GELN-derived lipid. The results indicated that the mice gavaged with ginger, grapefruit, or carrot ELN RNAs exhibited a change in the composition of gut microbiota, which suggested that edible plant ELN RNAs had an effect on the gut microbiota composition in general. The data from a heat map depicting the mouse gut microbiota using a qPCR array also supported the finding that GELNs shaped gut microbiota. Ginger ELN RNAs induced several species of *Lactobacillus* identical to GELNs when compared with GNVs as a control. However, carrot ELN RNAs seem to have no effect on the *Lactobacillus* level. Cluster analysis using R software (Rosselli et al., 2016) indicated that PBS and GNVs were grouped in the same cluster, GNVs/grapefruit ELN RNAs and GNVs/carrot ELN RNAs were in the same cluster, and GNVs/GELN-RNAs had the least similarity with the other two clusters.

Figure 7:
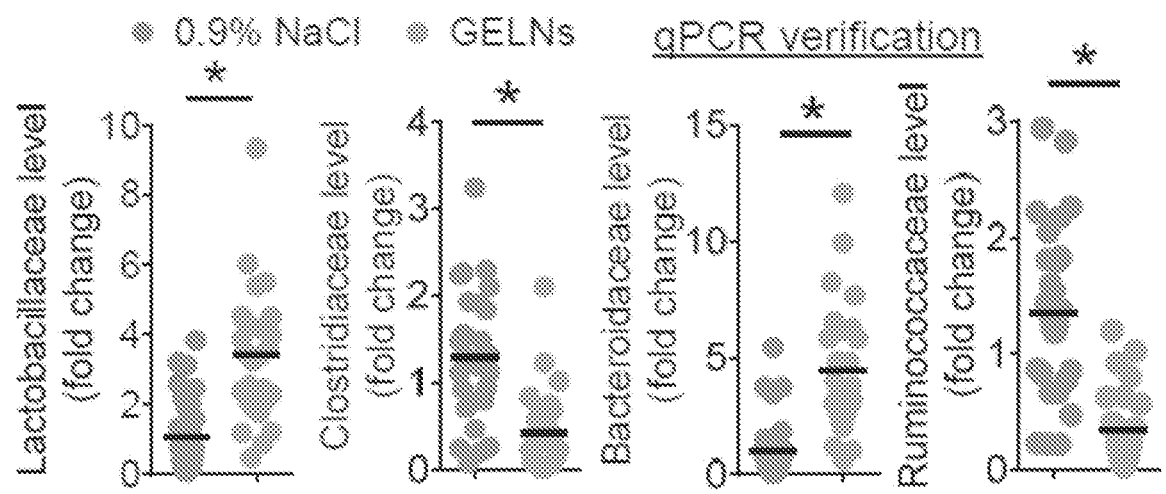
FIG. 7 presents fold-change analyses for selected bacteria verified with qPCR (NaCl control is the left bar and GELNs is the right bar in each bar graph).

To further determine whether the findings described above can be translated into clinical application, 16S rRNA gene sequencing data generated from stool samples of healthy subjects after oral GELN administration for a week were quantitatively analyzed (FIG. 7, top panel). To exclude the bias of gender in the study results, bacterial DNA from both males and females in each treatment group was pooled into three groups prior to 16S rRNA sequencing. The percentage of each bacterial species sequence in all sequence reads indicated an increase in Lactobacillaceae, Bacteroidaceae, and Bacteroidales S24-7, and a decrease in Clostridiaceae and Ruminococcaceae in GELN-treated subjects in comparison with particle vehicle (0.9% NaCl)-treated subjects (FIG. 7, middle panel; Table 4). The sequencing data from healthy subjects were subsequently verified with a qPCR assay (FIG. 7, bottom panel).

Considering the direct contact of food ELNs and numerous bacteria in the gut, it was hypothesized that food ELNs might be taken up by bacteria and the contents of food ELN RNAs could directly regulate gene expression in bacteria. To test this hypothesis, PKH26-labeled GELNs were administered to C57BL/6 mice via oral gavage. Confocal imaging analysis indicated that the GELNs were taken up by gut bacteria, and this result was further confirmed by quantitative fluorescence-activated cell sorting (FACS) analysis of PKH26$^+$ GELNs. To determine whether the changes in gut bacteria composition were associated with preferential uptake of GELNs by specific gut microbiota, PKH26$^+$ GELNs were administered to mice via oral gavage. The PKH26$^+$ bacteria from fecal samples of mice were sorted by FACS followed by 16S rRNA gene sequencing. The results showed that 31.54 (±7.92%) of the GELNs/PKH26-positive gut bacteria were Lactobacillaceae (FIG. 8; Table 5).

Next, whether the concept that edible plant exosomes could preferentially target bacteria in the intestine could be generalized was tested. ELNs from turmeric, which belongs to the same family as ginger, garlic, and grapefruit, were used as proof of concept. A 16S ribosomal rRNA gene library was generated, and 16S sequencing analysis of fecal samples from mice administered PKH26+ ELNs from garlic, turmeric, and grapefruit was performed (Table 5). The analysis of GELN+ bacteria suggested that all three types of ELNs were preferentially taken up by Bacteroidales S24-7. Interestingly, turmeric, from the same Zingiberaceae family as ginger, was also preferentially taken up by Lactobacillaceae. In contrast, garlic- and grapefruit-derived ELNs were preferentially taken up by Ruminococcaceae.

Figure 8:
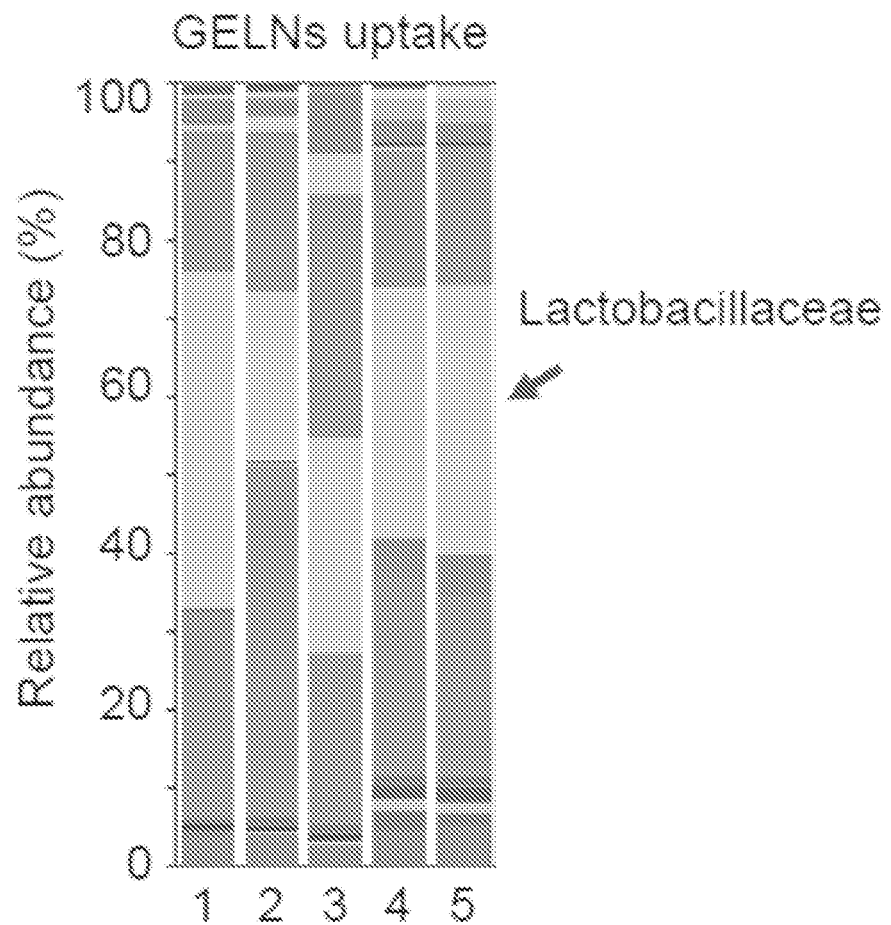
FIG. 8 is a bar graph showing the results of 16S rRNA sequencing at the level of family for bacteria with a preference for taking up GELNs. The data are representative of three independent experiments. Error bars are SD.
Figure 9:
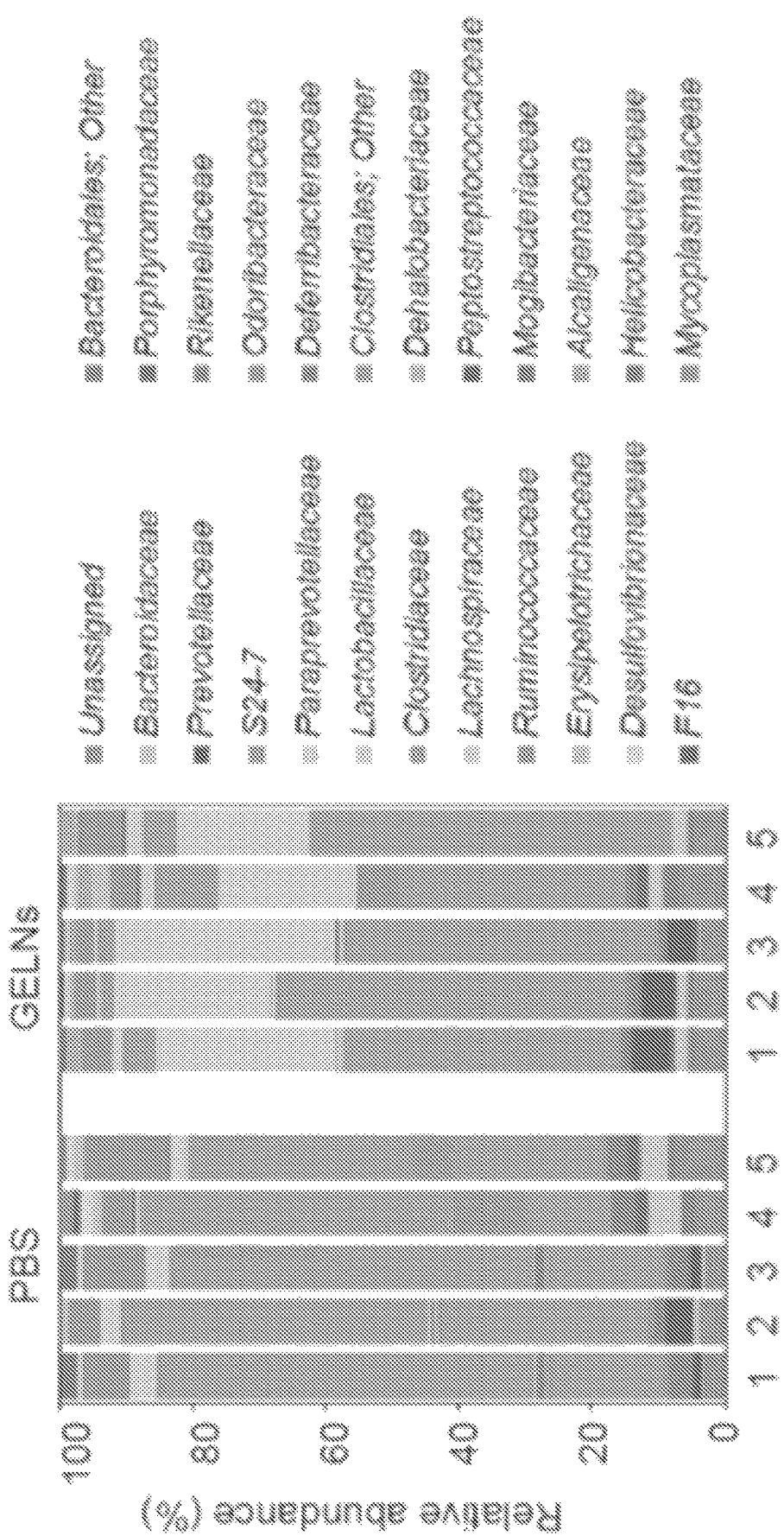
FIG. 9 shows the percentage of each bacteria sequences in all sequence reads at the level of family.
Figure 10:
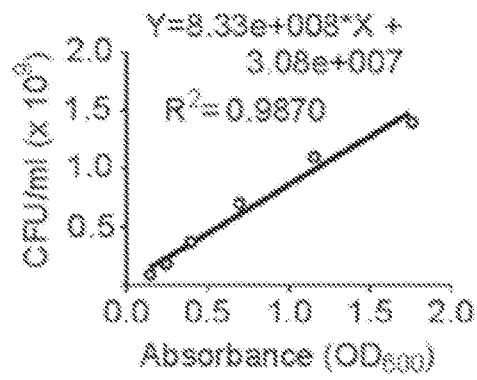
FIG. 10 is a graph showing a correlation of the optical measurements at $OD_{600}$ with CFUs. A linear regression (CFU/ml vs. $OD_{600}$) was performed in order to evaluate the quantification of *Lactobacillus rhamnosus* GG (LGG) CFU with optical measurements.
Figure 11:
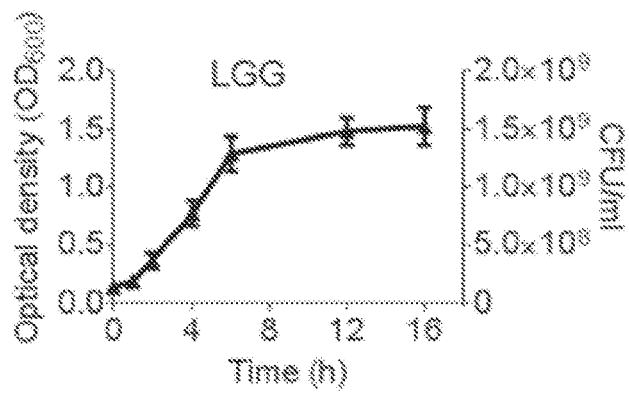
FIG. 11 is an LGG growth curve in exponential phase at 37° C. Error bars are ±standard deviation (SD).
Figure 12:
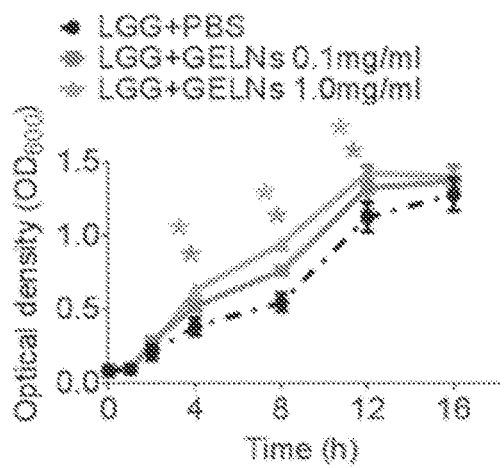
FIG. 12 is a graph of proliferation of LGG treated with GELNs at 0.1 mg/ml and 1.0 mg/ml at 37° C. The optical density of LGG at a wavelength of 600 nm was measured from 0 hours to 16 hours after treatment. *p<0.05. Error bars are ±SD.
Figure 13:
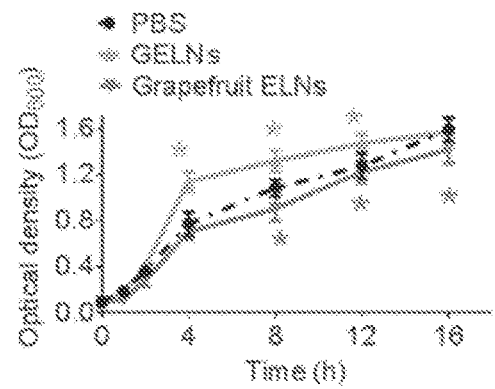
FIG. 13 is a graph of proliferation of LGG treated with ginger and grapefruit-derived ELNs at 1.0 mg/ml at 37° C. *p<0.05. Error bars are ±SD.

The data presented herein showed that Lactobacillaceae numbers increased in GELN-administered mice (see FIG. 9) and that GELNs were preferentially taken up by Lactobacillaceae (see FIG. 8). The results generated from in vitro cultures of LGG with GELNs indicated that GELNs directly promoted LGG growth (see FIGS. 10-13), whereas grapefruit-derived ELNs reduced LGG growth (FIG. 13).

Figure 14:
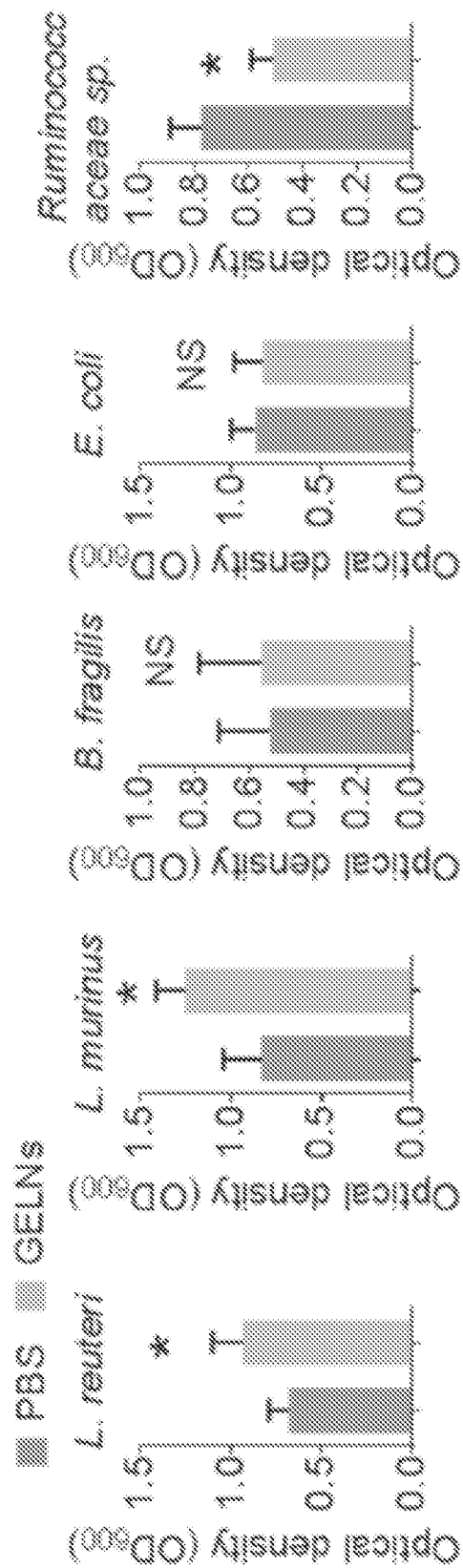
FIG. 14 is a series of graphs of proliferation of *L. reuteri, L. murinus, B. fragilis, E. coli,* and Ruminococcaceae sp. treated with GELNs or PBS at 37° C. for 8 hours. *p<0.05. Error bars are ±SD.
Figure 15:
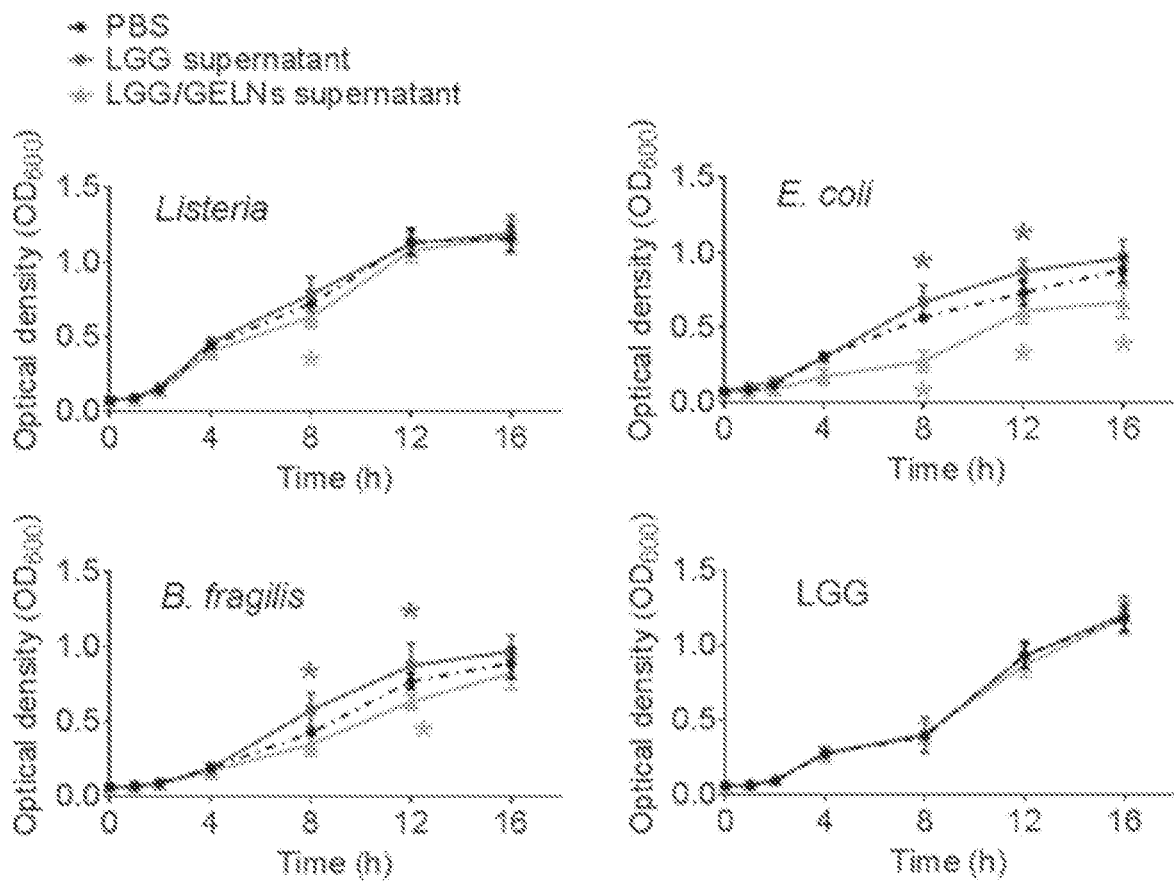
FIG. 15 is a series of graphs of proliferation of *Listeria monocytogenes* (Listeria), *Escherichia coli* (*E. coli*), *Bacteroides fragilis* (*B. fragilis*), and LGG (LGG) presented with LGG culture medium treated with GELNs. *p<0.05. Error bars are ±SD.
Figure 16:
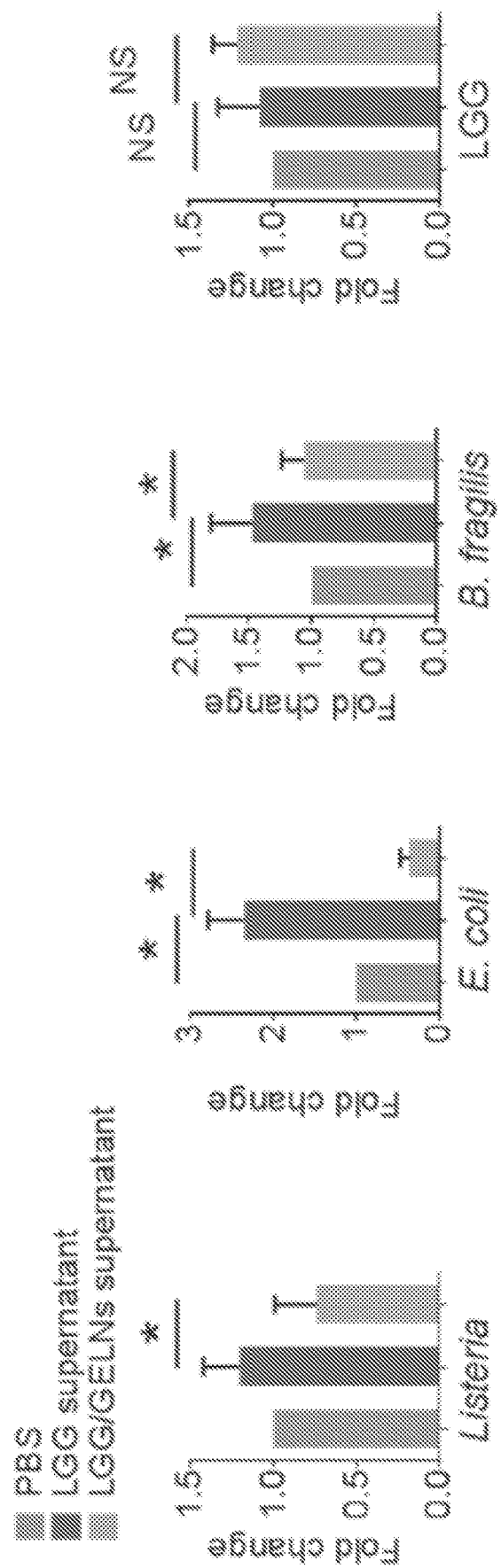
FIG. 16 is a series of bar graphs showing the results of LGG culture medium administered to C57BL/6 mice for 24 hours and the level of *Listeria, E. coli, B. fragilis,* and LGG in colon feces evaluated by qPCR. *p<0.05. Error bars are ±SD.

To determine whether GELNs also have an effect on the growth of other *Lactobacillus* species and other families of bacteria, the growth of *Lactobacillus reuteri* (*L. reuteri*), *Lactobacillus murinus* (*L. murinus*), *B. fragilis*, *E. coli*, and Ruminococcaceae sp. (TSD-27) was evaluated after incubation with GELNs for 8 hours. It was observed that GELNs also induced *L. reuteri* and *L. murinus* growth (FIG. 14). GELNs had no effect on *B. fragilis* or *E. coli* growth, but it was observed that GELNs inhibited Ruminococcaceae growth (FIG. 14). It is known that the metabolites released from one species of gut bacteria can have an effect on the growth of other species. The data presented herein showed that the metabolic products from GELN-treated LGG inhibited *Listeria*, *E. coli*, and *B. fragilis* growth in vitro (FIG. 15) and in vivo (FIG. 16) but had no effect on LGG growth. Collectively, these data suggested that GELNs regulated LGG metabolites, prompting the selection of LGG for further analysis of the molecular mechanisms underlying GELN-mediated biological effects on LGG.

Example 2

Figure 17:
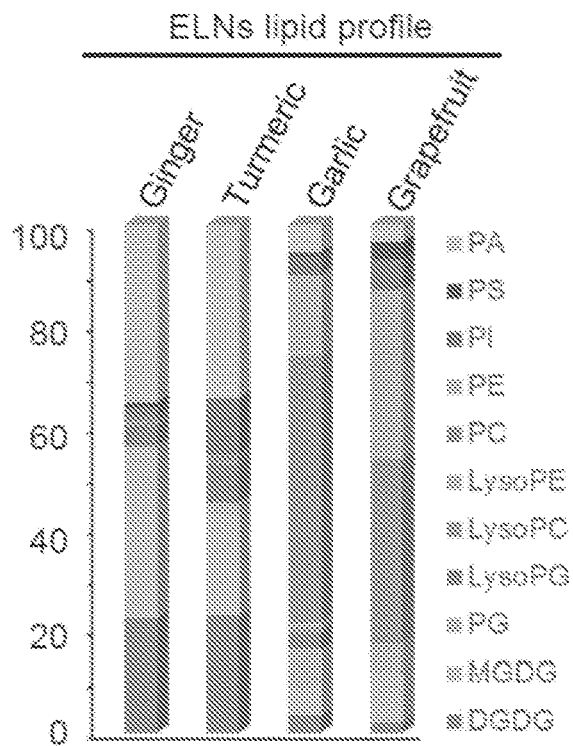
FIG. 17 shows the percentage of each lipid in all the lipids of ELNs from the indicated plants.

GELNs were Selectively Taken Up by Gut Bacteria and Regulated the Expression of LGG mRNA and Protein To explore the mechanism by which ELNs are preferentially taken up by specific bacteria, comparative lipid profiles generated from mass spectrometry (MS) analysis were assessed (Table 6). It was determined that GELN and turmeric ELN-derived lipids were enriched with phosphatidic acids (PAs; 35.2% and 34.4%, respectively), primarily 1,2-dilinoleoyl-sn-glycero-3-phosphate, C18:1/C18:3 (36:4) and 1-palmitoyl-2-linoleoyl-sn-glycero-3-phosphate, C16:0/C18:2 (34:2), whereas PAs in grapefruit and garlic represented only 3.5% and 5.5%, respectively, of the total lipid content (FIG. 17). In contrast, the majority of the lipid in grapefruit and garlic was phosphatidylcholine (PC, 36.2% and 52.6%, respectively).

Figure 18:
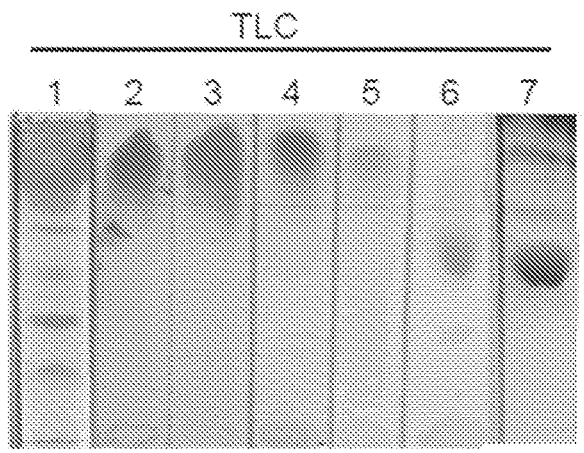
FIG. 18 is a photograph of GELN- and grapefruit ELN-derived lipids separated by thin-layer chromatography (TLC). PA and PC were loaded was as a standard marker.
Figure 19:
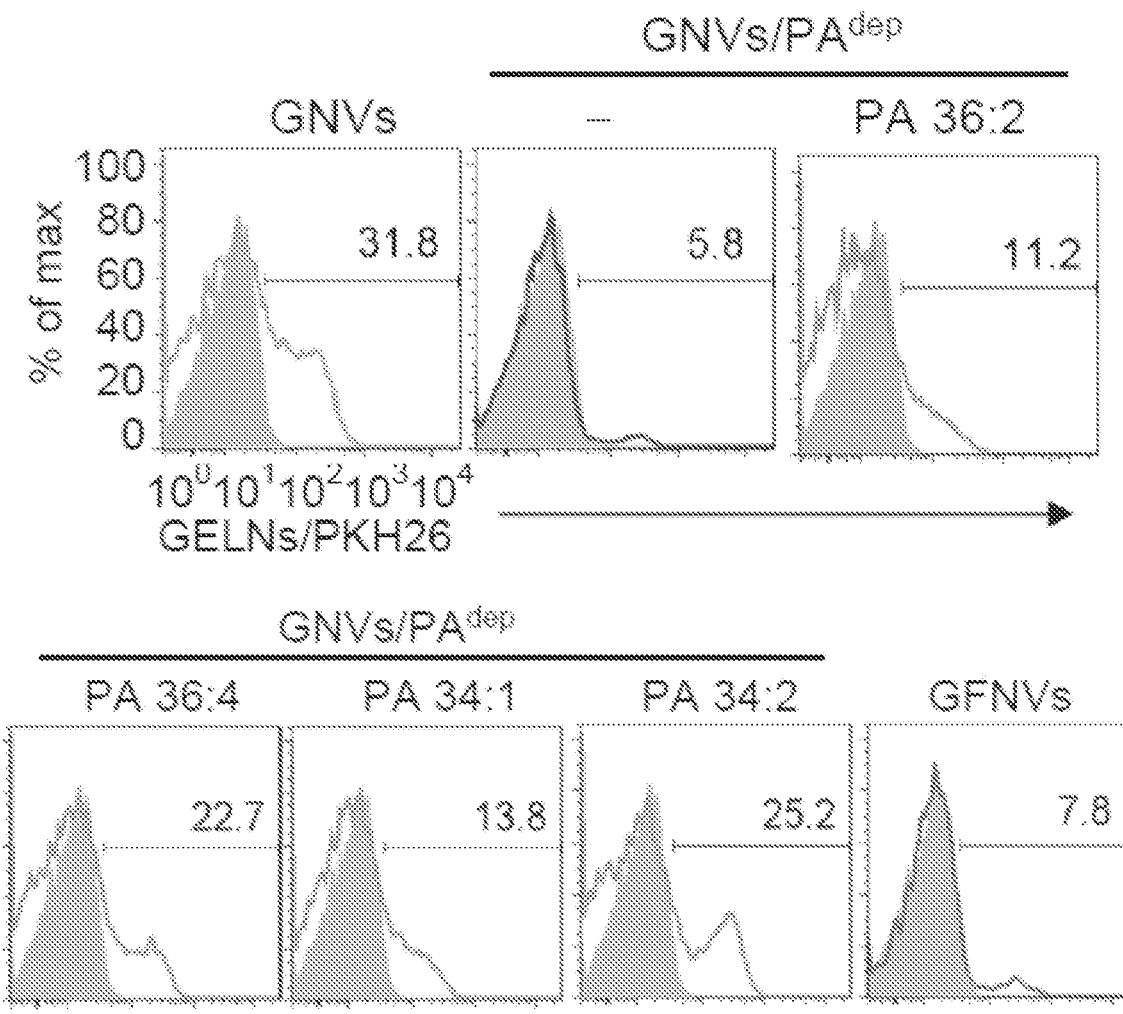
FIG. 19 is a series of FACS plots of GNVs generated with whole lipids, PA-depleted lipids from GELNs, and grapefruit ELNs, and supplementary PA with depleted lipids. PKH26-labeled GNVs exposed to LGG. PKH26-positive bacteria were quantitatively analyzed vis FACS.

It was hypothesized that GELN PA lipids might serve as a signal for preferential uptake by LGG. To generate PA-depleted GELN lipids, GELN lipids were isolated with chloroform and separated via thin-layer chromatography (TLC; FIG. 18). The band containing PA was identified based on standard PA migration in TLC and then removed. The results generated from GNVs made from PA-depleted GELN lipids (FIG. 19) indicated that depletion of GELN PA lipids leads to a significant reduction in GNV-positive LGG, whereas addition of PA 34:2 or PA 36:4 back into PA-depleted GNVs rescued the uptake of GNVs, and grapefruit ELN lipid-derived nanovector (GFNV) uptake by LGG was minimal (FIG. 19).

Figure 20:
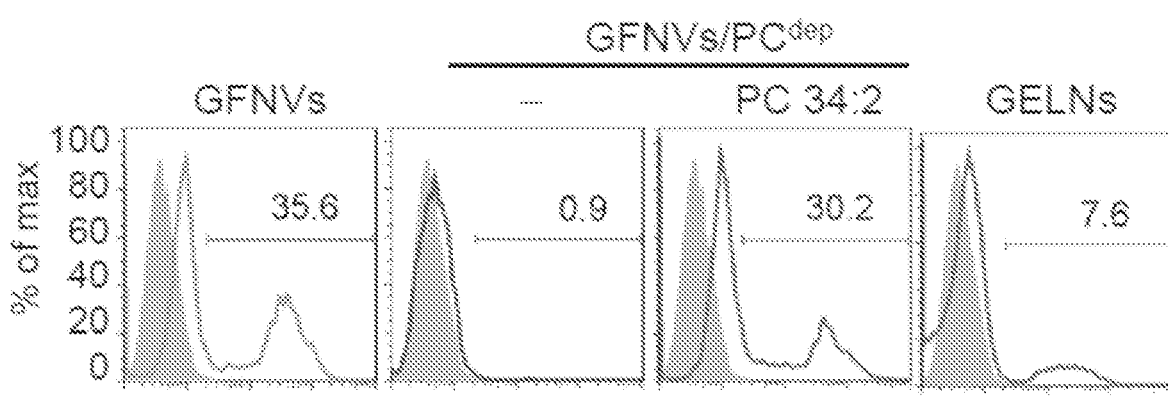
FIG. 20 is a series of FACS plots of analysis of LGG incubated with PKH26-labeled GNVs from whole grapefruit ELN lipids with or without PC depletion and supplementary PC with depleted lipids.

These data suggested that PA is required for GELN uptake by LGG. ELN lipid-dependent uptake was also demonstrated in grapefruit ELNs. FACS analysis indicated that PC-enriched grapefruit GFNVs were preferentially taken up by Ruminococcaceae sp. (TSD-27). PC depletion in grapefruit GFNVs resulted in reduced uptake by Ruminococcaceae, and the uptake was rescued by addition of PC 34:2 back into the PC-depleted grapefruit GNVs (FIG. 20).

Figure 21:
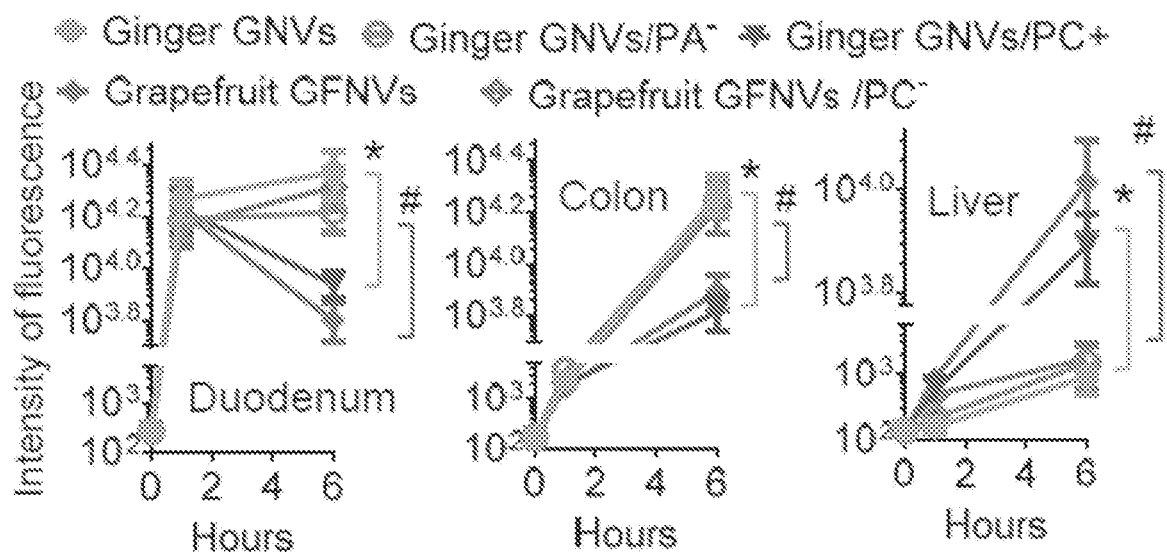
FIG. 21 is a series of graphs of quantification of fluorescence intensities of fluorescent images of the duodenum, colon, and liver from mice (n=5) receiving a gavage of DiR (1,1'-Dioctadecyl-3,3,3',3'-Tetramethylindotricarbocyanine Iodide) dye-labeled GNVs with or without PA or PC lipid. Ginger GNVs vs. ginger GNVs/PC+: *p<0.05; grapefruit GNVs vs. grapefruit GNVs/PC−: #p<0.05.

To further determine whether lipids also play a role in tissue targeting in vivo, mice were gavaged with DiR-labeled GELNs, PA-deleted GELNs, GELNs plus PC 34:2, grapefruit ELNs, and PC-depleted grapefruit ELNs. Analysis of imaging signals in mouse intestines and livers was performed at 1 hour and 6 hours after the gavage. The results suggested that PA lipids played a role in maintaining the duration and amount of ELN accumulation in the gut. PC lipid enhanced migration of ELNs from the intestine to the liver (see FIG. 21).

To determine whether GELNs had an effect on gene expression and protein production in LGG, the efficiency of PKH26-labeled GELN uptake by LGG in an in vitro culture assay was determined. LGG was incubated with PKH26-labeled GELNs for 1 hour at 22° C., and uptake of GELNs by LGG was visualized with confocal microscopy.

Figure 22:
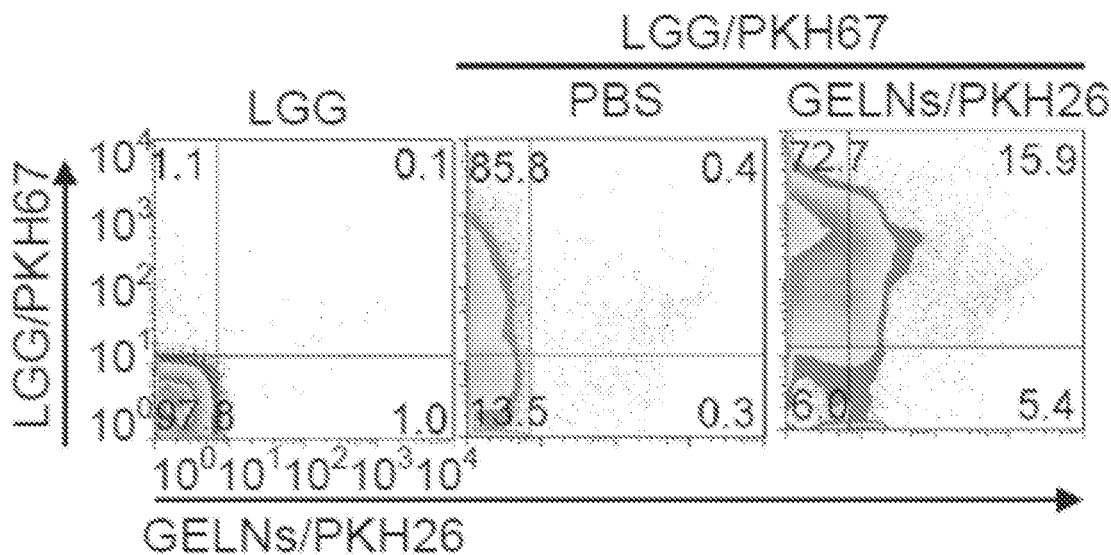
FIG. 22 is a series of FACS plots showing the frequency of PKH67-labeled LGG and PKH26-labeled GELNs assessed using flow cytometry. The numbers in the quadrants indicate the percentage of LGG in each.

GELN uptake in vivo was also evaluated. Briefly, two hours after mice were gavaged with PKH67 fluorescence-labeled LGG (1×10$^9$), the mice were administered PKH26-labeled GELNs (500 mg/kg of body weight in 300 µl PBS). Twelve hours after the last gavage, analysis of the PKH67+ PKH26+ double-positive bacteria suggested that LGG took up the GELNs. In vitro confocal and in vivo FACS analysis (FIG. 22) data suggested that LGG took up the GELNs.

Figure 23:
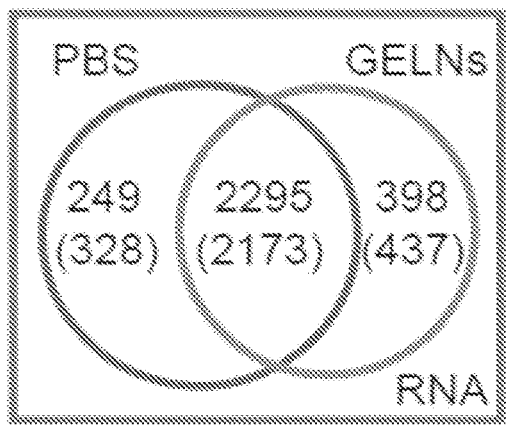
FIGS. 23 and 24 are Venn diagram of all mRNAs or proteins detected in LGG, respectively. The numbers in brackets indicate the in vitro results.
Figure 24:
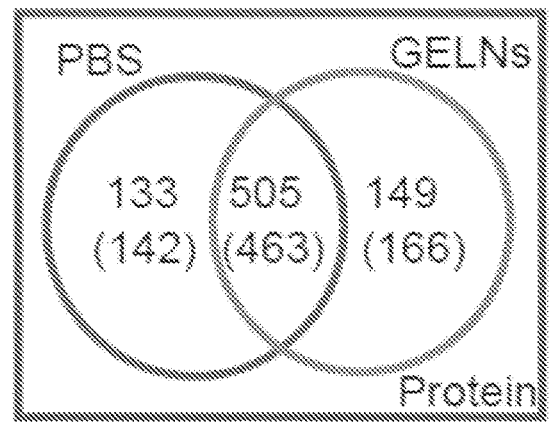
Figure 25:
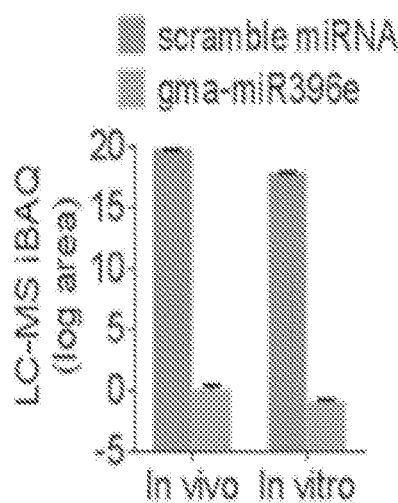
FIG. 25 is a bar graph of LC-MS analysis of protein LexA in LGG treated with gma-miR396e (SEQ ID NO: 119) or a scrambled (negative control) miRNA. *p<0.05. Error bars are ±SD.
Figure 26:
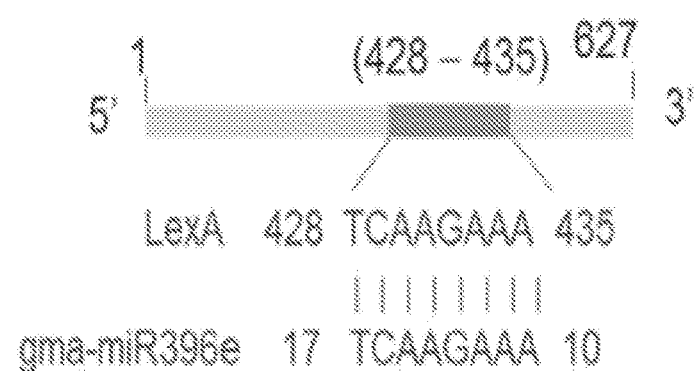
FIG. 26 is a schematic diagram of the putative binding sites of gma-miR396e (SEQ ID NO: 119) in the LexA. Data are representative of three independent experiments (error bars, SD). Treatment indicated in legend vs PBS, *p<0.05 (two-tailed t-test); NS, not significant.
Figure 27:
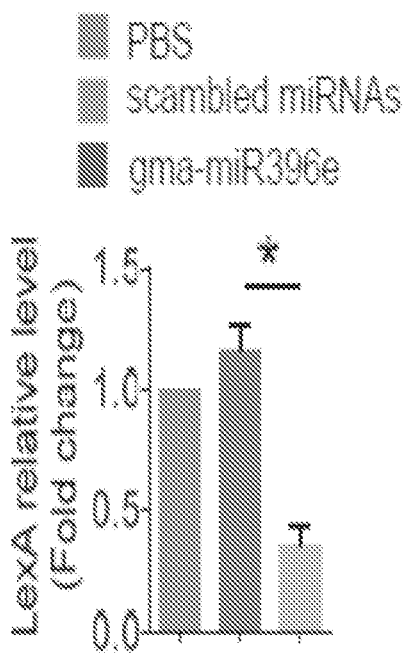
FIG. 27 is a bar graph of qPCR results of LexA expression in LGG treated with gma-miR396e (SEQ ID NO: 119; *p<0.05 by two-tailed t-test).
Figure 28:
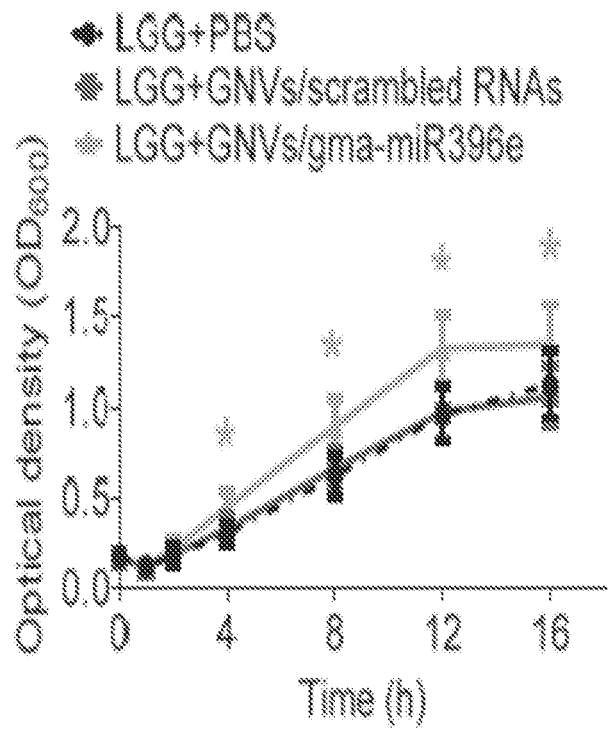
FIG. 28 is a graph of the analysis of LGG proliferation after treatment with gma-miR396e (SEQ ID NO: 119). *p<0.05 by two-tailed t-test. The data are representative of three independent experiments. Error bars are ±SD.

An LGG gene expression profile was obtained using next-generation mRNA sequencing (FIG. 23; Sequence Read Archive (SRA); available from the website of the NCBI; Accession Number SRP121341) and protein profiles using liquid chromatography-tandem mass spectrometry (LC-MS/MS; FIG. 24) of sorted (via FACS) PKH67+ PKH26+ LGG. The RNA sequencing (FIG. 23) and proteomic (FIG. 24) data analyses indicated that 398 mRNAs and 149 proteins were predominantly present in GELN-treated LGG. In addition, 249 LGG mRNAs and 133 proteins were reduced in GELN-treated LGG. The top 50 LGG mRNAs and proteins with altered expression are listed in Table 7. Among the LGG genes affected by GELN RNAs, the transcription repressor LexA was reduced due to GELN RNA treatment at both the transcript and protein level (FIG. 25). An alignment of nucleotide sequences using BLAST indicated that LGG LexA mRNA is one of the potential target genes of GELN gma-miR396e (Table 3, FIG. 26). LGG treated with gma-miR396e (SEQ ID NO: 119) had a lower level of LexA expression (FIG. 27) and grew faster than LGG treated with scrambled miRNA (FIG. 28).

Example 3

Figure 29:
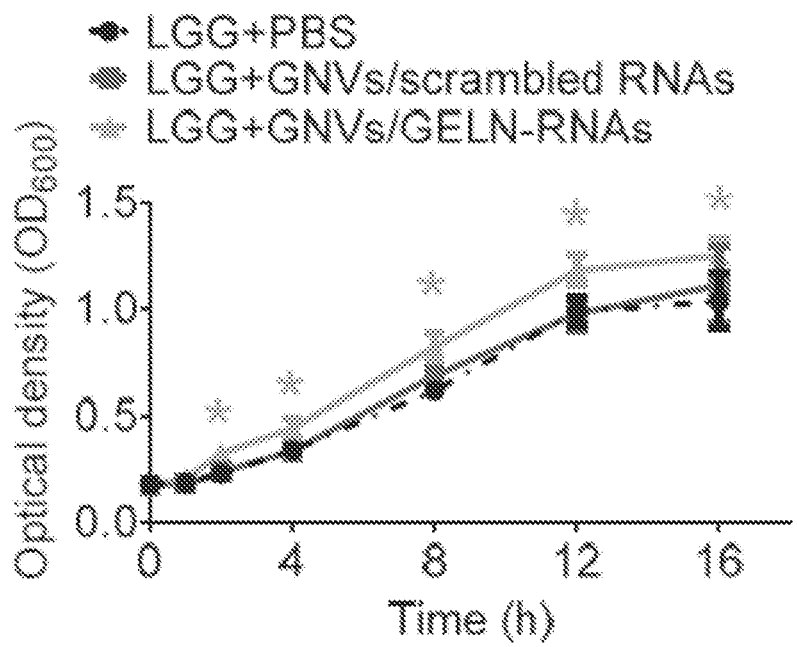
FIG. 29 is a graph of proliferation of LGG treated with GNVs/GELN-RNAs over time (*p<0.05).
Figure 33:
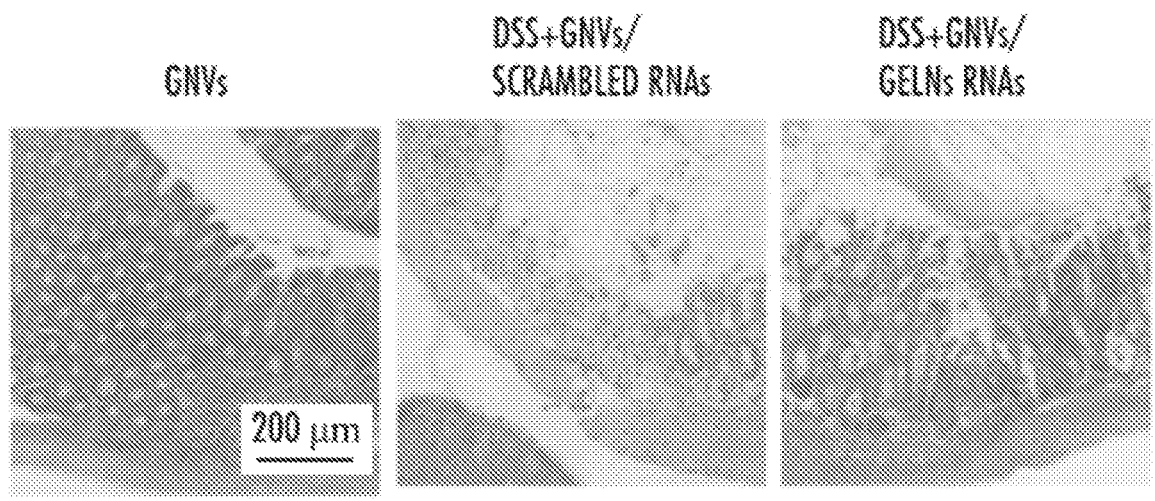
FIG. 33 are H&E-stained sections of colon (400× magnification) from mice treated as indicated.
Figure 34:
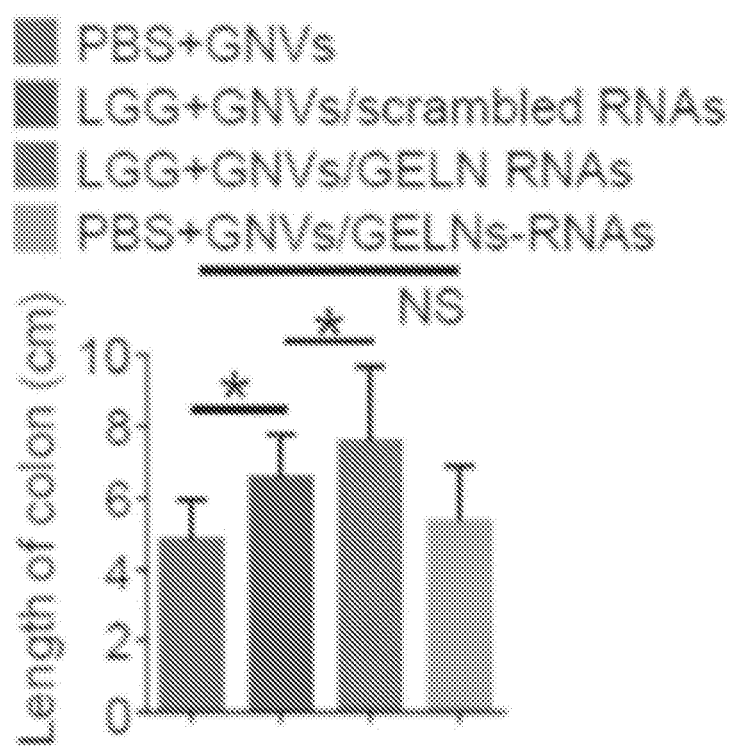
FIG. 34 is bar graph of quantification of colon length of mice treated as indicated. *p<0.05. Error bars are ±SD.
Figure 35:
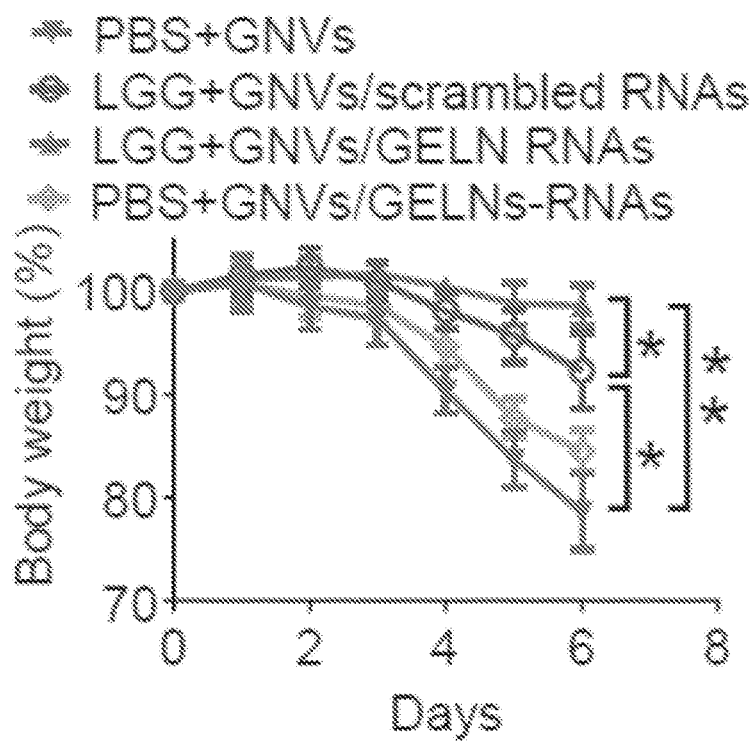
FIG. 35 is a bar graph of body weights of mice treated as indicated. *p<0.05; **p<0.01. Error bars are ±SD.
Figure 36:
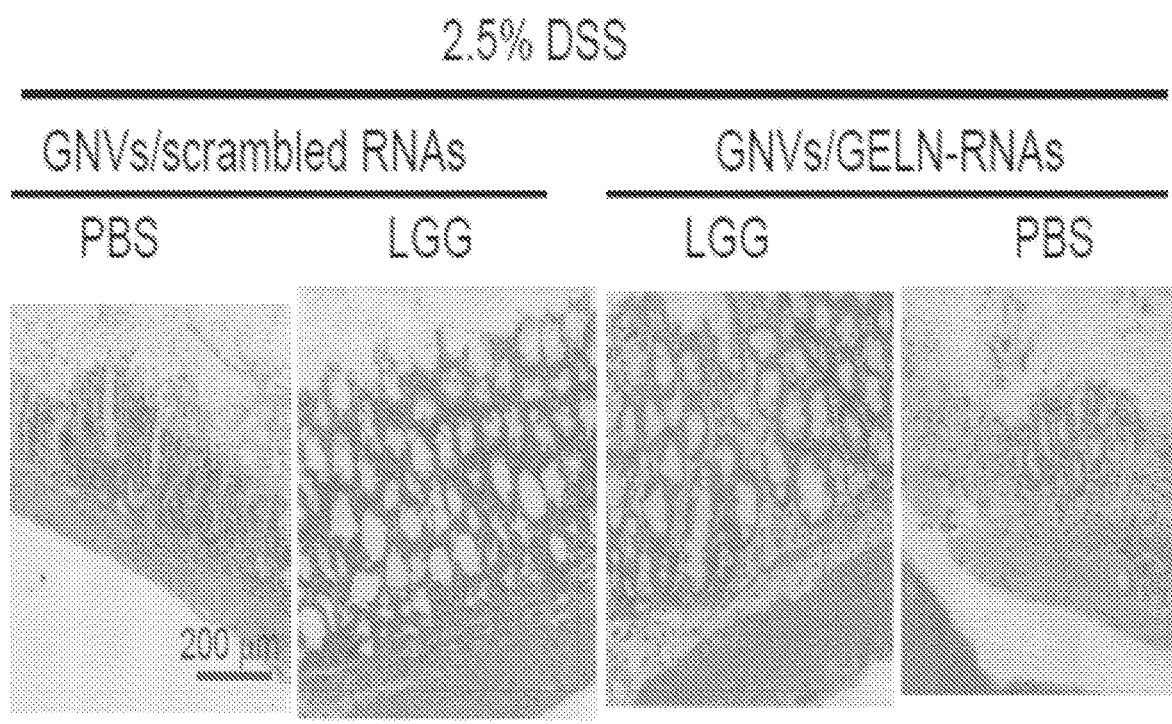
FIG. 36 is a series of H&E-stained sections of colon (400× magnification; scale bar is 200 μm).

GELN RNAs Enhanced LGG-mediated Inhibition of Mouse Colitis by Inducing IL-22 Expression Via Activation of the AHR Pathway RNA sequence analysis further revealed that GELN RNAs harboring the complementary seed-matching sequence of LGG mRNA had the potential for binding gut bacterial mRNA (Tables 2 and 3). Evidence indicating a similarity in regulating the composition of gut microbiota of mice fed with GELNs and GELN RNA (see Table 8) prompted a further examination of whether GELN RNAs could modulate bacterial function and in turn host biology. First, evidence showing PKH26-labeled GNVs encapsulating GELN-RNAs were present in LGG was visualized using confocal microscopy. LGG growth in MRS broth was induced by GELN RNAs but not by scrambled RNAs (FIG. 29). The results indicated that mice fed GNV/GELN-RNAs had superior protection against DSS-induced mouse colitis compared with mice fed GNV/scrambled RNA (FIGS. 30-33), suggesting that the protective effect on DSS-induced mouse colitis was GELN RNA-specific. The results generated from DSS-induced colitis in germ-free mice further demonstrated that LGG was required for better protection of mice against DSS-induced colitis because germ-free mice administered GNVs/GELN-RNAs without LGG did not experience a reduction in colitis severity (FIGS. 34-34).

Figure 37:
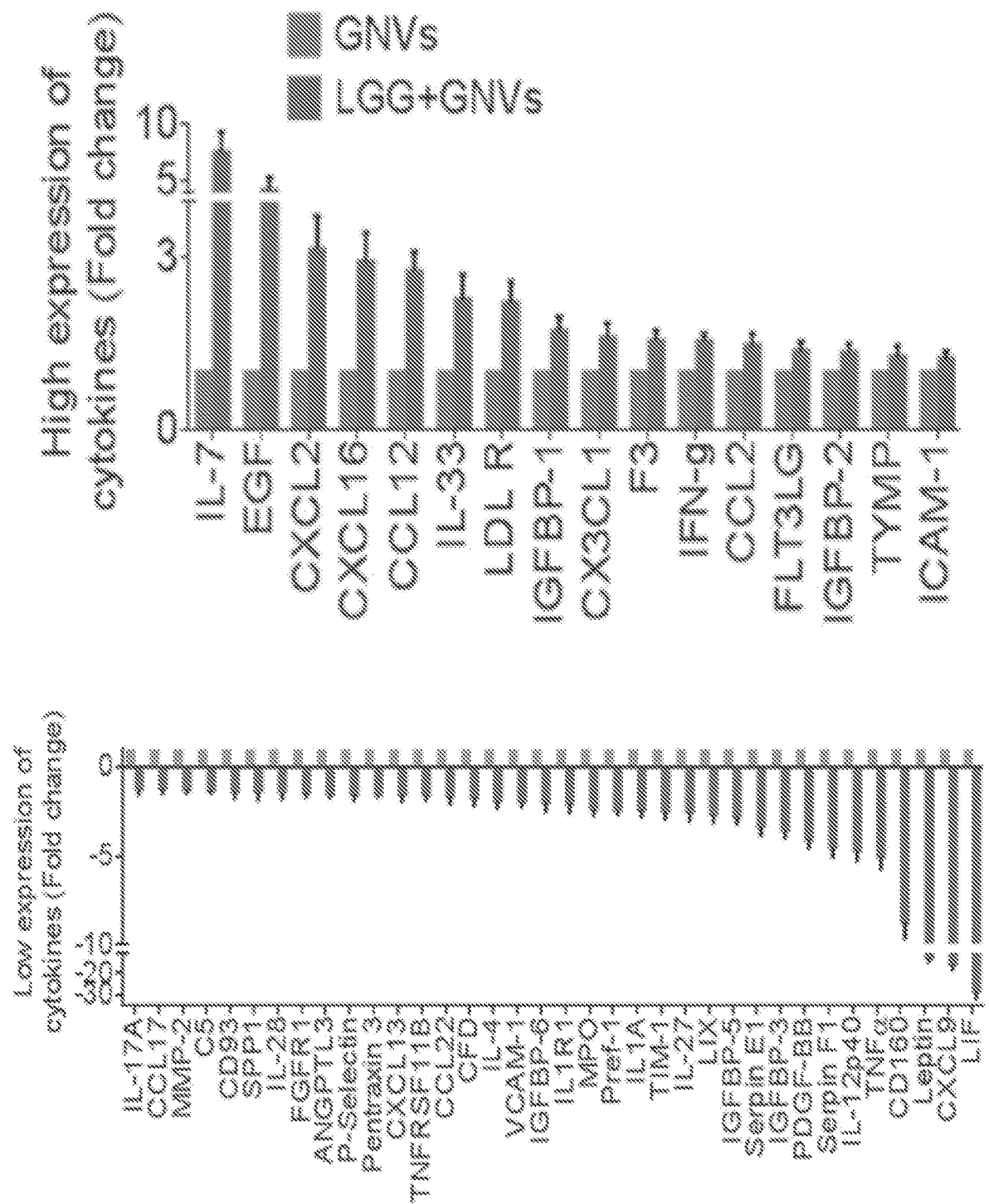
FIG. 37 is a pair of bar graphs of quantification of relative intensity of the up-regulating (top panel) cytokines and down-regulating (bottom panel) cytokines shown in a cytokine array (LGG vs PBS; p<0.05).
Figure 38:
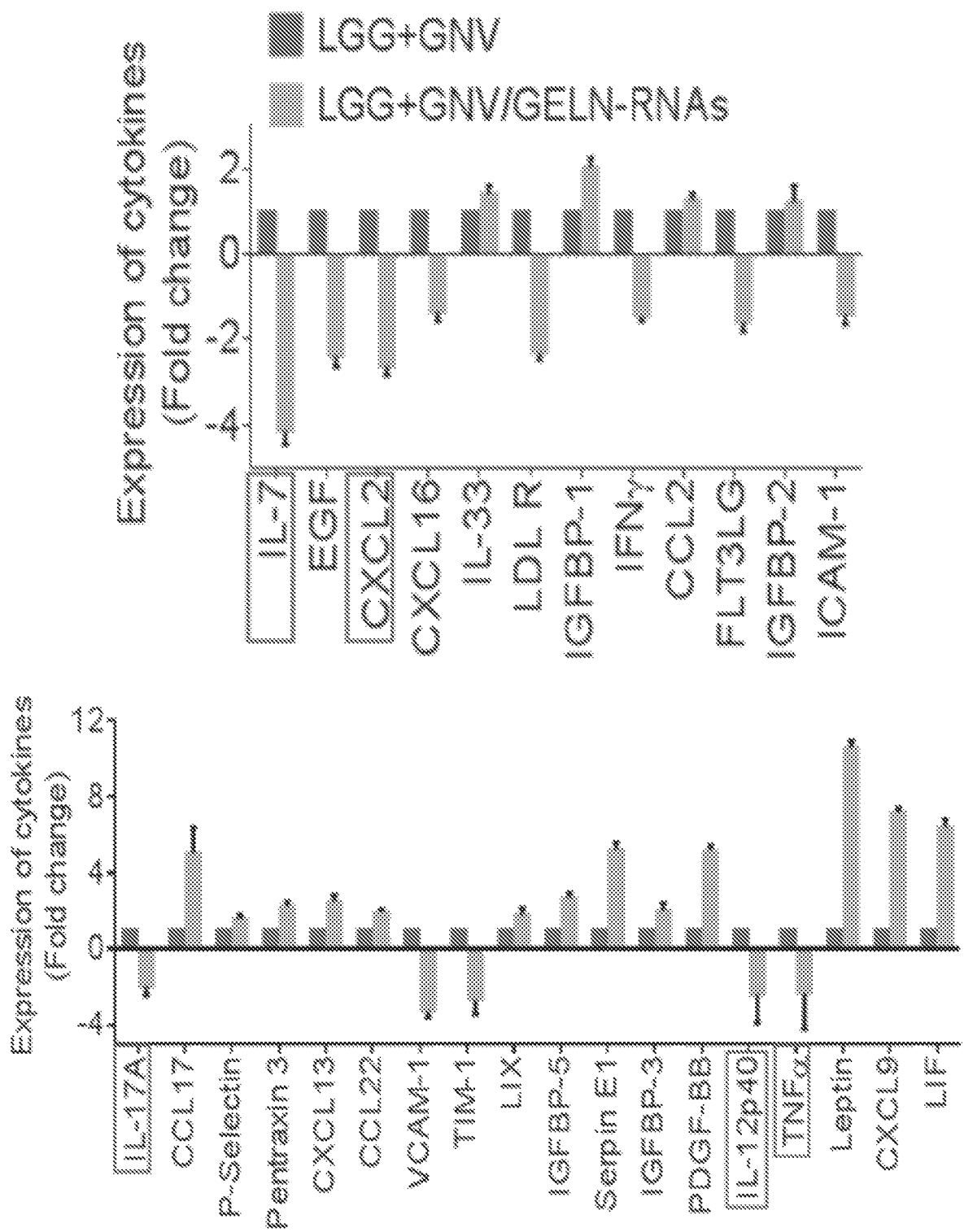
FIG. 38 is a pair of bar graphs of quantification of relative intensity of the down-regulating cytokines (top panel) and up-regulating (bottom panel) cytokines shown in cytokine array (LGG/GELN RNAs vs. LGG: *p<0.05).
Figure 39:
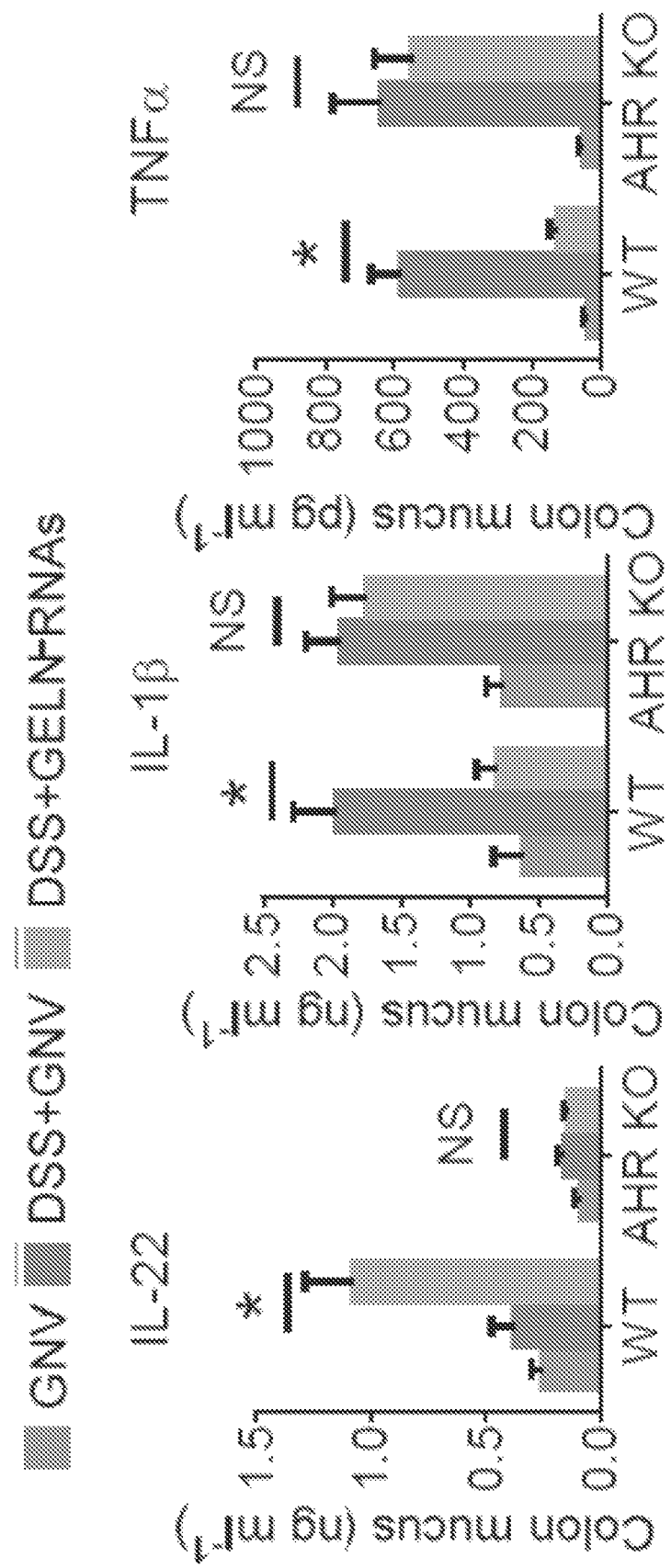
FIG. 39 is a series of bar graphs showing levels of the indicated cytokines in mucus of the colons of wild-type (WT) and AHR knockout (AHR KO) mice (n=5 each) supplied with 2.5% DSS after gavage with GELN RNAs or scrambled RNAs. ELISA analysis of IL-22 (left bar graph), IL-1β (middle bar graph), and TNFα levels (right bar graph)

Cytokine array analysis (FIGS. 37 and 38) indicated that the levels of the majority of proinflammatory cytokines/chemokines were decreased in the colon tissue of germ-free mice treated with LGG+GNVs/GELN-RNAs (FIGS. 37 and 38) in comparison with germ-free mice treated with LGG alone. In addition to confirmation of a reduction in the TNFα level in pathogen-free (SPF) mice, ELISA analysis indicated that GELN-RNA treatment inhibited the induction of the proinflammatory cytokines IL-1β and TNFα and promoted the production of IL-22 in colon mucus from DSS-treated SPF mice (FIG. 39). Failure of IL-22 induction by GELN-RNAs in germ-free mice suggested that IL-22 induction by GELN-RNAs was bacteria-dependent. It is known that the aryl hydrocarbon receptor (AHR) pathway contributes to induction of IL-22 (Monteleone et al., 2011).

Whether the GELN-mediated inhibition of IL-1β and TNFα and the increase in IL-22 occurred through the AHR pathway was tested. Knockout (KO) of AHR led to neither inhibition of IL-1β and TNFα expression nor an increase in the expression of IL-22 in AHR KO mice with DSS-induced colitis (FIG. 39).

Next, the molecular basis of LGG+GNV/GELN-RNA-mediated induction of IL-22 was tested. LGG metabolizes tryptophan to indole derivates, including I3A, which acts as a ligand for AHR, inducing local production of IL-22. High-performance liquid chromatography (HPLC) analysis indicated that the level of I3A in the feces of GELN-RNA-treated C57BL/6 mice dramatically increased (FIG. 40) compared with that in feces from mice treated with GELN-scrambled RNA, whereas the level of indole-3 acetamide (I3AM), another metabolite of tryptophan, decreased (FIG. 41). Interestingly, indole-3-acetaldehyde (IAAld), which is an intermediate metabolite product for synthesis of I3A, was also induced in the feces of GELN-RNA-treated mice (FIG. 40).

The role of I3AM in generation of I3A was then determined. HPLC analysis indicated that addition of I3AM to LGG cultures significantly inhibited GELN-RNA-mediated induction of the I3A precursor, IAAld (FIGS. 42 and 43). To further determine the inhibitory effect of I3AM on the production of LGG I3A, the quantities of IAAld (FIG. 44, left panel) and I3A (FIG. 44, right panel) in MRS media of LGG treated with different concentrations of I3AM was analyzed. It was determined that I3AM inhibited the production of IAAld and I3A in a dose-dependent manner, and the inhibitory effect of I3AM on the production of I3A was cancelled by additional IAAld (FIG. 44), suggesting that the I3AM-mediated inhibitory effect on I3A production occurs upstream of IAAld. Additional IAAld also cancelled the I3AM-mediated inhibitory effort on IL-22 production (FIG. 45, left panel). This inhibitory effect did not occur in AHR KO mice treated with LGG supernatant exposed to I3AM (FIG. 45, right panel), indicating that the inhibitory effect of I3AM on LGG I3A-mediated induction of IL-22 occurred via the AHR pathway.

Protein LC-MS/MS and mRNA sequencing analysis indicated that the expression of monooxygenase ycnE (also called antibiotic biosynthesis monooxygenase [*Lactobacillus rhamnosus* GG]; GENBANK® biosequence database Accession No. CAR87039) in LGG (FIG. 46) was inhibited by GELN-RNA (FIG. 24). Monooxygenase is a key enzyme that catalyzes tryptophan to I3AM (Stutz, 1958; Kosuge et al., 1966). It was determined that GELN-derived mdo-miR7267-3p had a potential binding site for mRNA encoding LGG monooxygenase ycnE. qPCR data generated from LGG treated with mdo-miR7267-3p indicated that ycnE gene expression was indeed inhibited (FIG. 47), and HPLC analysis indicated that mdo-miR7267-3p treatment led to inhibition of I3AM (FIG. 48, left panel) and induction of I3A (FIG. 48, right panel). Tryptophan was metabolized into I3A and I3AM in LGG. Production of I3AM and I3A was regulated by LGG ycnE. After chemical equilibrium was reached, the net amount of accumulated tryptophan was dependent on ycnE enzyme activity. The data presented herein indicated that tryptophan was accumulated due to GELN-RNA-mediated blocking of I3AM production and was not utilized for I3A production at 100%.

To validate that the induction of I3A by GELN-RNAs is gut bacteria-dependent, broad-spectrum antibiotic treatment was used to deplete gut bacteria prior to GELN-RNA administration. The I3A level in feces of antibiotic-treated mice was decreased, and GELN-RNAs no longer induced I3A until additional LGG was administered (see FIG. 49).

Whether the AHR pathway in gut lymphocytes of mice gavaged with GELN-RNAs was activated was tested by evaluating phosphorylation of AHR and induction of IL-22. Mice were gavaged with GELN-RNA one week prior to being treated with 2.5% DSS in drinking water for one additional week. Lymphoid cells were then isolated from the colon of treated mice. Western blotting analysis indicated that the levels of cytochrome P450 1A1 (CYP1A1) and phosphorylated AHR increased as a result of GELN-RNA treatment without affecting the total amount of AHR (see FIG. 50). FACS analysis indicated that CD3$^+$ RORγt$^+$ cells from GELN-RNA-treated mice exhibited increased IL-22 expression (FIG. 51). However, the induction of IL-22 in CD3$^+$ RORγt$^+$ cells was abolished in AHR KO mice (FIG. 51).

To further address whether the metabolites of LGG treated with GELN-RNAs might have an impact on the induction of IL-22 via the AHR pathway, colon lymphocytes from naïve B6 mice were incubated for 3 hours with I3A, MRS supernatant of LGG treated with GELN-RNAs, or GNVs only. ELISA results indicated that I3A induced expression of IL-22, and more IL-22 was induced when the colon lymphocytes were treated with LGG supernatant (FIG. 52). In contrast, there was no evidence of an impact of I3A and LGG supernatant on the induction of IL-22 in colon lymphocytes from AHR KO mice (FIG. 52). Collectively, these data suggested that metabolites from the supernatants of LGG treated with GELN-RNAs induce IL-22 via the AHR pathway.

Dysfunction of the gut epithelial barrier is a hallmark of inflammatory intestinal diseases. The intestinal epithelial barrier is maintained by tight junctions that connect adjacent epithelial cells and seal the paracellular space. IL-22 is critical for maintenance of the intestinal barrier function. Whether GELN-RNA-mediated induction of IL-22 played a causative role in protecting mice against colitis was tested. Indeed, unlike WT mice, IL-22 KO led to a loss of GELN-RNA-mediated protection against DSS-induced colon injury (FIGS. 53 and 54). This result agreed with the fact that GELN-RNA reduced gut permeability, shown by a fluorescein-5-isothiocyanate (FITC)-conjugated dextran assay (FIG. 55), and increased the expression of the Gjb, Cldn, and Jam2 genes, which play a role in regulating gut epithelial tight junction stability. Collectively, these data suggested that the preventive effect of GELN-RNAs on mouse colitis was at least partially IL-22 dependent.

Example 4

GELN Ath-miR167a Prevented LGG Accumulation in Gut Mucosa by Down-Regulating the LGG Pili Gene, SpaC LGG that took up GELN-RNAs exhibited reduced migration into the bloodstream and liver of DSS-treated SPF (FIGS. 56 and 57) and germ-free (FIG. 58) mice compared with LGG alone. The mucosa-associated LGG was decreased, particularly in the colon (FIG. 59). These findings were corroborated with confocal microscopy), showing that most of the PKH26-labeled LGG stayed in the intestinal lumen of mice that had been fed LGG prepulsed with GNVs/GELN-RNAs. Moreover, the data generated from in vitro assays via colony-forming unit (cfu) quantification of LGG entry into C57BL/6 murine colon MC38 cells and human colon epithelial Caco2 cells (FIGS. 60 and 61) and confocal examination of colocalization of LGG with GNVs/GELN-RNAs in MC38 cells (FIG. 62) further supported the notion that GELN-RNAs prevented LGG entry into both mouse and human gut epithelial cells.

The LGG pilus-specific protein SpaC was down-regulated at both the transcriptional and protein levels when LGG was treated with GELNs. Experimentally, based on array data and in vitro transmigration of colon epithelial cell data (see FIGS. 60-63), it appeared that GELN-RNAs prevented the invasion of LGG into gut epithelial cells.

To further investigate the mechanism underlying how GELN-RNAs prevented LGG migration, nucleotide sequences were aligned using BLAST, and the results indicated that the GELN miRNA ath-miR167a might directly bind to the LGG pilus protein SpaC mRNA and regulate SpaC expression (see Table 3). MC38 cells exposed to LGG treated with seven specifically selected GELN-derived miRNAs indicated that ath-miR167a-5p, ath-miR842 (SEQ ID NO: 82), and ath-miR827 (SEQ ID NO: 81) could prevent the entry of LGG into gut epithelial cells (FIG. 64). Considering the critical role of SpaC in LGG migration and that ath-miR167a-5p has eight complementary bases with SpaC mRNA, it was hypothesized that GELN ath-miR167a regulated the expression of SpaC in LGG.

Investigation of the effect of GELN miRNA on LGG migration in vivo indicated that ath-miR167a significantly reduced LGG translocation into the peripheral blood, and LGG remained on mucosal surfaces (FIG. 65). LGG treated with ath-miR167a had significantly down-regulated SpaC mRNA (FIG. 66) and protein expression compared with LGG treated with a scrambled miRNA. TEM images showed that much less SpaC protein could be detected on pili of LGG treated with ath-miR167a compared with those exposed to PBS or scrambled miRNA. A mutation that disrupted the binding site for ath-miR167a entirely restored GFP expression (FIG. 67).

To further determine whether SpaC was specifically targeted by miR167a-5p, the effects of SpaC on entry into gut epithelial cells and mucosa-associated LGG and miR167a-5p-treated LGG growth was tesetd. Immuno-TEM demonstrated that SpaC deleted (SpaC$^{del}$) LGG had no detectable SpaC. SpaC$^{del}$ LGG was less efficient in entering MC38 cells than wild-type LGG. Although the gene encoding for SpaC was not detected in SpaC$^{del}$ LGG (FIG. 68, left panel) and there was no difference in the in vitro growth between wild-type LGG and SpaC$^{del}$ LGG (FIG. 68, middle panel), the in vivo results showed that fewer SpaC$^{del}$ LGG were present on the mucosa than wild-type LGG (FIG. 68, right panel). miR167a-5p treatment had no effect on the growth of SpaC$^{del}$ LGG compared with scrambled miRNA (FIG. 69).

Then, to further demonstrate the role of endogenous miR167a-5p in the context of GELN RNA, miR167a-5p was depleted from the pooled GELN RNAs with biotinylated anti-sense miR167a-5p. Then, GELN RNA or scrambled miRNA was encapsulated in GNVs. qPCR data indicated that miR167a-5p was successfully depleted from the pooled GELN RNA (FIG. 70). GELN RNAs with depletion of miR167a-5p had no effect on the expression of the LGG SpaC gene in comparison with GNV-scrambled miRNA-treated samples (FIG. 71). The depletion of GELN miR167a-5p had no effect on the level of mucosa-associated LGG compared with data generated from GNV-scrambled miRNA-treated LGG (FIG. 72). Collectively, these data suggested that after exposure to GELN-RNA, the LGG SpaC gene was targeted and down-regulated by GELN miR167a-5p.

Discussion of the Examples

Extensive research has shown that diet modulates the composition and function of the gut microbiota in humans and other mammals (Claesson et al., 2012; Cotillard et al., 2013; Desai et al., 2016; Dey et al., 2015; Lukens et al., 2014; Muegge et al., 2011; Schwarzer et al., 2016; Sonnenburg & Bäckhed, 2016). Despite the body of knowledge that exists on fecal RNA, the impact of gut RNA on the microbiota is particularly poorly understood. Here, small RNAs and miRNAs from ELNs were identified and found to modulate the composition of gut microbiota and their metabolites and inhibit mouse colitis. At a molecular level, the present disclosure supports the idea that: (1) lipid-enriched ELNs send a signal that causes their uptake by gut bacteria; (2) ELN small RNAs mediate the cross-talk between gut microbiota and the host immune system, shaping the homeostatic balance between immunity and gut microbiota; and (3) ELN RNA regulates the composition, metabolites, growth, and localization of gut microbiota. Specifically, it was determined that gut probiotic LGG I3A induced by GELN-RNA promotes the expression of IL-22 through activation of the AHR signaling pathway, eliciting antimicrobial immunity and tissue repair at barrier surfaces.

A given miRNA can have hundreds of different bacterial mRNA targets (Hausser & Zavolan, 2014), several hundred miRNAs might be encapsulated in a given edible plant ELN, and ELNs from one type of edible plant could have a different miRNA profile than those from other plants. Therefore, it is conceivable that unlike endogenous miRNA released from host intestinal epithelial cells (Liu et al., 2016), which release a limited number of miRNAs, a large number and variety of food-derived ELN miRNAs can be taken up by gut microbiota. In addition, in terms of gut bacterial targeting, the ELNs from one type of edible plant could also have a different lipid profile, resulting in a targeting signal that is distinct from other ELNs. Therefore, a large variety of ELN-derived miRNAs and lipids could meet the requirement for potential regulation of the more than two million genes present in the gut microbiota through dietary-derived ELNs in a lipid targeting and a sequence-specific manner.

All organisms possess a diverse set of genetic programs that are used to alter cellular physiology in response to environmental cues. LexA acts as a transcriptional repressor of the SOS response genes coding primarily for error-prone DNA polymerases, DNA repair enzymes, and cell division inhibitors (Miller et al., 2004). The observation that GELN gma-miR396e (SEQ ID NO: 119) promoted LGG growth at least partly through inhibition of LexA expression supports the hypothesis that ELNs from different types of food could have a role in regulating LexA-mediated SOS activity in the intestinal microenvironment. In addition, since SOS activity has a direct effect on the bacterial cell cycle and survival in general and ELNs from different types of food have preferential bacterial hosts, it is conceivable that the SOS activity in different species of gut bacteria is dependent on what types of food are eaten. Therefore, the present disclosure also supports the hypothesis that ELN-dependent SOS activity has an effect on the composition of gut microbiota through regulating the bacterial cell cycle and bacteria survival.

Ingestion of probiotics, beneficial molecules, or microbes is designed to deliver a health benefit to the host by increasing the numbers of beneficial microbes or their products within the gut. From a therapeutic application aspect, using ginger ELN-derived liposomes, it was possible to orally deliver miRNA to target gut bacteria for treatment of mouse colitis. This strategy could provide an alternate approach for gene therapy in gut dysbiosis-related disease and provide a rationale for ELN-based oral delivery of therapeutic miRNA for treatment of disease due to dysbiosis. It is conceivable that gut bacterial activity regulated by miRNA that interacts with bacterial mRNA in a gene-specific manner will have many advantages over other approaches such as chemotherapy drugs, which induce gut dysbiosis, and antibiotic treatment, which drives rapid development of resistant strains.

A variety of host-derived factors, such as antimicrobial peptides, play a crucial role in selecting and maintaining the stable diversity of the gut microbiota. Edible plant-derived factors that selectively regulate the stability of mucosa-associated microbiota have not been studied in detail. As disclosed herein, it was determined that the ratios of LGG among other species of mucosa-associated microbiota can remain stable, with a shift from mucosal-associated LGG to the majority of the LGG accumulating in the lumen. In zebrafish, an increased level of lumen-associated LGG has a more beneficial effect on gut barrier function than mucosal LGG (He et al., 2017); the role of lumen-associated LGG in mammals is less well understood. The results presented herein explain how GELN small RNAs contribute to gut health via the LGG pilus-specific protein SpaC.

While not wishing to be bound by any particular theory of operation, since all of the diets that have been tested in the past contained ELN small RNAs, the concept that spatial niche partitioning could be governed by diet ELN small RNAs is possible, and this could help to explain both the long-term persistence of relatively stable numbers and the resilience of the microbiota, as well as the resistance to colonization by pathogens. Furthermore, the immune system has an active role in allowing only beneficial species to access these locations during homeostasis, as demonstrated herein above by IL-22. The presently disclosed subject matter thus opens up avenues for investigating whether other factors, such as GELN lipids and ELNs from other diets, can also participate in selection of which particular bacterial species are close to the epithelium and the creation of stable reservoirs for microorganisms to persist in the face of rapidly changing conditions in the gut lumen. Thus, through localized, immune-facilitated and adherence-dependent ELN selection, the host can maintain the stability of a diverse community of microbial symbionts.

In conclusion, given the importance of gut microbiota in human physiology, the findings disclosed herein revealed an important molecular mechanism underlying how diet ELN miRNAs can cross-talk with gut microbiota to maintain gut health. Because the composition of diet-derived ELN miRNAs and lipids is different among diets and each ELN miRNA has targets specific bacterial mRNA, this feature could be utilized for specific manipulation of the microbiome for human health and treatment of dysbiosis-related disease.

REFERENCES

All references cited in the instant disclosure, including but not limited to all patents, patent applications and publications thereof, scientific journal articles, and database entries (e.g., GENBANK®, UniprotKB, the NCBI RefSeq database, the Sequence Read Archive database, and the GreenGenes database, including all entries and annotations available therein) are incorporated herein by reference in their entireties to the extent that they supplement, explain, provide a background for, or teach methodology, techniques, and/or compositions employed herein.

COMPLETE REFERENCES

Abelson & Simon (1988a) *Methods in Enzymology*, Vol. 154, Academic Press Inc., New York, New York, United States of America.

Abelson & Simon (1988b) *Methods in Enzymology*, Vol. 155, Academic Press Inc., New York, New York, United States of America.

Amar et al. (2011) Intestinal mucosal adherence and translocation of commensal bacteria at the early onset of type 2 diabetes: molecular mechanisms and probiotic treatment. EMBO Mol Med 3:559-572.

Arrieta et al. (2015) Early infancy microbial and metabolic alterations affect risk of childhood asthma. Sci Transl Med 7:307ra152.

Benjamini & Hochberg (1995) Controlling the false discovery rate: a practical and powerful approach to multiple testing. J R Stat Soc Series B Stat Methodol 75:289-300.

Berkow et al., (1997) *The Merck Manual of Medical Information, Home ed*. Merck Research Laboratories, Whitehouse Station, New Jersey, United States of America.

Bessede et al. (2014) Aryl hydrocarbon receptor control of a disease tolerance defence pathway. Nature 511(7508): 184-190.

Biddle et al. (2013) Untangling the Genetic Basis of Fibrolytic Specialization by Lachnospiraceae and Ruminococcaceae in Diverse Gut Communities. Diversity 5(3): 627-640.

Brosseau & Moffett (2015) Functional and Genetic Analysis Identify a Role for Arabidopsis ARGONAUTES in Antiviral RNA Silencing. Plant Cell 27:1742-1754.

Caporaso et al. (2010a) QIIME allows analysis of high-throughput community sequencing data. Nat Methods 7:335-336.

Caporaso et al. (2010b) PyNAST: a flexible tool for aligning sequences to a template alignment. Bioinformatics 26:266-267.

Carbonell & Carrington (2015) Antiviral roles of plant ARGONAUTES. Curr Opin Plant Biol 27:111-117.

Chassaing & Gewirtz (2014) Gut microbiota, low-grade inflammation, and metabolic syndrome. Toxicol Pathol 42:49-53.

Chassaing et al. (2012) Gut microbiota drives metabolic disease in immunologically altered mice. Adv Immunol 116:93-112.

Claesson et al. (2012) Gut microbiota composition correlates with diet and health in the elderly. Nature 488:178-184.

Cotillard et al. (2013) Dietary intervention impact on gut microbial gene richness. Nature 500:585-588.

Deng et al. (2015) Enterobacteria-secreted particles induce production of exosome-like S1P-containing particles by intestinal epithelium to drive Th17-mediated tumorigenesis. Nat Commun 6:6956.

Deng et al. (2017) Broccoli-Derived Nanoparticle Inhibits Mouse Colitis by Activating Dendritic Cell AMP-Activated Protein Kinase. Mol Ther 25:1641-1654.

Desai et al. (2016) A Dietary Fiber-Deprived Gut Microbiota Degrades the Colonic Mucus Barrier and Enhances Pathogen Susceptibility. Cell 167:1339-1353 e21.

Dey et al. (2015) Regulators of gut motility revealed by a gnotobiotic model of diet-microbiome interactions related to travel. Cell 163:95-107.

Duch et al. (1998) Volatile anesthetics significantly suppress central and peripheral mammalian sodium channels. Toxicol Lett 100-101:255-263.

Ebadi (1998) *CRC Desk Reference of Clinical Pharmacology*. CRC Press, Boca Raton, Florida, United States of America.

Edgar (2010) Search and clustering orders of magnitude faster than BLAST. Bioinformatics 26:2460-2461.

Falci et al. (2015) *Lactobacillus rhamnosus* bacteremia in a kidney transplant recipient. Transpl Infect Dis 17:610-612.

Fatyol et al. (2016) Functional dissection of a plant Argonaute. Nucleic Acids Res 44:1384-1397.

Festing & Altman (2002) Guidelines for the design and statistical analysis of experiments using laboratory animals. ILAR Journal/National Research Council, Institute of Laboratory Animal Resources. 43(4):244-258.

Freireich et al., (1966) Quantitative comparison of toxicity of anticancer agents in mouse, rat, hamster, dog, monkey, and man. Cancer Chemother Rep. 50: 219-244.

Freshney (1987) *Culture of Animal Cells: A Manual of Basic Technique*, Alan R. Liss, Inc., New York, New York, United States of America.

Gait (1984) *Oligonucleotide Synthesis: A Practical Approach*. IRL Press at Oxford University Press, Oxford/New York, United States of America.

Garcia-Segura et al. (2013) The emerging role of MicroRNAs in the regulation of gene expression by nutrients. J Nutrigenet Nutrigenomics 6:16-31.

Glenwright et al. (2017) Structural basis for nutrient acquisition by dominant members of the human gut microbiota. Nature 541:407-411.

Glover & Hames (1985) *DNA Cloning: A Practical Approach* IRL Press at Oxford University Press, Oxford/New York, United States of America.

Glover & Hames (1995) *DNA Cloning: A Practical Approach, 2nd ed*. IRL Press at Oxford University Press, Oxford/New York, United States of America.

Goodman et al. (1996) *Goodman & Gilman's the Pharmacological Basis of Therapeutics, 9th ed*. McGraw-Hill Health Professions Division, New York, New York, United States of America.

Hames & Higgins (1984) *Transcription and Translation: A Practical Approach*. IRL Press at Oxford University Press, Oxford/New York, United States of America.

Hames & Higgins (1985) *Nucleic Acid Hybridization: A Practical Approach*. IRL Press at Oxford University Press, Oxford/New York, United States of America.

Hausser & Zavolan (2014) Identification and consequences of miRNA-target interactions—beyond repression of gene expression. Nat Rev Genet 15:599-612.

He et al. (2017) Anti-Infective Effect of Adhesive Probiotic *Lactobacillus* in Fish is Correlated with Their Spatial Distribution in the Intestinal Tissue. Scientific Reports 7(1): 13195.

Hess & Greenberg (2012) The role of nucleotides in the immune and gastrointestinal systems: potential clinical applications. Nutr Clin Pract 27:281-294.

Hildebrandt et al. (2009) High-fat diet determines the composition of the murine gut microbiome independently of obesity. Gastroenterology 137:1716-1724 e1-2.

Huttenhower et al. (2014) Inflammatory bowel disease as a model for translating the microbiome. Immunity 40:843-854.

IUPAC—IUB Commission on Bio-Chemical Nomenclature Symbols for Amino-Acid Derivatives and Peptides (1972) Recommendations (1971) Biochem 11(9):1726-1732.

Ju et al. (2013) Grape exosome-like nanoparticles induce intestinal stem cells and protect mice from DSS-induced colitis. Mol Ther 21:1345-1357.

Katzung (2001) *Basic & Clinical Pharmacology, 8th ed*. Lange Medical Books/McGraw-Hill Medical Pub. Division, New York, New York, United States of America.

Kim & Shin (2014) How to do random allocation (randomization). Clin Orthop Surg 6(1):103-109.

Kosuge et al. (1966) Microbial synthesis and degradation of indole-3-acetic acid. I. The conversion of L-tryptophan to indole-3-acetamide by an enzyme system from *Pseudomonas savastanoi*. The Journal of Biological Chemistry 241(16):3738-3744.

Le Roy et al. (2013) Intestinal microbiota determines development of non-alcoholic fatty liver disease in mice. Gut 62:1787-1794.

Letunic & Bork (2007) Interactive Tree Of Life (iTOL): an online tool for phylogenetic tree display and annotation. Bioinformatics 23:127-128.

Li et al. (2011) Exogenous stimuli maintain intraepithelial lymphocytes via aryl hydrocarbon receptor activation. Cell 147(3):629-640.

Liu et al. (2016) The Host Shapes the Gut Microbiota via Fecal MicroRNA. Cell Host Microbe 19:32-43.

Lukens et al. (2014) Dietary modulation of the microbiome affects autoinflammatory disease. Nature 516:246-249.

Maslowski & Mackay (2011) Diet, gut microbiota and immune responses. Nat Immunol 12:5-9.

Mayer & Walker (1987) Immunochemical Methods, in *Cell and Molecular Biology*, Academic Press, London, England.

Meini et al. (2015) Breakthrough *Lactobacillus rhamnosus* GG bacteremia associated with probiotic use in an adult patient with severe active ulcerative colitis: case report and review of the literature. Infection 43:777-781.

Miller & Calos (1987) *Gene Transfer Vectors For Mammalian Cells*, Cold Spring Harbor Laboratory, Cold Spring Harbor, New York, United States of America.

Miller et al. (2004) SOS response induction by beta-lactams and bacterial defense against antibiotic lethality. Science 305(5690), 1629-1631.

Monteleone et al. (2011) Aryl hydrocarbon receptor-induced signals up-regulate IL-22 production and inhibit inflammation in the gastrointestinal tract. Gastroenterology 141 (1):237-248.

Mu et al. (2014) Interspecies communication between plant and mouse gut host cells through edible plant derived exosome-like nanoparticles. Mol Nutr Food Res 58:1561-1573.

Muegge et al. (2011) Diet drives convergence in gut microbiome functions across mammalian phylogeny and within humans. Science 332:970-974.

Mukherji et al. (2011) MicroRNAs can generate thresholds in target gene expression. Nat Genet 43:854-859.

Murphy et al. (2008) Suppression of immediate-early viral gene expression by herpesvirus-coded microRNAs: implications for latency. Proc Natl Acad Sci USA 105: 5453-5458.

Patterson et al. (2016) Gut microbiota, obesity and diabetes. Postgrad Med J 92:286-300.

PCT International Patent Application Publication Nos. WO 93/25521; WO 98/47491.

Perbal (1984) *A Practical Guide To Molecular Cloning*. John Wiley & Sons, New York, New York, United States of America.

Pruitt et al. (2007) NCBI reference sequences (RefSeq): a curated non-redundant sequence database of genomes, transcripts and proteins. Nucleic Acids Res 35:D61-D65.

Record (2013) Exosome-like nanoparticles from food: protective nanoshuttles for bioactive cargo. Mol Ther 21:1294-1296.

Remington et al. (1975) *Remington's Pharmaceutical Sciences, 15th ed.* Mack Pub. Co., Easton, Pennsylvania, United States of America.

Rosselli et al. (2016) Direct 16S rRNA-seq from bacterial communities: a PCR-independent approach to simultaneously assess microbial diversity and functional activity potential of each taxon. Scientific Reports 6:32165.

Sambrook et al. (1989) *Molecular Cloning A Laboratory Manual, 2nd Ed*. Cold Spring Harbor Laboratory Press, Cold Spring Harbor, New York, United States of America, Chapters 16 and 17.

Schwarzer et al. (2016) *Lactobacillus plantarum* strain maintains growth of infant mice during chronic undernutrition. Science 351:854-857.

Schwertner et al. (2006) Variation in concentration and labeling of ginger root dietary supplements. Obstetrics and Gynecology 107(6): 1337-1343 .

Segers & Lebeer (2014) Towards a better understanding of *Lactobacillus rhamnosus* GG-host interactions. Microb Cell Fact 13 Suppl 1:S7.

Sonnenberg & Artis (2012) Innate lymphoid cell interactions with microbiota: implications for intestinal health and disease. Immunity 37(4):601-610.

Sonnenburg & Bäckhed (2016) Diet-microbiota interactions as moderators of human metabolism. Nature 535:56-64.

Sonnenburg et al. (2016) Diet-induced extinctions in the gut microbiota compound over generations. Nature 529:212-215.

Speight et al. (1997) *Avery's Drug Treatment: A Guide to the Properties, Choice, Therapeutic Use and Economic Value of Drugs in Disease Management, 4th ed*. Adis International, Auckland/Philadelphia.

Stutz (1958) Enzymatic Formation of Indole-3-Carboxaldehyde from Indole-3-Acetic Acid. Plant physiology. 33(3): 207-212.

Tang et al. (2017) Gut Microbiota in Cardiovascular Health and Disease. Circ Res 120:1183-1196.

Teng et al. (2016) Grapefruit-derived nanovectors deliver miR-18a for treatment of liver metastasis of colon cancer by induction of M1 macrophages. Oncotarget 7:25683-25697.

Teng et al. (2017) MVP-mediated exosomal sorting of miR-193a promotes colon cancer progression. Nat Commun 8:14448.

Tschop et al. (2009) Getting to the core of the gut microbiome. Nat Biotechnol 27:344-346.

U.S. Pat. Nos. 4,683,195; 4,839,177; 4,891,223; 5,234,933; 5,326,902; 5,397,574; 5,399,358; 5,399,359; 5,399,362; 5,419,917; 5,422,123; 5,456,921; 5,458,005; 5,458,887; 5,458,888; 5,464,633; 5,472,708; 5,512,297; 5,603,956; 5,725,883; 5,773,025; 5,824,638; 5,834,023; 5,837,379; 5,885,616; 5,897,876; 5,912,013; 5,916,595; 5,952,004; 6,004,582; 6,077,541; 6,096,340; 6,099,859; 6,099,862; 6,103,263; 6,106,862; 6,110,498; 6,180,082.

Usami et al. (2015) Gut microbiota and host metabolism in liver cirrhosis. World J Gastroenterol 21:11597-11608.

Varankovich et al. (2015) Probiotic-based strategies for therapeutic and prophylactic use against multiple gastrointestinal diseases. Front Microbiol 6:685.

Wang et al. (1998) Characterization of *Listeria monocytogenes* isolated from channel catfish (Ictalurus punctatus). Am J Vet Res 59:1125-1128.

Wang et al. (2013) Delivery of therapeutic agents by nanoparticles made of grapefruit-derived lipids. Nat Commun 4:1867.

Wang et al. (2014) Targeted drug delivery to intestinal macrophages by bioactive nanovesicles released from grapefruit. Mol Ther 22:522-534.

Webber & Clayton (2013). How pure are your vesicles? Journal of Extracellular Vesicles 2:1, 19861, DOI: 10.3402/jev.v2i0.19861.

Weir et al. (1986) *Handbook of Experimental Immunology, Volumes I-IV*, Blackwell Scientific Publications, Boston, Massachusetts, United States of America.

Xiang et al. (2011) miR-155 promotes macroscopic tumor formation yet inhibits tumor dissemination from mammary fat pads to the lung by preventing EMT. Oncogene 30:3440-3453.

Zhang & Wang (1998) Induction of cytokine messenger RNA transcripts in mouse macrophages by *Listeria monocytogenes* isolated from channel catfish. Am J Vet Res 59:717-721.

Zhang et al. (2012) Exogenous plant MIR168a specifically targets mammalian LDLRAP1: evidence of cross-kingdom regulation by microRNA. Cell Res 22:107-126.

Zhuang et al. (2015) Ginger-derived nanoparticles protect against alcohol-induced liver damage. J Extracell Vesicles 4:28713.

It will be understood that various details of the presently disclosed subject matter can be changed without departing from the scope of the subject matter disclosed herein. Furthermore, the foregoing description is for the purpose of illustration only, and not for the purpose of limitation.

TABLE 1

| Target | Forward Primer (5' to 3') | Reverse Primer (5' to 3') |
|---|---|---|
| osa-miR820a (SEQ ID NO: 141) | TCGGCCTCGTGGATGGAC; SEQ ID NO: 10 | Universal primer (QIAGEN) |
| ath-miR167a-5p (SEQ ID NO: 9) | TCGGCCTCGTGGATGGAC; SEQ ID NO: 11 | Universal primer (QIAGEN) |
| mtr-miR2627 (SEQ ID NO: 163) | TTTCGGTAGTTAACTGCTGAGG; SEQ ID NO: 12 | Universal primer (QIAGEN) |
| vvi-miR3634-3p (SEQ ID NO: 159) | TTTCCGACTCGCACTCATGC; SEQ ID NO: 13 | Universal primer (QIAGEN) |
| ath-miR842 (SEQ ID NO: 82) | TCATGGTCAGATCCGTCATC; SEQ ID NO: 14 | Universal primer (QIAGEN) |
| ppt-miR1028a-3p (SEQ ID NO: 144) | TGACATTGTAGATCTACGTGC; SEQ ID NO: 15 | Universal primer (QIAGEN) |
| osa-miR2865 (SEQ ID NO: 137) | CTCAGCAGTCGACTGTACC; SEQ ID NO: 16 | Universal primer (QIAGEN) |
| aly-miR163-3p.2 (SEQ ID NO: 52) | AATCGTTGAGGCTGAAGTCGT; SEQ ID NO: 17 | Universal primer (QIAGEN) |
| osa-miR166j-5p (SEQ ID NO: 136) | GAATGACGTCCGGTCTGAA; SEQ ID NO: 18 | Universal primer (QIAGEN) |
| esi-miR3463-5p (SEQ ID NO: 97) | TCATTGCTGGTGCTCGTTG; SEQ ID NO: 19 | Universal primer (QIAGEN) |
| aly-miR3447-5p (SEQ ID NO: 66) | CGTGACGAACATAATCAAACG; SEQ ID NO: 20 | Universal primer (QIAGEN) |
| esi-miR3469-3p (SEQ ID NO: 98) | GGAGAGTGGTCGGATTGTAG; SEQ ID NO: 21 | Universal primer (QIAGEN) |
| cre-miR1153-5p.2 (SEQ ID NO: 96) | AGTGCTGCTAGCAACTACAAG; SEQ ID NO: 22 | Universal primer (QIAGEN) |
| ath-miR827 (SEQ ID NO: 81) | GGTTAGATGACCATCAACAAACT; SEQ ID NO: 23 | Universal primer (QIAGEN) |
| mdo-miR-7267-3p (SEQ ID NO: 129) | CATCCAGCCATCCACCCCA; SEQ ID NO: 24 | Universal primer (QIAGEN) |
| ycnE | CAAGCAGTGGCATCACATAAC; SEQ ID NO: 25 | CGCCGAATAGTCCATACGAATA; SEQ ID NO: 26 |
| spaC | GTCCTTTGTGCCATGGTATTG; SEQ ID NO: 27 | TGCAGCACCTACAGGTTATC; SEQ ID NO: 28 |
| lexA | AGGATGAGGCAACGGTTAAA; SEQ ID NO: 29 | CGTGACACTTGGGAAGTACATA; SEQ ID NO: 30 |
| Bacteroidetes | CATGTGGTTTAATTCGATGAT; SEQ ID NO: 31 | AGCTGACGACAACCATGCAG; SEQ ID NO: 32 |
| *Clostridial* | GCACAAGCAGTGGAGT; SEQ ID NO: 33 | CTTCCTCCGTTTTGTCAA; SEQ ID NO: 34 |
| Bacteria | GCAGGCCTAACACATGCAAGTC; SEQ ID NO: 35 | TGCTGCCTCCCGTAGGAGT; SEQ ID NO: 36 |
| *Lactobacilli* | GCAGCAGTAGGGAATCTTCCA; SEQ ID NO: 37 | GCATTYCACCGCTACACATG; SEQ ID NO: 38 |
| *Enterobacteria* | ATGGCTGTCGTCAGCTCGT; SEQ ID NO: 39 | CCTACTTCTTTTGCAACCCACTC; SEQ ID NO: 40 |
| LGG-dnaJ | CAACCGGTCCATGAACCGT; SEQ ID NO: 41 | TACGGGGACTTGTACATCGT; SEQ ID NO: 42 |
| *Ruminococcaceae* | ACTGAGAGGTTGAACGGCCA; SEQ ID NO: 43 | CCTTTACACCCAGTAAWTCCGGA; SEQ ID NO: 44 |
| 16S Universal | CTCCTACGGGAGGCAGCAG; SEQ ID NO: 45 | GTATTACCGCGGCTGCTG; SEQ ID NO: 46 |

TABLE 2

List of GELN miRNAs Sequencing and Prediction Target Genes Expressed in LGG

| RNA ID | Read | miRNA seed | geneSymbol |
|---|---|---|---|
| bdi-miR166f (SEQ ID NO: 87) | 106427 | | |
| gma-miR166u (SEQ ID NO: 107) | 106425 | | |
| sbi-miR166k (SEQ ID NO: 153) | 106078 | TCGGACCA | LGG_RS06155, LGG_RS03565, LGG_RS11270, LGG_RS07215, LGG_RS06270, LGG_RS12435 |
| aly-miR166a-3p (SEQ ID NO: 54) | 105150 | TCGGACCA | LGG_RS06155, LGG_RS03565, LGG_RS11270, LGG_RS07215, LGG_RS06270, LGG_RS12435 |
| | | GGAATGTT | LGG_RS10645, LGG_RS05940, LGG_RS07060, LGG_RS02955, LGG_RS11535, LGG_RS13190, LGG_RS11335, LGG_RS10735, LGG_RS00325, LGG_RS07000 |
| gma-miR166p-3p (SEQ ID NO: 106) | 105146 | TCGGACCA | LGG_RS06155, LGG_RS03565, LGG_RS11270, LGG_RS07215, LGG_RS06270, LGG_RS12435 |
| bdi-miR166e-3p (SEQ ID NO: 86) | 105109 | CTCGGACC | LGG_RS06155, LGG_RS11175, LGG_RS06270 |
| gma-miR166m (SEQ ID NO: 105) | 105107 | CGGACCAG | LGG_RS06155, LGG_RS01800, LGG_RS05745, LGG_RS11270, LGG_RS00620 |
| aly-miR159a-3p (SEQ ID NO: 49) | 23005 | TTTGGATT | LGG_RS02470, LGG_RS03685, LGG_RS02890, LGG_RS03025, LGG_RS05725, LGG_RS11920, LGG_RS01630, LGG_RS09305, LGG_RS12940, LGG_RS03740, LGG_RS01295, LGG_RS01715, LGG_RS06325, LGG_RS13135, prsA, LGG_RS00840, rplL, LGG_RS12340, LGG_RS04900, LGG_RS14025, LGG_RS04355, LGG_RS02595, LGG_RS07120, LGG_RS13640, LGG_RS04340, LGG_RS05150 |
| ptc-miR396g-5p (SEQ ID NO: 152) | 5104 | | |
| mtr-miR166c (SEQ ID NO: 130) | 2049 | TCGGACCA | LGG_RS06155, LGG_RS03565, LGG_RS11270, LGG_RS07215, LGG_RS06270, LGG_RS12435 |
| mdo-miR-7267-3p (SEQ ID NO: 129) | 2348 | TCCAGCCA | ycnE |
| aly-miR396a-5p (SEQ ID NO: 72) | 1364 | | |
| gma-miR396h (SEQ ID NO: 120) | 1364 | TCCACAGC | LGG_RS00465, LGG_RS04485, LGG_RS08185, LGG_RS09775, LGG_RS13140, LGG_RS03370 (lexA), LGG_RS07330, LGG_RS05410, LGG_RS13665 |
| gma-miR396e (SEQ ID NO: 119) | 1357 | TTCCACAG | LGG_RS00465, LGG_RS05410, LGG_RS10455, LGG_RS12210, LGG_RS03370 (lexA), LGG_RS13140, LGG_RS14080, LGG_RS13080 |
| gma-miR6300 (SEQ ID NO: 124) | 1013 | GTCGTTGT | LGG_RS07225, LGG_RS05405, LGG_RS06685, LGG_RS06430, LGG_RS01040, LGG_RS01195, LGG_RS02835, LGG_RS09730, gyrB, LGG_RS02980, LGG_RS04240, LGG_RS00775, LGG_RS00620, LGG_RS11090, LGG_RS07285, LGG_RS12015, |
| aly-miR319a-3p (SEQ ID NO: 65) | 989 | TTGGACTG | LGG_RS00035, LGG_RS12535, LGG_RS02955, LGG_RS01990, LGG_RS02815, LGG_RS04365, LGG_RS09105, LGG_RS00195, LGG_RS05225, LGG_RS11605 |
| gma-miR319a (SEQ ID NO: 114) | 989 | TTGGACTG | LGG_RS00035, LGG_RS12535, LGG_RS02955, LGG_RS01990, LGG_RS02815, LGG_RS04365, LGG_RS09105, LGG_RS00195, LGG_RS05225, LGG_RS11605 |
| ppt-miR319c (SEQ ID NO: 146) | 988 | CTTGGACT | LGG_RS05410, LGG_RS12535, LGG_RS11285, LGG_RS11605 |
| ppt-miR319 (SEQ ID NO: 145) | 984 | CTTGGACT | LGG_RS05410, LGG_RS12535, LGG_RS11285, LGG_RS11605 |
| gma-miR4995 (SEQ ID NO: 122) | 620 | AGGCAGTG | dnaE, LGG_RS08045, LGG_RS10025, LGG_RS10010, LGG_RS11275 |
| ptc-miR319e (SEQ ID NO: 151) | 580 | TTGGACTG | LGG_RS00035, LGG_RS12535, LGG_RS02955, LGG_RS01990, LGG_RS02815, LGG_RS04365, LGG_RS09105, LGG_RS00195, LGG_RS05225, LGG_RS11605 |

TABLE 2-continued

List of GELN miRNAs Sequencing and Prediction Target Genes Expressed in LGG

| RNA ID | Read | miRNA seed | geneSymbol |
|---|---|---|---|
| gma-miR319p (SEQ ID NO: 115) | 456 | TTTTGGAC | LGG_RS01265, LGG_RS09995, LGG_RS13625, LGG_RS05775, LGG_RS11230, LGG_RS02955, LGG_RS04365, LGG_RS01825, LGG_RS06470, LGG_RS07500, LGG_RS08815, LGG_RS06440, LGG_RS02795, LGG_RS09480, LGG_RS01295, LGG_RS03625, |
| mtr-miR319c-3p (SEQ ID NO: 135) | 411 | TTGGACTG | LGG_RS00035, LGG_RS12535, LGG_RS02955, LGG_RS01990, LGG_RS02815, LGG_RS04365, LGG_RS09105, LGG_RS00195, LGG_RS05225, LGG_RS11605 |
| aly-miR166a-5p (SEQ ID NO: 55) | 300 | | |
| aly-miR168a-5p (SEQ ID O: 59) | 170 | TCGCTTGG | LGG_RS02845, LGG_RS02110, LGG_RS06350, LGG_RS01460, LGG_RS10515, LGG_RS12920, LGG_RS09545, LGG_RS02935, LGG_RS07040, rpsP, LGG_RS13195, LGG_RS05540, LGG_RS12590, LGG_RS10125, LGG_RS13520, LGG_RS00705 |
| gma-miR168b (SEQ ID NO: 109) | 169 | TCGCTTGG | LGG_RS02845, LGG_RS02110, LGG_RS06350, LGG_RS01460, LGG_RS10515, LGG_RS12920, LGG_RS09545, LGG_RS02935, LGG_RS07040, rpsP, LGG_RS13195, LGG_RS05540, |
| aly-miR396b-5p (SEQ ID NO: 73) | 108 | TTCCACAG | LGG_RS00465, LGG_RS05410, LGG_RS10455, LGG_RS12210, LGG_RS13140, LGG_RS14080, LGG_RS13080 |
| aly-miR167d-5p (SEQ ID NO: 57) | 65 | TGAAGCTG | LGG_RS11575, LGG_RS12235, gyrB, LGG_RS02310, LGG_RS11535, LGG_RS09285, LGG_RS11155, LGG_RS08775, LGG_RS06550, LGG_RS01065, LGG_RS00705, LGG_RS02270, LGG_RS10480, LGG_RS05250, LGG_RS05220, LGG_RS10775, LGG_RS05425, LGG_RS12180, LGG_RS07225 |
| bdi-miR444a (SEQ ID NO: 95) | 65 | | |
| gma-miR167c (SEQ ID NO: 108) | 65 | TGAAGCTG | LGG_RS11575, LGG_RS12235, gyrB, LGG_RS02310, LGG_RS11535, LGG_RS09285, LGG_RS11155, LGG_RS08775, LGG_RS06550, LGG_RS01065, LGG_RS00705, LGG_RS02270, |
| aly-miR156a-5p (SEQ ID NO: 164) | 62 | TGACAGAA | LGG_RS02800, LGG_RS09920, LGG_RS03405, LGG_RS08055, LGG_RS12775 |
| stu-miR156f-5p (SEQ ID NO: 156) | 62 | CTGACAGA | LGG_RS09920, LGG_RS12580, LGG_RS10675, LGG_RS07085, LGG_RS09415 |
| osa-miR396d (SEQ ID NO: 139) | 51 | TCCACAGG | LGG_RS13640, LGG_RS14080, LGG_RS11745, LGG_RS02035 |
| aly-miR393a-5p (SEQ ID NO: 68) | 44 | | |
| bdi-miR171f (SEQ ID NO: 90) | 44 | | |
| bdi-miR393a (SEQ ID NO: 91) | 44 | | |
| gma-miR393h (SEQ ID NO: 117) | 44 | | |
| mtr-miR166e-5p (SEQ ID NO: 131) | 36 | | |
| ppe-miR393a (SEQ ID NO: 143) | 36 | | |
| aly-miR162a-3p (SEQ ID NO: 51) | 28 | TCGATAAA | LGG_RS03185, LGG_RS12205, LGG_RS06555, LGG_RS12265, LGG_RS03790, LGG_RS03815, LGG_RS13785, LGG_RS11805, LGG_RS06195, LGG_RS09865, LGG_RS12355, LGG_RS13650, LGG_RS13365, LGG_RS07220, LGG_RS06725, LGG_RS06810, LGG_RS07830, LGG_RS02835, LGG_RS09355, LGG_RS01350, LGG_RS12790, LGG_RS10845, LGG_RS11495, LGG_RS02890, LGG_RS00030, LGG_RS07470 |
| gma-miR162a (SEQ ID NO: 103) | 28 | TCGATAAA | LGG_RS03185, LGG_RS12205, LGG_RS06555, LGG_RS12265, LGG_RS03790, LGG_RS03815, LGG_RS13785, LGG_RS11805, LGG_RS06195, LGG_RS09865, LGG_RS12355, LGG_RS13650, LGG_RS13365, LGG_RS07220, LGG_RS06725, LGG_RS06810, |

TABLE 2-continued

List of GELN miRNAs Sequencing and Prediction Target Genes Expressed in LGG

| RNA ID | Read | miRNA seed | geneSymbol |
|---|---|---|---|
| | | | LGG_RS07830, LGG_RS02835, LGG_RS09355, LGG_RS01350, LGG_RS12790, LGG_RS10845, LGG_RS11495, LGG_RS02890, LGG_RS00030, LGG_RS07470 |
| ath-miR156j (SEQ ID NO: 78) | 23 | TGACAGAA | LGG_RS02800, LGG_RS09920, LGG_RS03405, LGG_RS08055, LGG_RS12775 |
| bdi-miR156a (SEQ ID NO: 84) | 23 | TGACAGAA | LGG_RS02800, LGG_RS09920, LGG_RS03405, LGG_RS08055, LGG_RS12775 |
| gma-miR156aa (SEQ ID NO: 100) | 23 | | |
| gma-miR156f (SEQ ID NO: 101) | 23 | TTGACAGA | LGG_RS06625, LGG_RS09505, LGG_RS09410, LGG_RS07140, LGG_RS10925, LGG_RS11095, LGG_RS09160, LGG_RS00700, LGG_RS03405, LGG_RS08950, LGG_RS13575 |
| mdm-miR156t (SEQ ID NO: 125) | 23 | TTGACAGA | LGG_RS06625, LGG_RS09505, LGG_RS09410, LGG_RS07140, LGG_RS10925, LGG_RS11095, LGG_RS09160, LGG_RS00700, LGG_RS03405, LGG_RS08950, LGG_RS13575 |
| ptc-miR156k (SEQ ID NO: 150) | 23 | TGACAGAA | LGG_RS02800, LGG_RS09920, LGG_RS03405, LGG_RS08055, LGG_RS12775 |
| aly-miR157a-5p (SEQ ID NO: 47) | 22 | TTGACAGA | LGG_RS06625, LGG_RS09505, LGG_RS09410, LGG_RS07140, LGG_RS10925, LGG_RS11095, LGG_RS09160, LGG_RS00700, LGG_RS03405, LGG_RS08950, LGG_RS13575 |
| aly-miR157d-5p (SEQ ID NO: 48) | 22 | TGACAGAA | LGG_RS02800, LGG_RS09920, LGG_RS03405, LGG_RS08055, LGG_RS12775 |
| aly-miR858-5p (SEQ ID NO: 77) | 22 | TTTCGTTG | LGG_RS13805, LGG_RS05415, LGG_RS11710, LGG_RS12050, LGG_RS10665, LGG_RS12505, LGG_RS08500, LGG_RS00730, murQ, LGG_RS08240, LGG_RS01980, LGG_RS00695, LGG_RS02540, LGG_RS02910, LGG_RS03260, LGG_RS12850, LGG_RS05500, LGG_RS04645, LGG_RS11495, LGG_RS08430, LGG_RS06370, LGG_RS05850, LGG_RS01705, LGG_RS08285, LGG_RS12830, LGG_RS00300, LGG_RS01120 |
| ath-miR858b (SEQ ID NO: 83) | 22 | TTCGTTGT | LGG_RS09405, LGG_RS02195, LGG_RS07305, LGG_RS11710, LGG_RS01330, LGG_RS09730, LGG_RS12050, LGG_RS00675, gatC, LGG_RS08670, LGG_RS03260, LGG_RS02940, LGG_RS09245, LGG_RS12850, LGG_RS10565, LGG_RS10780, LGG_RS00695, LGG_RS05850, LGG_RS00070, LGG_RS07700, LGG_RS09940, LGG_RS03150 |
| gma-miR156g (SEQ ID NO: 102) | 22 | | |
| zma-miR396g-3p (SEQ ID NO: 162) | 18 | GTTCAAGA | LGG_RS03495, LGG_RS03610, LGG_RS06280, LGG_RS04310, LGG_RS10225, LGG_RS05095, LGG_RS00705, LGG_RS00840, LGG_RS07120, LGG_RS11430, LGG_RS09480, LGG_RS06025, LGG_RS10100, LGG_RS02095 |
| gma-miR5368 (SEQ ID NO: 123) | 17 | | |
| aly-miR168a-3p (SEQ ID NO: 58) | 16 | | |
| aly-miR390a-5p (SEQ ID NO: 67) | 16 | | |
| gma-miR390e (SEQ ID NO: 116) | 16 | | |
| mdm-miR171a (SEQ ID NO: 126) | 15 | | |
| aly-miR395d-3p (SEQ ID NO: 70) | 13 | | |
| bdi-miR395a (SEQ ID NO: 92) | 13 | | |

TABLE 2-continued

List of GELN miRNAs Sequencing and Prediction Target Genes Expressed in LGG

| RNA ID | Read | miRNA seed | geneSymbol |
| --- | --- | --- | --- |
| mtr-miR171b (SEQ ID NO: 132) | 13 | | |
| aly-miR171a-3p (SEQ ID NO: 61) | 11 | | |
| gma-miR171k-3p (SEQ ID NO: 110) | 11 | | |
| zma-miR171a-3p (SEQ ID NO: 160) | 11 | | |
| aly-miR394a-5p (SEQ ID NO: 69) | 10 | | |
| mtr-miR171e-3p (SEQ ID NO: 133) | 9 | | |
| aly-miR845b-3p (SEQ ID NO: 76) | 8 | | |
| mdm-miR535a (SEQ ID NO: 128) | 8 | TGACAACG | LGG_RS09790, LGG_RS06585, LGG_RS06945, LGG_RS09725, LGG_RS13375, LGG_RS01410, LGG_RS10525, LGG_RS04970, LGG_RS14035, LGG_RS09975, LGG_RS10755, LGG_RS11480, LGG_RS09945, LGG_RS12925, LGG_RS08995, LGG_RS05915, LGG_RS03160, LGG_RS09175, LGG_RS08590, LGG_RS01255, LGG_RS04460, LGG_RS09535, LGG_RS01145, LGG_RS06005, |
| aly-miR167a-5p (SEQ ID NO: 56) | 6 | GAAGCTGC | LGG_RS11575, LGG_RS12235, gyrB, LGG_RS02310, LGG_RS11535, LGG_RS09285, LGG_RS11155, LGG_RS08775, LGG_RS06550, LGG_RS01065, LGG_RS00705, LGG_RS02270, LGG_RS10480, LGG_RS05250, LGG_RS05220, LGG_RS10775, LGG_RS05425, LGG_RS12180, LGG_RS02140, LGG_RS07225 |
| aly-miR396a-3p (SEQ ID NO: 71) | 6 | GTTCAATA<br><br>TTCCACAG | LGG_RS12420, LGG_RS02535, LGG_RS08195, LGG_RS10710, LGG_RS08545, LGG_RS08335, LGG_RS00455, LGG_RS09970, LGG_RS05700, LGG_RS12050, LGG_RS10780, LGG_RS11275, LGG_RS00465, LGG_RS05410, LGG_RS10455, LGG_RS12210, LGG_RS13140, LGG_RS14080, LGG_RS13080 |
| gma-miR396a-3p (SEQ ID NO: 118) | 6 | TTCAATAA | LGG_RS02350, LGG_RS02535, LGG_RS10535, LGG_RS12985, LGG_RS01820, LGG_RS05700, LGG_RS08335, asnC, LGG_RS08295, LGG_RS07730, gyrB, LGG_RS03185, LGG_RS05145, LGG_RS01360, LGG_RS12050, LGG_RS06205, LGG_RS10710, LGG_RS03105, LGG_RS08315, LGG_RS11275, LGG_RS12025, LGG_RS12835, LGG_RS13550, LGG_RS12020, LGG_RS05510, LGG_RS09630, LGG_RS01660, LGG_RS01085, LGG_RS03245, LGG_RS00695, LGG_RS07815, LGG_RS01675, |
| osa-miR396a-3p (SEQ ID NO: 138) | 6 | GTTCAATA | LGG_RS12420, LGG_RS02535, LGG_RS08195, LGG_RS10710, LGG_RS08545, LGG_RS08335, LGG_RS00455, LGG_RS09970, LGG_RS05700, LGG_RS12050, LGG_RS10780, LGG_RS11275, LGG_RS08190, glpK, LGG_RS09835, LGG_RS01325, LGG_RS12760, LGG_RS12520, LGG_RS12550, LGG_RS09430, LGG_RS07815, LGG_RS03040, LGG_RS02480, LGG_RS12615, LGG_RS09610 |
| bdi-miR160f (SEQ ID NO: 85) | 5 | | |
| bdi-miR398a (SEQ ID NO: 94) | 5 | TGTGTTCT | LGG_ RS05400, LGG_RS03075, LGG_RS05295, LGG_RS05260, LGG_ RS12015, LGG_RS07380, LGG_RS03510, LGG_RS11880, LGG_ RS05920 |
| aly-miR160a-5p (SEQ ID NO: 50) | 4 | | |
| aly-miR408-3p (SEQ ID NO: 75) | 4 | | |
| gma-miR408d (SEQ ID NO: 121) | 4 | | |
| ppt-miR408b (SEQ ID NO: 147) | 4 | | |

TABLE 2-continued

List of GELN miRNAs Sequencing and Prediction Target Genes Expressed in LGG

| RNA ID | Read | miRNA seed | geneSymbol |
|---|---|---|---|
| aly-miR164a-5p (SEQ ID NO: 53) | 3 | TGGAGAAG | LGG_RS06440, LGG_RS09845, LGG_RS12955 |
| aly-miR172a-3p (SEQ ID NO: 63) | 3 | | |
| aly-miR172e-3p (SEQ ID NO: 64) | 3 | | |
| ath-miR172e-3p (SEQ ID NO: 79) | 3 | | |
| gma-miR164b (SEQ ID NO: 104) | 3 | | |
| gma-miR172c (SEQ ID NO: 111) | 3 | | |
| gma-miR172f (SEQ ID NO: 112) | 3 | | |
| gma-miR172k (SEQ ID NO: 113) | 3 | | |
| sbi-miR172b (SEQ ID NO: 155) | 3 | | |
| stu-miR172c-3p (SEQ ID NO: 157) | 3 | | |
| mtr-miR319a-5p (SEQ ID NO: 134) | 2 | | |
| aly-miR169h-5p (SEQ ID NO: 60) | 1 | | |
| aly-miR171b-3p (SEQ ID NO: 62) | 1 | | |
| aly-miR397a-5p (SEQ ID NO: 74) | 1 | | |
| ath-miR5658 (SEQ ID NO: 80) | 1 | | |
| bdi-miR169h-5p (SEQ ID NO: 88) | 1 | | |
| bdi-miR171b (SEQ ID NO: 89) | 1 | | |
| bdi-miR397b-5p (SEQ ID NO: 93) | 1 | | |
| gma-miR1511 (SEQ ID NO: 99) | 1 | | |
| mdm-miR397a (SEQ ID NO: 127) | 1 | | |
| osa-miR5523 (SEQ ID NO: 140) | 1 | | |
| ppe-miR169f (SEQ ID NO: 142) | 1 | | |
| ppt-miR477a-5p (SEQ ID NO: 148) | 1 | | |
| ppt-miR477h (SEQ ID NO: 149) | 1 | | |

TABLE 2-continued

List of GELN miRNAs Sequencing and Prediction Target Genes Expressed in LGG

| RNA ID | Read | miRNA seed | geneSymbol |
|---|---|---|---|
| sbi-miR169d-5p (SEQ ID NO: 154) | 1 | | |
| zma-miR171b-3p (SEQ ID NO: 161) | 1 | | |

TABLE 3

Predicted Potential Gut Bacteria mRNA Targeted by GELN miRNAs

| Bacterial Strain | Number of Potential mRNA Targets per Seed Length | |
|---|---|---|
| | 7-mer | 8-mer |
| *Lactobacillus rhamnosus* | 956 | 323 |
| *Lactobacillus ruminis* | 463 | 251 |
| *Prevotella melaninogenica* | 715 | 269 |
| *Helicobacter pylori* | 354 | 179 |
| *Ruminococcus bicirculans* | 829 | 317 |
| *Eubacterium rectale* | 816 | 359 |
| *Enterococcus faecalis* | 443 | 531 |
| *Escherichia coli* | 1392 | 450 |
| *Clostridium perfringens* | 140 | 221 |
| *Bacteroides fragilis* | 1329 | 524 |
| *Akkermansia muciniphila* | 834 | 284 |

TABLE 4

Gut Microbiota Composition Analyzed with 16S rRNA Sequencing

| Taxonomy | C57BL/6 Mouse Bacterial Percentage (%; n = 5) | | | | | | | | | |
|---|---|---|---|---|---|---|---|---|---|---|
| | PBS1 | PBS2 | PBS3 | PBS4 | PBS5 | GELNs1 | GELNs2 | GELNs3 | GELNs4 | GELNs5 |
| Unassigned; Other; Other; Other; Other | 2.90 | 3.89 | 2.90 | 4.27 | 7.06 | 4.30 | 4.50 | 3.50 | 6.60 | 4.40 |
| k_Bacteria; p_Bacteroidetes; c_Bacteroidia; o_Bacteroidales; Other | 0.20 | 0.00 | 0.10 | 1.93 | 1.23 | 1.00 | 0.90 | 0.10 | 2.42 | 1.10 |
| k_Bacteria; p_Bacteroidetes; c_Bacteroidia; o_Bacteroidales; f_Bacteroidaceae | 0.20 | 0.78 | 0.50 | 4.98 | 4.03 | 2.00 | 1.50 | 0.40 | 2.20 | 2.10 |
| k_Bacteria; p_Bacteroidetes; c_Bacteroidia; o_Bacteroidales; f_Porphyromonadaceae | 0.20 | 0.22 | 0.00 | 1.93 | 1.90 | 0.90 | 0.50 | 0.70 | 1.54 | 0.00 |
| k_Bacteria; p_Bacteroidetes; c_Bacteroidia; o_Bacteroidales; f_Prevotellaceae | 1.10 | 3.77 | 1.60 | 0.00 | 0.00 | 5.60 | 4.80 | 3.80 | 0.00 | 0.00 |
| k_Bacteria; p_Bacteroidetes; c_Bacteroidia; o_Bacteroidales; f_Rikenellaceae | 3.70 | 2.00 | 3.40 | 3.55 | 3.47 | 1.60 | 2.00 | 1.20 | 1.54 | 0.00 |
| k_Bacteria; p_Bacteroidetes; c_Bacteroidia; o_Bacteroidales; f_S24-7 | 17.40 | 31.52 | 17.30 | 12.80 | 23.08 | 41.60 | 52.30 | 46.90 | 34.22 | 54.30 |
| k_Bacteria; p_Bacteroidetes; c_Bacteroidia; o_Bacteroidales; f_[Odoribacteraceae] | 0.90 | 0.89 | 0.90 | 11.07 | 5.60 | 0.20 | 0.50 | 0.40 | 5.83 | 0.00 |
| k_Bacteria; p_Bacteroidetes; c_Bacteroidia; o_Bacteroidales; f_[Paraprevotellaceae] | 0.10 | 0.22 | 0.20 | 0.00 | 0.00 | 0.60 | 0.60 | 0.70 | 0.00 | 0.00 |
| k_Bacteria; p_Deferribacteres; c_Deferribacteres; o_Deferribacterales; f_Deferribacteraceae | 1.50 | 0.67 | 1.40 | 0.20 | 0.11 | 0.30 | 0.10 | 0.70 | 0.33 | 0.00 |
| k_Bacteria; p_Firmicutes; c_Bacilli; o_Lactobacillales; f_Lactobacillaceae | 0.20 | 0.50 | 0.20 | 0.10 | 0.22 | 26.90 | 23.50 | 33.10 | 20.69 | 19.80 |
| k_Bacteria; p_Firmicutes; c_Clostridia; o_Clostridiales; Other | 39.80 | 31.30 | 33.00 | 25.59 | 22.18 | 2.90 | 1.00 | 1.30 | 9.57 | 4.40 |
| k_Bacteria; p_Firmicutes; c_Clostridia; o_Clostridiales; f_Clostridiaceae | 16.80 | 14.87 | 21.50 | 20.72 | 11.32 | 2.00 | 1.00 | 1.20 | 0.11 | 0.70 |
| k_Bacteria; p_Firmicutes; c_Clostridia; o_Clostridiales; f_Dehalobacteriaceae | 0.00 | 0.11 | 0.20 | 0.00 | 0.00 | 0.10 | 0.00 | 0.00 | 0.11 | 0.00 |
| k_Bacteria; p_Firmicutes; c_Clostridia; o_Clostridiales; f_Lachnospiraceae | 4.10 | 3.00 | 3.40 | 0.51 | 2.45 | 1.70 | 0.50 | 0.50 | 1.87 | 2.50 |
| k_Bacteria; p_Firmicutes; c_Clostridia; o_Clostridiales; f_Peptostreptococcaceae | 0.00 | 0.00 | 0.00 | 0.30 | 0.34 | 0.00 | 0.00 | 0.00 | 0.44 | 0.40 |
| k_Bacteria; p_Firmicutes; c_Clostridia; o_Clostridiales; f_Ruminococcaceae | 7.20 | 4.44 | 9.30 | 4.67 | 12.66 | 4.50 | 3.00 | 2.60 | 4.07 | 6.40 |
| k_Bacteria; p_Firmicutes; c_Clostridia; o_Clostridiales; f_[Mogibacteriaceae] | 0.00 | 0.11 | 0.00 | 0.00 | 0.00 | 0.00 | 0.00 | 0.00 | 0.20 | 0.00 |
| k_Bacteria; p_Firmicutes; c_Erysipelotrichi; o_Erysipelotrichales; f_Erysipelotrichaceae | 0.00 | 0.00 | 0.00 | 1.32 | 1.34 | 0.10 | 0.00 | 0.00 | 2.86 | 0.50 |

TABLE 4-continued

Gut Microbiota Composition Analyzed with 16S rRNA Sequencing

| | | | | | | | | | | |
|---|---|---|---|---|---|---|---|---|---|---|
| k_Bacteria; p_Proteobacteria; c_Betaproteobacteria; o_Burkholderiales; f_Alcaligenaceae | 0.10 | 0.44 | 0.41 | 0.00 | 0.00 | 1.90 | 1.00 | 1.30 | 2.31 | 2.40 |
| k_Bacteria; p_Proteobacteria; c_Deltaproteobacteria; o_Desulfovibrionales; f_Desulfovibrionaceae | 0.70 | 0.56 | 0.70 | 1.83 | 1.23 | 0.20 | 0.80 | 0.50 | 1.32 | 0.00 |
| k_Bacteria; p_Proteobacteria; c_Epsilonproteobacteria; o_Campylobacterales; f_Helicobacteraceae | 2.30 | 0.47 | 2.40 | 0.41 | 0.56 | 0.80 | 0.10 | 0.70 | 0.44 | 0.00 |
| k_Bacteria; p_TM7; c_TM7-3; o_CW040; f_F16 | 0.30 | 0.00 | 0.20 | 0.71 | 0.11 | 0.20 | 0.60 | 0.10 | 0.66 | 0.00 |
| k_Bacteria; p_Tenericutes; c_Mollicutes; o_Mycoplasmatales; f_Mycoplasmataceae | 0.00 | 0.00 | 0.00 | 2.03 | 0.34 | 0.10 | 0.00 | 0.00 | 0.00 | 0.00 |

| | Human Bacterial Percentage (%, n = 3) | | | | | |
|---|---|---|---|---|---|---|
| Taxonomy | NaCl1 | NaCl2 | NaCl3 | GELNs1 | GELNs2 | GELNs3 |
| f_Fusobacteriaceae | 0.00 | 0.00 | 0.00 | 0.00 | 5.75 | 0.00 |
| f_unidentified | 0.33 | 0.05 | 0.75 | 0.14 | 0.00 | 0.61 |
| f_Peptococcaceae | 0.04 | 0.00 | 0.23 | 0.00 | 0.00 | 0.00 |
| f_Streptococcaceae | 0.01 | 0.89 | 0.28 | 0.78 | 0.00 | 0.01 |
| f_Family_XIII | 0.11 | 0.11 | 0.05 | 0.01 | 0.01 | 0.03 |
| f_Victivallaceae | 0.12 | 0.00 | 0.00 | 0.00 | 0.00 | 0.01 |
| f_Rikenellaceae | 4.07 | 1.27 | 5.71 | 0.42 | 0.28 | 2.98 |
| f_Alcaligenaceae | 0.37 | 0.95 | 0.86 | 0.29 | 1.15 | 0.84 |
| f_Acidaminococcaceae | 0.53 | 0.66 | 2.40 | 1.03 | 1.19 | 0.41 |
| f_Bifidobacteriaceae | 0.04 | 0.00 | 0.02 | 0.05 | 0.02 | 1.42 |
| f_Clostridiales_vadinBB60 | 0.41 | 0.00 | 0.01 | 0.01 | 0.00 | 0.00 |
| f_Porphyromonadaceae | 5.60 | 0.91 | 4.34 | 1.65 | 1.64 | 8.27 |
| f_Christensenellaceae | 2.32 | 0.58 | 2.28 | 0.07 | 0.00 | 0.12 |
| f_Lachnospiraceae | 10.46 | 12.31 | 15.14 | 10.60 | 3.72 | 12.37 |
| f_Syergistaceae | 0.11 | 0.08 | 0.07 | 0.01 | 0.00 | 0.01 |
| f_Erysipelotrichaceae | 0.31 | 0.63 | 0.05 | 0.22 | 0.06 | 0.15 |
| f_Lactobacillaceae | 0.14 | 0.25 | 0.00 | 19.66 | 8.46 | 13.44 |
| f_Enterococcaceae | 0.01 | 0.01 | 0.00 | 0.00 | 0.00 | 0.00 |
| f_Bacteroidaceae | 11.86 | 24.54 | 9.67 | 17.04 | 53.24 | 30.89 |
| f_Verrucomicrobiaceae | 0.00 | 0.00 | 0.17 | 0.00 | 0.00 | 0.21 |
| f_Coriobacteriaceae | 2.39 | 2.37 | 2.87 | 0.08 | 0.07 | 0.47 |
| f_Actinomycetaceae | 0.00 | 0.01 | 0.04 | 0.02 | 0.00 | 0.00 |
| f_Peptostreptococcaceae | 1.14 | 0.28 | 0.05 | 0.19 | 0.00 | 0.46 |
| f_Ruminococcaceae | 55.18 | 52.47 | 48.86 | 10.11 | 1.60 | 11.81 |
| f_Oxalobacteraceae | 0.01 | 0.00 | 0.00 | 0.01 | 0.00 | 0.00 |
| f_Desulfovibrionaceae | 0.52 | 0.42 | 0.34 | 0.19 | 0.39 | 0.30 |
| f_Enterobacteriaceae | 0.35 | 0.22 | 0.53 | 0.02 | 0.10 | 3.72 |
| f_Veillonellaceae | 0.39 | 0.00 | 1.40 | 1.78 | 7.47 | 5.37 |
| f_Family_XI | 0.00 | 0.01 | 0.00 | 0.00 | 0.00 | 0.00 |
| f_Pasteurellaceae | 0.01 | 0.00 | 0.06 | 0.64 | 0.00 | 0.01 |
| f_Bacteroidales_S24-7 | 1.22 | 0.23 | 0.33 | 2.46 | 1.84 | 3.51 |
| f_P5D1-392 | 0.00 | 0.00 | 0.00 | 0.02 | 0.00 | 0.00 |
| f_Prevotellaceae | 1.77 | 0.66 | 3.35 | 32.49 | 13.00 | 1.65 |
| f_Clostridiaceae_1 | 0.14 | 0.08 | 0.11 | 0.02 | 0.00 | 0.04 |

*Human fecal samples from 30 control (0.9% NaCl) and 28 GELNs treatment were pooled into three groups respectively

TABLE 5

Gut Microbiota Composition After ELN Uptake Based on Analysis with 16S rRNA Sequencing

| | ELNs uptake Bacteria (%, n = 5) Ginger | | | | |
|---|---|---|---|---|---|
| Taxonomy | 1 | 2 | 3 | 4 | 5 |
| Unassigned; Other; Other; Other; Other | 4.40 | 4.00 | 2.63 | 4.77 | 5.39 |
| k_Bacteria; p_Bacteroidetes; c_Bacteroidia; o_Bacteroidales; Other | 0.30 | 0.20 | 0.09 | 2.19 | 1.26 |
| k_Bacteria; p_Bacteroidetes; c_Bacteroidia; o_Bacteroidales; f_Bacteroidaceae | 0.00 | 0.20 | 0.45 | 1.62 | 1.53 |
| k_Bacteria; p_Bacteroidetes; c_Bacteroidia; o_Bacteroidales; f_Porphyromonadaceae | 0.00 | 0.00 | 0.09 | 1.62 | 1.80 |
| k_Bacteria; p_Bacteroidetes; c_Bacteroidia; o_Bacteroidales; f_Prevotellaceae | 0.80 | 0.70 | 0.64 | 0.00 | 0.00 |
| k_Bacteria; p_Bacteroidetes; c_Bacteroidia; o_Bacteroidales; f_Rikenellaceae | 0.60 | 1.10 | 1.45 | 1.34 | 1.35 |
| k_Bacteria; p_Bacteroidetes; c_Bacteroidia; o_Bacteroidales; f_S24-7 | 26.30 | 44.60 | 21.07 | 24.99 | 23.08 |
| k_Bacteria; p_Bacteroidetes; c_Bacteroidia; o_Bacteroidales; f_[Odoribacteraceae] | 0.20 | 0.30 | 0.54 | 5.25 | 5.39 |
| k_Bacteria; p_Bacteroidetes; c_Bacteroidia; o_Bacteroidales; f_[Paraprevotellaceae] | 0.00 | 0.20 | 0.09 | 0.00 | 0.00 |
| k_Bacteria; p_Deferribacteres; c_Deferribacteres; o_Deferribacterales; f_Deferribacteraceae | 0.30 | 0.40 | 0.18 | 0.10 | 0.09 |
| k_Bacteria; p_Firmicutes; c_Bacilli; o_Lactobacillales; f_Lactobacillaceae | 42.80 | 21.60 | 27.33 | 31.66 | 34.30 |
| k_Bacteria; p_Firmicutes; c_Clostridia; o_Clostridiales; Other | 11.60 | 10.90 | 21.79 | 12.11 | 10.70 |
| k_Bacteria; p_Firmicutes; c_Clostridia; o_Clostridiales; f_Clostridiaceae | 6.20 | 9.30 | 9.08 | 5.34 | 6.64 |
| k_Bacteria; p_Firmicutes; c_Clostridia; o_Clostridiales; f_Dehalobacteriaceae | 0.00 | 0.00 | 0.09 | 0.10 | 0.09 |
| k_Bacteria; p_Firmicutes; c_Clostridia; o_Clostridiales; f_Lachnospiraceae | 1.00 | 2.00 | 5.18 | 0.38 | 0.18 |

TABLE 5-continued

Gut Microbiota Composition After ELN Uptake Based on Analysis with 16S rRNA Sequencing

| | | | | | |
|---|---|---|---|---|---|
| k_Bacteria; p_Firmicutes; c_Clostridia; o_Clostridiales; f_Peptostreptococcaceae | 0.00 | 0.00 | 0.00 | 0.48 | 0.54 |
| k_Bacteria; p_Firmicutes; c_Clostridia; o_Clostridiales; f_Ruminococcaceae | 2.90 | 2.10 | 7.81 | 2.86 | 2.51 |
| k_Bacteria; p_Firmicutes; c_Clostridia; o_Clostridiales; f_[Mogibacteriaceae] | 0.00 | 0.00 | 0.00 | 0.00 | 0.00 |
| k_Bacteria; p_Firmicutes; c_Erysipelotrichi; o_Erysipelotrichales; f_Erysipelotrichaceae | 0.00 | 0.00 | 0.00 | 2.67 | 2.96 |
| k_Bacteria; p_Proteobacteria; c_Betaproteobacteria; o_Burkholderiales; f_Alcaligenaceae | 0.20 | 0.40 | 0.45 | 0.00 | 0.00 |
| k_Bacteria; p_Proteobacteria; c_Deltaproteobacteria; o_Desulfovibrionales; f_Desulfovibrionaceae | 0.50 | 0.80 | 0.18 | 1.34 | 1.71 |
| k_Bacteria; p_Proteobacteria; c_Epsilonproteobacteria; o_Campylobacterales; f_Helicobacteraceae | 1.20 | 0.60 | 0.36 | 0.38 | 0.09 |
| k_Bacteria; p_TM7; c_TM7-3; o_CW040; f_F16 | 0.00 | 0.30 | 0.18 | 0.29 | 0.18 |
| k_Bacteria; p_Tenericutes; c_Mollicutes; o_Mycoplasmatales; f_Mycoplasmataceae | 0.30 | 0.10 | 0.00 | 0.00 | 0.00 |

| | Garlic | | Turmeric | | Grapefruit | |
|---|---|---|---|---|---|---|
| Taxonomy | 1* | 2* | 1* | 2* | 1* | 2* |
| Unassigned; Other; Other; Other; Other | 5.82 | 4.85 | 5.04 | 7.25 | 4.21 | 1.88 |
| k_Bacteria, Other | 1.28 | 1.59 | 0.00 | 0.26 | 2.25 | 2.12 |
| k_Bacteria. p_Actinobacteria. c_Actinobacteria. o_Actinomycetales. f_Microbacteriaceae | 0.27 | 0.00 | 1.16 | 0.00 | 0.00 | 0.00 |
| k_Bacteria; p_Bacteroidetes; c_Bacteroidia; o_Bacteroidales; Other | 0.00 | 0.39 | 0.00 | 2.22 | 1.43 | 1.49 |
| k_Bacteria; p_Bacteroidetes; c_Bacteroidia; o_Bacteroidales; f_Bacteroidaceae | 0.89 | 0.90 | 1.97 | 0.00 | 1.88 | 2.68 |
| k_Bacteria; p_Bacteroidetes; c_Bacteroidia; o_Bacteroidales; f_Porphyromonadaceae | 0.66 | 0.71 | 1.68 | 0.00 | 0.39 | 0.49 |
| k_Bacteria; p_Bacteroidetes; c_Bacteroidia; o_Bacteroidales; f_Prevotellaceae | 2.83 | 3.37 | 0.59 | 0.00 | 2.20 | 1.77 |
| k_Bacteria; p_Bacteroidetes; c_Bacteroidia; o_Bacteroidales; f_Rikenellaceae | 2.63 | 3.07 | 1.27 | 0.00 | 4.11 | 3.87 |
| k_Bacteria; p_Bacteroidetes; c_Bacteroidia; o_Bacteroidales; f_S24-7 | 23.38 | 23.44 | 24.51 | 23.01 | 22.56 | 24.53 |
| k_Bacteria; p_Bacteroidetes; c_Bacteroidia; o_Bacteroidales; f_[Odoribacteraceae] | 0.64 | 0.68 | 0.14 | 0.00 | 1.76 | 1.95 |
| k_Bacteria; p_Bacteroidetes; c_Bacteroidia; o_Bacteroidales; f_[Paraprevotellaceae] | 1.74 | 2.04 | 0.40 | 0.00 | 2.62 | 2.51 |
| k_Bacteria; p_Deferribacteres; c_Deferribacteres; o_Deferribacterales; f_Deferribacteraceae | 1.36 | 1.70 | 0.57 | 0.81 | 1.29 | 0.82 |
| k_Bacteria; p_Firmicutes; c_Bacilli; o_Lactobacillales; f_Lactobacillaceae | 0.00 | 0.13 | 14.64 | 17.57 | 0.15 | 0.00 |
| k_Bacteria; p_Firmicutes; c_Clostridia; o_Clostridiales; Other | 17.30 | 17.32 | 5.57 | 0.68 | 15.38 | 18.35 |
| k_Bacteria; p_Firmicutes; c_Clostridia; o_Clostridiales; f_Clostridiaceae | 0.20 | 0.15 | 0.18 | 0.00 | 0.04 | 0.00 |
| k_Bacteria; p_Firmicutes; c_Clostridia; o_Clostridiales; f_Dehalobacteriaceae | 0.72 | 0.69 | 0.00 | 0.00 | 0.69 | 0.09 |
| k_Bacteria; p_Firmicutes; c_Clostridia; o_Clostridiales; f_Lachnospiraceae | 13.39 | 13.89 | 3.61 | 10.02 | 10.50 | 13.55 |
| k_Bacteria; p_Firmicutes; c_Clostridia; o_Clostridiales; f_Ruminococcaceae | 16.29 | 15.69 | 4.07 | 2.70 | 13.18 | 12.31 |
| k_Bacteria; p_Firmicutes; c_Clostridia; o_Clostridiales; f_[Mogibacteriaceae] | 0.48 | 0.45 | 0.00 | 0.00 | 0.31 | 0.65 |
| k_Bacteria; p_Firmicutes; c_Erysipelotrichi; o_Erysipelotrichales; f_Erysipelotrichaceae | 0.15 | 0.00 | 1.76 | 2.30 | 1.08 | 0.28 |
| k_Bacteria. p_Proteobacteria. c_Alphaproteobacteria. o_Rhizobiales. f_Bradyrhizobiaceae | 0.30 | 0.13 | 3.98 | 0.00 | 0.00 | 0.00 |
| k_Bacteria. p_Proteobacteria. c_Alphaproteobacteria. o_Rhizobiales. f_Hyphomicrobiaceae | 0.10 | 0.13 | 3.84 | 6.37 | 0.00 | 0.00 |
| k_Bacteria; p_Proteobacteria; c_Alphaproteobacteria; o_Rhodospirillales. f_Rhodospirillaceae | 0.26 | 0.12 | 0.44 | 0.00 | 0.00 | 0.00 |
| k_Bacteria. p_Proteobacteria. c_Betaproteobacteria. o_Burkholderiales. f_Alcaligenaceae | 1.74 | 1.48 | 1.28 | 0.00 | 1.21 | 0.63 |
| k_Bacteria. p_Proteobacteria. c_Betaproteobacteria. o_Burkholderiales. f_Comamonadaceae | 0.24 | 0.35 | 1.82 | 2.30 | 0.00 | 0.00 |
| k_Bacteria. p_Proteobacteria. c_Betaproteobacteria. o_Burkholderiales. f_Oxalobacteraceae | 0.14 | 0.00 | 1.64 | 4.02 | 0.00 | 0.00 |
| k_Bacteria; p_Proteobacteria; c_Deltaproteobacteria; o_Desulfovibrionales; f_Desulfovibrionaceae | 1.88 | 1.42 | 0.03 | 0.00 | 1.52 | 1.06 |
| k_Bacteria; p_Proteobacteria; c_Epsilonproteobacteria; o_Campylobacterales; f_Helicobacteraceae | 4.43 | 3.85 | 2.77 | 4.79 | 7.64 | 4.81 |
| k_Bacteria. p_Proteobacteria. c_Gammaproteobacteria. o_Enterobacteriales. f_Enterobacteriaceae | 0.00 | 0.00 | 15.25 | 11.37 | 0.00 | 0.00 |
| k_Bacteria. p_Tenericutes. c_Mollicutes. o_Anaeroplasmatales. f_Anaeroplasmataceae | 0.38 | 0.42 | 0.00 | 0.00 | 1.80 | 2.63 |
| k_Bacteria; p_Tenericutes; c_Mollicutes; o_Mycoplasmatales. f_Mycoplasmataceae | 0.00 | 0.19 | 0.00 | 0.00 | 0.78 | 0.96 |
| k_Bacteria. p_Verrucomicrobia. c_Verrucomicrobiae. o_Verrucomicrobiales. f_Verrucomicrobiaceae | 0.39 | 0.00 | 1.25 | 4.06 | 0.45 | 0.00 |

*Fecal DNA was from C57BL/6 mice administrated with PKH26 labelled GELNs by gavage one time for 2 hours and the PKH26+ bacteria were sorted for sequencing Detail processing see Methods
*Each group was pooled from three independent samples

TABLE 6

Concentration of Plant ELNs Lipids Analyzed with Mass Spec (nmol/mg ELNs)

| | | GELNs | | Turmeric | | Garlic | | Grapefruit | |
|---|---|---|---|---|---|---|---|---|---|
| Mass Formula | Name | Average | SD | Average | SD | Average | SD | Average | SD |
| 926.6 C49H80O15 | DGDG(34:6) | 0.00 | 0.00 | 0.00 | 0.00 | 0.00 | 0.00 | 0.00 | 0.00 |
| 928.6 C49H82O15 | DGDG(34:5) | 0.00 | 0.00 | 0.00 | 0.00 | 0.01 | 0.00 | 0.00 | 0.00 |
| 930.6 C49H84O15 | DGDG(34:4) | 0.00 | 0.00 | 0.04 | 0.00 | 0.01 | 0.00 | 0.68 | 0.01 |
| 932.6 C49H86O15 | DGDG(34:3) | 5.58 | 0.24 | 15.05 | 1.02 | 4.34 | 0.39 | 15.00 | 0.28 |
| 934.6 C49H88O15 | DGDG(34:2) | 42.90 | 1.82 | 41.54 | 2.82 | 1.91 | 0.17 | 5.31 | 0.10 |
| 936.6 C49H90O15 | DGDG(34:1) | 97.43 | 4.13 | 55.40 | 3.77 | 2.55 | 0.23 | 5.30 | 0.10 |
| 954.6 C51H84O15 | DGDG(36:6) | 4.87 | 0.21 | 9.57 | 0.65 | 11.41 | 1.02 | 23.10 | 0.43 |
| 956.6 C51H86O15 | DGDG(36:5) | 29.63 | 1.26 | 47.56 | 3.23 | 11.64 | 1.04 | 11.50 | 0.21 |
| 958.6 C51H88O15 | DGDG(36:4) | 138.65 | 5.88 | 86.32 | 5.87 | 4.25 | 0.38 | 30.34 | 0.56 |
| 960.6 C51H90O15 | DGDG(36:3) | 119.80 | 5.08 | 37.74 | 2.57 | 1.34 | 0.12 | 8.02 | 0.15 |
| 962.6 C51H92O15 | DGDG(36:2) | 57.25 | 2.43 | 18.11 | 1.23 | 0.04 | 0.00 | 2.37 | 0.04 |
| 964.7 C51H94O15 | DGDG(36:1) | 22.88 | 0.97 | 10.43 | 0.71 | 0.00 | 0.00 | 2.05 | 0.04 |
| 982.6 C53H88O15 | DGDG(38:6) | 1.17 | 0.05 | 0.38 | 0.03 | 0.46 | 0.04 | 1.40 | 0.03 |
| 984.6 C53H90O15 | DGDG(38:5) | 7.44 | 0.32 | 1.56 | 0.11 | 0.10 | 0.01 | 2.09 | 0.04 |

TABLE 6-continued

Concentration of Plant ELNs Lipids Analyzed with Mass Spec (nmol/mg ELNs)

| | | | GELNs | | Turmeric | | Garlic | | Grapefruit | |
|---|---|---|---|---|---|---|---|---|---|---|
| Mass | Formula | Name | Average | SD | Average | SD | Average | SD | Average | SD |
| 986.6 | C53H92O15 | DGDG(38:4) | 0.00 | 0.00 | 4.90 | 0.33 | 0.06 | 0.01 | 2.32 | 0.04 |
| 988.7 | C53H94O15 | DGDG(38:3) | 0.00 | 0.00 | 7.40 | 0.50 | 0.19 | 0.02 | 0.85 | 0.02 |
| | Total DGDG | | 527.60 | 22.39 | 336.00 | 22.84 | 38.31 | 3.43 | 110.32 | 2.05 |
| 764.5 | C43H70O10 | MGDG(34:6) | 0.00 | 0.00 | 0.00 | 0.00 | 0.00 | 0.00 | 0.51 | 0.01 |
| 766.5 | C43H72O10 | MGDG(34:5) | 0.00 | 0.00 | 0.00 | 0.00 | 0.00 | 0.00 | 1.42 | 0.03 |
| 768.5 | C43H74O10 | MGDG(34:4) | 0.64 | 0.03 | 0.59 | 0.04 | 0.14 | 0.01 | 6.40 | 0.12 |
| 770.5 | C43H76O10 | MGDG(34:3) | 0.00 | 0.00 | 7.87 | 0.53 | 1.01 | 0.09 | 7.90 | 0.15 |
| 772.6 | C43H78O10 | MGDG(34:2) | 9.17 | 0.39 | 5.87 | 0.40 | 0.05 | 0.00 | 3.58 | 0.07 |
| 774.6 | C43H80O10 | MGDG(34:1) | 19.13 | 0.81 | 7.49 | 0.51 | 0.69 | 0.06 | 14.80 | 0.28 |
| 792.5 | C45H74O10 | MGDG(36:6) | 91.86 | 3.90 | 53.35 | 3.63 | 20.22 | 1.81 | 216.96 | 4.04 |
| 794.5 | C45H76O10 | MGDG(36:5) | 170.49 | 7.24 | 113.51 | 7.72 | 25.96 | 2.32 | 98.29 | 1.83 |
| 796.6 | C45H78O10 | MGDG(36:4) | 286.61 | 12.16 | 75.12 | 5.11 | 11.79 | 1.06 | 109.36 | 2.03 |
| 798.6 | C45H80O10 | MGDG(36:3) | 153.29 | 6.51 | 22.19 | 1.51 | 0.87 | 0.08 | 23.14 | 0.43 |
| 800.6 | C45H82O10 | MGDG(36:2) | 33.08 | 1.40 | 1.89 | 0.13 | 0.87 | 0.08 | 17.54 | 0.33 |
| 802.6 | C45H84O10 | MGDG(36:1) | 0.22 | 0.01 | 0.73 | 0.05 | 0.00 | 0.00 | 23.89 | 0.44 |
| 820.6 | C47H78O10 | MGDG(38:6) | 0.00 | 0.00 | 0.00 | 0.00 | 0.08 | 0.01 | 0.00 | 0.00 |
| 822.6 | C47H80O10 | MGDG(38:5) | 2.93 | 0.12 | 0.44 | 0.03 | 0.13 | 0.01 | 1.83 | 0.03 |
| 824.6 | C47H82O10 | MGDG(38:4) | 1.44 | 0.06 | 0.23 | 0.02 | 0.13 | 0.01 | 0.00 | 0.00 |
| | Total MGDG | | 782.83 | 33.22 | 291.02 | 19.79 | 61.93 | 5.55 | 532.59 | 9.91 |
| 738.5 | C38H73O10P | PG(32:1) | 0.20 | 0.01 | 0.06 | 0.00 | 0.10 | 0.01 | 5.28 | 0.10 |
| 740.5 | C38H75O10P | PG(32:0) | 2.23 | 0.09 | 19.03 | 1.29 | 4.20 | 0.38 | 55.53 | 1.03 |
| 760.5 | C40H71O10P | PG(34:4) | 0.13 | 0.01 | 0.43 | 0.03 | 0.00 | 0.00 | 0.65 | 0.01 |
| 762.5 | C40H73O10P | PG(34:3) | 0.65 | 0.03 | 1.31 | 0.09 | 9.34 | 0.84 | 27.49 | 0.51 |
| 764.5 | C40H75O10P | PG(34:2) | 3.11 | 0.13 | 5.77 | 0.39 | 58.46 | 5.24 | 60.56 | 1.13 |
| 766.5 | C40H77O10P | PG(34:1) | 3.30 | 0.14 | 4.05 | 0.28 | 1.05 | 0.09 | 39.51 | 0.74 |
| 768.5 | C40H79O10P | PG(34:0) | 3.71 | 0.16 | 5.25 | 0.36 | 1.77 | 0.16 | 6.57 | 0.12 |
| 784.5 | C42H71O10P | PG(36:6) | 0.21 | 0.01 | 0.12 | 0.01 | 0.11 | 0.01 | 1.26 | 0.02 |
| 786.5 | C42H73O10P | PG(36:5) | 0.16 | 0.01 | 0.54 | 0.04 | 1.04 | 0.09 | 6.02 | 0.11 |
| 788.5 | C42H75O10P | PG(36:4) | 1.82 | 0.08 | 0.77 | 0.05 | 3.06 | 0.27 | 4.68 | 0.09 |
| 790.5 | C42H77O10P | PG(36:3) | 0.37 | 0.02 | 0.19 | 0.01 | 0.32 | 0.03 | 9.01 | 0.17 |
| 792.5 | C42H79O10P | PG(36:2) | 1.26 | 0.05 | 0.35 | 0.02 | 0.82 | 0.07 | 5.00 | 0.09 |
| 794.6 | C42H81O10P | PG(36:1) | 0.70 | 0.03 | 0.54 | 0.04 | 0.15 | 0.01 | 2.03 | 0.04 |
| | Total PG | | 17.87 | 0.76 | 38.42 | 2.61 | 80.42 | 7.20 | 223.59 | 4.16 |
| 500.3 | C22H43O9P | LPG(16:1) | 15.72 | 0.67 | 18.86 | 1.28 | 2.12 | 0.19 | 2.03 | 0.04 |
| 502.3 | C22H45O9P | LPG(16:0) | 14.98 | 0.64 | 38.89 | 2.64 | 21.10 | 1.89 | 0.00 | 0.00 |
| 524.3 | C24H43O9P | LPG(18:3) | 11.47 | 0.49 | 7.93 | 0.54 | 2.28 | 0.20 | 1.77 | 0.03 |
| 526.3 | C24H45O9P | LPG(18:2) | 26.75 | 1.14 | 24.58 | 1.67 | 7.12 | 0.64 | 2.03 | 0.04 |
| 528.3 | C24H47O9P | LPG(18:1) | 20.15 | 0.86 | 20.39 | 1.39 | 4.17 | 0.37 | 0.00 | 0.00 |
| | Total LysoPG | | 89.06 | 3.78 | 110.64 | 7.52 | 36.79 | 3.30 | 5.82 | 0.11 |
| 494.3 | C24H48O7PN | LPC(16:1) | 0.10 | 0.00 | 0.04 | 0.00 | 0.14 | 0.01 | 0.75 | 0.01 |
| 496.3 | C24H50O7PN | LPC(16:0) | 1.82 | 0.08 | 0.30 | 0.02 | 2.77 | 0.25 | 8.59 | 0.16 |
| 518.3 | C26H48O7PN | LPC(18:3) | 0.51 | 0.02 | 0.13 | 0.01 | 0.61 | 0.05 | 2.79 | 0.05 |
| 520.3 | C26H50O7PN | LPC(18:2) | 8.32 | 0.35 | 0.15 | 0.01 | 8.22 | 0.74 | 8.12 | 0.15 |
| 522.3 | C26H52O7PN | LPC(18:1) | 5.67 | 0.24 | 0.11 | 0.01 | 1.18 | 0.11 | 4.57 | 0.09 |
| 524.4 | C26H54O7PN | LPC(18:0) | 0.21 | 0.01 | 0.15 | 0.01 | 0.17 | 0.02 | 1.30 | 0.02 |
| | Total LysoPC | | 16.64 | 0.71 | 0.88 | 0.06 | 13.10 | 1.17 | 26.12 | 0.49 |
| 452.3 | C21H42O7PN | LPE(16:1) | 0.37 | 0.02 | 0.10 | 0.01 | 0.00 | 0.00 | 2.01 | 0.04 |
| 454.3 | C21H44O7PN | LPE(16:0) | 0.43 | 0.02 | 0.34 | 0.02 | 3.73 | 0.33 | 9.78 | 0.18 |
| 476.3 | C23H42O7PN | LPE(18:3) | 0.00 | 0.00 | 0.04 | 0.00 | 0.04 | 0.00 | 5.37 | 0.10 |
| 478.3 | C23H44O7PN | LPE(18:2) | 1.27 | 0.05 | 0.47 | 0.03 | 5.38 | 0.48 | 18.93 | 0.35 |
| 480.3 | C23H46O7PN | LPE(18:1) | 0.05 | 0.00 | 0.05 | 0.00 | 0.19 | 0.02 | 4.11 | 0.08 |
| | Total LysoPE | | 2.12 | 0.09 | 1.00 | 0.07 | 9.34 | 0.84 | 40.20 | 0.75 |
| 734.6 | C40H80O8PN | PC(32:0) | 0.06 | 0.00 | 0.44 | 0.03 | 0.68 | 0.06 | 3.24 | 0.06 |
| 754.5 | C42H76O8PN | PC(34:4) | 0.14 | 0.01 | 0.21 | 0.01 | 0.00 | 0.00 | 18.68 | 0.35 |
| 756.5 | C42H78O8PN | PC(34:3) | 0.93 | 0.04 | 1.91 | 0.13 | 29.07 | 2.60 | 296.75 | 5.52 |
| 758.6 | C42H80O8PN | PC(34:2) | 7.79 | 0.33 | 8.68 | 0.59 | 229.05 | 20.52 | 487.74 | 9.07 |
| 760.6 | C42H82O8PN | PC(34:1) | 2.32 | 0.10 | 1.99 | 0.13 | 22.60 | 2.02 | 163.34 | 3.04 |
| 778.5 | C44H76O8PN | PC(36:6) | 0.10 | 0.00 | 0.13 | 0.01 | 3.30 | 0.30 | 47.61 | 0.89 |
| 780.5 | C44H78O8PN | PC(36:5) | 0.78 | 0.03 | 0.75 | 0.05 | 33.90 | 3.04 | 188.86 | 3.51 |
| 782.6 | C44H80O8PN | PC(36:4) | 4.77 | 0.20 | 2.95 | 0.20 | 208.83 | 18.70 | 320.75 | 5.97 |
| 784.6 | C44H82O8PN | PC(36:3) | 2.48 | 0.11 | 1.45 | 0.10 | 36.95 | 3.31 | 242.30 | 4.51 |
| 786.6 | C44H84O8PN | PC(36:2) | 1.08 | 0.05 | 1.12 | 0.08 | 8.23 | 0.74 | 117.56 | 2.19 |
| 788.6 | C44H86O8PN | PC(36:1) | 0.23 | 0.01 | 0.20 | 0.01 | 2.54 | 0.23 | 17.18 | 0.32 |
| 806.6 | C46H80O8PN | PC(38:6) | 0.00 | 0.00 | 0.00 | 0.00 | 0.14 | 0.01 | 1.10 | 0.02 |
| 808.6 | C46H82O8PN | PC(38:5) | 0.00 | 0.00 | 0.00 | 0.00 | 0.48 | 0.04 | 3.18 | 0.06 |
| 810.6 | C46H84O8PN | PC(38:4) | 0.07 | 0.00 | 0.03 | 0.00 | 2.17 | 0.19 | 9.62 | 0.18 |
| 812.6 | C46H86O8PN | PC(38:3) | 0.18 | 0.01 | 0.19 | 0.01 | 2.84 | 0.25 | 13.75 | 0.26 |
| 814.6 | C46H88O8PN | PC(38:2) | 0.07 | 0.00 | 0.38 | 0.03 | 2.32 | 0.21 | 9.24 | 0.17 |

TABLE 6-continued

Concentration of Plant ELNs Lipids Analyzed with Mass Spec (nmol/mg ELNs)

| Mass | Formula | Name | GELNs Average | SD | Turmeric Average | SD | Garlic Average | SD | Grapefruit Average | SD |
|---|---|---|---|---|---|---|---|---|---|---|
| 836.6 | C48H86O8PN | PC(40:5) | 0.00 | 0.00 | 0.00 | 0.00 | 0.01 | 0.00 | 0.10 | 0.00 |
| 838.6 | C48H88O8PN | PC(40:4) | 0.00 | 0.00 | 0.00 | 0.00 | 0.29 | 0.03 | 0.79 | 0.01 |
| 840.6 | C48H90O8PN | PC(40:3) | 0.00 | 0.00 | 0.00 | 0.00 | 2.43 | 0.22 | 1.88 | 0.04 |
| 842.7 | C48H92O8PN | PC(40:2) | 0.06 | 0.00 | 0.09 | 0.01 | 0.94 | 0.08 | 1.72 | 0.03 |
| | | Total PC | 21.07 | 0.89 | 20.51 | 1.39 | 586.78 | 52.55 | 1945.41 | 36.19 |
| 686.5 | C37H68O8PN | PE(32:3) | 0.00 | 0.00 | 0.00 | 0.00 | 0.02 | 0.00 | 0.60 | 0.01 |
| 688.5 | C37H70O8PN | PE(32:2) | 0.00 | 0.00 | 0.00 | 0.00 | 0.16 | 0.01 | 2.98 | 0.06 |
| 690.5 | C37H72O8PN | PE(32:1) | 0.00 | 0.00 | 0.00 | 0.00 | 0.14 | 0.01 | 11.57 | 0.22 |
| 692.5 | C37H74O8PN | PE(32:0) | 0.00 | 0.00 | 0.05 | 0.00 | 0.05 | 0.00 | 0.00 | 0.00 |
| 712.5 | C39H70O8PN | PE(34:4) | 0.00 | 0.00 | 0.00 | 0.00 | 0.03 | 0.00 | 4.37 | 0.08 |
| 714.5 | C39H72O8PN | PE(34:3) | 0.01 | 0.00 | 0.48 | 0.03 | 7.32 | 0.66 | 274.25 | 5.10 |
| 716.5 | C39H74O8PN | PE(34:2) | 1.92 | 0.08 | 2.23 | 0.15 | 99.80 | 8.94 | 644.28 | 11.99 |
| 718.5 | C39H76O8PN | PE(34:1) | 0.20 | 0.01 | 0.06 | 0.00 | 3.20 | 0.29 | 98.41 | 1.83 |
| 736.5 | C41H70O8PN | PE(36:6) | 0.01 | 0.00 | 0.00 | 0.00 | 0.18 | 0.02 | 19.59 | 0.36 |
| 738.5 | C41H72O8PN | PE(36:5) | 0.19 | 0.01 | 0.18 | 0.01 | 6.76 | 0.61 | 125.96 | 2.34 |
| 740.5 | C41H74O8PN | PE(36:4) | 1.44 | 0.06 | 0.65 | 0.04 | 48.70 | 4.36 | 280.28 | 5.21 |
| 742.5 | C41H76O8PN | PE(36:3) | 0.22 | 0.01 | 0.13 | 0.01 | 6.03 | 0.54 | 174.00 | 3.24 |
| 744.5 | C41H78O8PN | PE(36:2) | 0.00 | 0.00 | 0.38 | 0.03 | 1.42 | 0.13 | 72.67 | 1.35 |
| 746.6 | C41H80O8PN | PE(36:1) | 0.07 | 0.00 | 0.01 | 0.00 | 0.42 | 0.04 | 5.75 | 0.11 |
| 764.5 | C43H74O8PN | PE(38:6) | 0.00 | 0.00 | 0.00 | 0.00 | 0.04 | 0.00 | 1.58 | 0.03 |
| 766.5 | C43H76O8PN | PE(38:5) | 0.00 | 0.00 | 0.00 | 0.00 | 0.09 | 0.01 | 1.53 | 0.03 |
| 768.5 | C43H78O8PN | PE(38:4) | 0.00 | 0.00 | 0.04 | 0.00 | 0.42 | 0.04 | 4.64 | 0.09 |
| 770.6 | C43H80O8PN | PE(38:3) | 0.05 | 0.00 | 0.02 | 0.00 | 0.39 | 0.03 | 9.00 | 0.17 |
| 798.6 | C45H84O8PN | PE(40:3) | 0.02 | 0.00 | 0.00 | 0.00 | 0.15 | 0.01 | 9.36 | 0.17 |
| 800.6 | C45H86O8PN | PE(40:2) | 0.05 | 0.00 | 0.08 | 0.01 | 2.17 | 0.19 | 12.44 | 0.23 |
| 824.6 | C47H86O8PN | PE(42:4) | 0.01 | 0.00 | 0.00 | 0.00 | 0.00 | 0.00 | 3.00 | 0.06 |
| 826.6 | C47H88O8PN | PE(42:3) | 0.07 | 0.00 | 0.06 | 0.00 | 0.19 | 0.02 | 13.77 | 0.26 |
| 828.6 | C47H90O8PN | PE(42:2) | 0.21 | 0.01 | 0.58 | 0.04 | 1.63 | 0.15 | 31.96 | 0.59 |
| | | Total PE | 4.49 | 0.19 | 4.96 | 0.34 | 179.29 | 16.06 | 1801.99 | 33.53 |
| 822.5 | C41H73O13P | PI(32:3) | 1.91 | 0.08 | 0.10 | 0.01 | 0.15 | 0.01 | 0.16 | 0.00 |
| 824.5 | C41H75O13P | PI(32:2) | 2.65 | 0.11 | 0.66 | 0.04 | 0.06 | 0.01 | 0.12 | 0.00 |
| 826.5 | C41H77O13P | PI(32:1) | 0.43 | 0.02 | 0.53 | 0.04 | 0.08 | 0.01 | 0.47 | 0.01 |
| 828.5 | C41H79O13P | PI(32:0) | 1.99 | 0.08 | 8.10 | 0.55 | 0.31 | 0.03 | 6.60 | 0.12 |
| 848.5 | C43H75O13P | PI(34:4) | 0.37 | 0.02 | 0.12 | 0.01 | 0.10 | 0.01 | 0.53 | 0.01 |
| 850.5 | C43H77O13P | PI(34:3) | 3.44 | 0.15 | 22.58 | 1.54 | 3.88 | 0.35 | 27.69 | 0.52 |
| 852.5 | C43H79O13P | PI(34:2) | 16.28 | 0.69 | 95.17 | 6.47 | 21.79 | 1.95 | 53.61 | 1.00 |
| 854.5 | C43H81O13P | PI(34:1) | 4.37 | 0.19 | 12.67 | 0.86 | 1.05 | 0.09 | 32.56 | 0.61 |
| 872.5 | C45H75O13P | PI(36:6) | 0.46 | 0.02 | 0.57 | 0.04 | 0.59 | 0.05 | 7.77 | 0.14 |
| 874.5 | C45H77O13P | PI(36:5) | 2.50 | 0.11 | 3.96 | 0.27 | 3.27 | 0.29 | 34.10 | 0.63 |
| 876.5 | C45H79O13P | PI(36:4) | 7.98 | 0.34 | 9.41 | 0.64 | 9.02 | 0.81 | 80.21 | 1.49 |
| 878.5 | C45H81O13P | PI(36:3) | 4.08 | 0.17 | 3.14 | 0.21 | 1.82 | 0.16 | 56.31 | 1.05 |
| 880.6 | C45H83O13P | PI(36:2) | 0.52 | 0.02 | 2.42 | 0.16 | 0.50 | 0.04 | 24.38 | 0.45 |
| 882.6 | C45H85O13P | PI(36:1) | 0.17 | 0.01 | 0.49 | 0.03 | 0.01 | 0.00 | 1.16 | 0.02 |
| | | Total PI | 47.15 | 2.00 | 159.94 | 10.87 | 42.62 | 3.82 | 325.67 | 6.06 |
| 756.5 | C40H70O10PN | PS(34:4) | 0.01 | 0.00 | 0.05 | 0.00 | 0.00 | 0.00 | 0.03 | 0.00 |
| 758.5 | C40H72O10PN | PS(34:3) | 0.27 | 0.01 | 0.01 | 0.00 | 0.13 | 0.01 | 4.89 | 0.09 |
| 760.5 | C40H74O10PN | PS(34:2) | 2.75 | 0.12 | 0.15 | 0.01 | 1.09 | 0.10 | 9.72 | 0.18 |
| 762.5 | C40H76O10PN | PS(34:1) | 0.41 | 0.02 | 0.00 | 0.00 | 0.00 | 0.00 | 2.32 | 0.04 |
| 780.5 | C42H70O10PN | PS(36:6) | 0.00 | 0.00 | 0.01 | 0.00 | 0.02 | 0.00 | 0.24 | 0.00 |
| 782.5 | C42H72O10PN | PS(36:5) | 0.10 | 0.00 | 0.04 | 0.00 | 0.13 | 0.01 | 0.53 | 0.01 |
| 784.5 | C42H74O10PN | PS(36:4) | 0.49 | 0.02 | 0.08 | 0.01 | 0.26 | 0.02 | 1.53 | 0.03 |
| 786.5 | C42H76O10PN | PS(36:3) | 0.54 | 0.02 | 0.04 | 0.00 | 0.02 | 0.00 | 3.22 | 0.06 |
| 788.5 | C42H78O10PN | PS(36:2) | 0.17 | 0.01 | 0.03 | 0.00 | 0.05 | 0.00 | 3.13 | 0.06 |
| 790.6 | C42H80O10PN | PS(36:1) | 0.01 | 0.00 | 0.00 | 0.00 | 0.00 | 0.00 | 0.56 | 0.01 |
| 808.5 | C44H74O10PN | PS(38:6) | 0.00 | 0.00 | 0.00 | 0.00 | 0.00 | 0.00 | 0.00 | 0.00 |
| 810.5 | C44H76O10PN | PS(38:5) | 0.00 | 0.00 | 0.00 | 0.00 | 0.00 | 0.00 | 0.05 | 0.00 |
| 812.5 | C44H78O10PN | PS(38:4) | 0.01 | 0.00 | 0.00 | 0.00 | 0.01 | 0.00 | 0.52 | 0.01 |
| 814.6 | C44H80O10PN | PS(38:3) | 0.08 | 0.00 | 0.00 | 0.00 | 0.02 | 0.00 | 3.48 | 0.06 |
| 816.6 | C44H82O10PN | PS(38:2) | 0.15 | 0.01 | 0.01 | 0.00 | 0.09 | 0.01 | 6.84 | 0.13 |
| 818.6 | C44H84O10PN | PS(38:1) | 0.02 | 0.00 | 0.00 | 0.00 | 0.01 | 0.00 | 2.30 | 0.04 |
| 840.6 | C46H82O10PN | PS(40:4) | 0.00 | 0.00 | 0.02 | 0.00 | 0.00 | 0.00 | 1.84 | 0.03 |
| 842.6 | C46H84O10PN | PS(40:3) | 0.16 | 0.01 | 0.01 | 0.00 | 0.17 | 0.01 | 9.04 | 0.17 |
| 844.6 | C46H86O10PN | PS(40:2) | 1.61 | 0.07 | 0.03 | 0.00 | 2.10 | 0.19 | 17.76 | 0.33 |
| 846.6 | C46H88O10PN | PS(40:1) | 0.25 | 0.01 | 0.00 | 0.00 | 0.09 | 0.01 | 4.46 | 0.08 |
| 868.6 | C48H86O10PN | PS(42:4) | 0.00 | 0.00 | 0.00 | 0.00 | 0.01 | 0.00 | 2.62 | 0.05 |
| 870.6 | C48H88O10PN | PS(42:3) | 0.64 | 0.03 | 0.07 | 0.00 | 0.14 | 0.01 | 20.87 | 0.39 |
| 872.6 | C48H90O10PN | PS(42:2) | 8.61 | 0.37 | 0.26 | 0.02 | 2.06 | 0.18 | 40.12 | 0.75 |

TABLE 6-continued

Concentration of Plant ELNs Lipids Analyzed with Mass Spec (nmol/mg ELNs)

| Mass | Formula | Name | GELNs Average | SD | Turmeric Average | SD | Garlic Average | SD | Grapefruit Average | SD |
|---|---|---|---|---|---|---|---|---|---|---|
| 874.6 | C48H92O10PN | PS(42:1) | 0.93 | 0.04 | 0.02 | 0.00 | 0.03 | 0.00 | 8.17 | 0.15 |
| 898.6 | C50H92O10PN | PS(44:3) | 0.15 | 0.01 | 0.01 | 0.00 | 0.02 | 0.00 | 9.36 | 0.17 |
| 900.7 | C50H94O10PN | PS(44:2) | 1.35 | 0.06 | 0.04 | 0.00 | 0.00 | 0.00 | 22.89 | 0.43 |
| | | Total PS | 18.72 | 0.79 | 0.88 | 0.06 | 6.44 | 0.58 | 176.52 | 3.28 |
| 666.5 | C35H69O8P | PA(32:0) | 2.43 | 0.10 | 11.39 | 0.77 | 0.17 | 0.02 | 0.37 | 0.01 |
| 682.4 | C37H61O8P | PA(34:6) | 0.00 | 0.00 | 0.00 | 0.00 | 0.00 | 0.00 | 0.02 | 0.00 |
| 684.4 | C37H63O8P | PA(34:5) | 0.00 | 0.00 | 0.05 | 0.00 | 0.00 | 0.00 | 0.09 | 0.00 |
| 686.4 | C37H65O8P | PA(34:4) | 0.39 | 0.02 | 0.56 | 0.04 | 0.01 | 0.00 | 1.03 | 0.02 |
| 688.5 | C37H67O8P | PA(34:3) | 20.51 | 0.87 | 30.30 | 2.06 | 2.71 | 0.24 | 31.43 | 0.58 |
| 690.5 | C37H69O8P | PA(34:2) | 325.56 | 13.82 | 231.68 | 15.75 | 24.59 | 2.20 | 48.48 | 0.90 |
| 692.5 | C37H71O8P | PA(34:1) | 70.04 | 2.97 | 35.54 | 2.42 | 1.76 | 0.16 | 10.56 | 0.20 |
| 710.4 | C39H65O8P | PA(36:6) | 0.69 | 0.03 | 1.37 | 0.09 | 0.15 | 0.01 | 3.34 | 0.06 |
| 712.5 | C39H67O8P | PA(36:5) | 19.07 | 0.81 | 24.60 | 1.67 | 3.24 | 0.29 | 20.28 | 0.38 |
| 714.5 | C39H69O8P | PA(36:4) | 219.54 | 9.32 | 114.03 | 7.75 | 24.66 | 2.21 | 36.88 | 0.69 |
| 716.5 | C39H71O8P | PA(36:3) | 130.51 | 5.54 | 38.69 | 2.63 | 3.41 | 0.31 | 25.41 | 0.47 |
| 718.5 | C39H73O8P | PA(36:2) | 39.98 | 1.70 | 18.31 | 1.25 | 0.77 | 0.07 | 8.74 | 0.16 |
| | | Total PA | 828.73 | 35.17 | 506.54 | 34.44 | 61.49 | 5.51 | 186.62 | 3.47 |

TABLE 7

Top 50 mRNAs and Proteins Differentially Expressed in LGG Treated with GELNs Analyzed with mRNA Sequencing (read #/average read #) and LC/MS (iBAQ (area)), Respectively mRNA

| Induction Gene ID | In vivo PBS | GELN | In vitro PBS | GELN | Reduction Gene ID | In vivo PBS | GELN | In vitro PBS | GELN |
|---|---|---|---|---|---|---|---|---|---|
| LGG_02504 | 0.119 | 131.045 | 0.241 | 13.248 | is39 | 0.001 | 0.000 | 0.002 | 0.002 |
| LGG_00305 | 0.120 | 131.043 | 0.241 | 13.248 | is41 | 0.001 | 0.000 | 0.002 | 0.002 |
| LGG_02428 | 0.005 | 0.025 | 0.003 | 0.009 | LGG_01889 | 161.886 | 0.447 | 194.451 | 16.184 |
| LGG_00484 | 0.006 | 0.029 | 0.004 | 0.010 | LGG_00375 | 0.035 | 0.002 | 0.043 | 0.045 |
| LGG_02077 | 0.001 | 0.007 | 0.001 | 0.002 | LGG_02513 | 0.726 | 0.051 | 0.920 | 0.700 |
| ssb1 | 0.032 | 0.127 | 0.019 | 0.051 | nrdH | 3.492 | 0.417 | 4.602 | 4.009 |
| rhaD | 0.025 | 0.099 | 0.017 | 0.040 | LGG_00702 | 0.490 | 0.076 | 0.664 | 0.897 |
| copY | 0.015 | 0.059 | 0.059 | 0.024 | LGG_01250 | 2.686 | 0.425 | 3.644 | 2.259 |
| sfcA | 0.077 | 0.299 | 0.036 | 0.122 | LGG_00519 | 0.108 | 0.018 | 0.147 | 0.094 |
| frvA | 0.003 | 0.010 | 0.003 | 0.004 | LGG_02416 | 0.035 | 0.007 | 0.048 | 0.021 |
| ulaE | 0.018 | 0.070 | 0.009 | 0.029 | LGG_01041 | 0.004 | 0.001 | 0.006 | 0.010 |
| LGG_00704 | 0.012 | 0.046 | 0.008 | 0.019 | nrdF | 2.115 | 0.422 | 2.957 | 2.251 |
| is35 | 0.005 | 0.018 | 0.004 | 0.008 | mraZ | 2.151 | 0.446 | 3.023 | 1.966 |
| is42 | 0.005 | 0.018 | 0.004 | 0.008 | LGG_01094 | 0.210 | 0.045 | 0.296 | 0.287 |
| LGG_01819 | 0.011 | 0.040 | 0.008 | 0.018 | mraW | 3.867 | 0.843 | 5.478 | 4.014 |
| hisH | 0.013 | 0.044 | 0.006 | 0.020 | ftsL | 0.404 | 0.091 | 0.574 | 0.423 |
| LGG_02090 | 0.039 | 0.134 | 0.064 | 0.061 | oppA | 8.689 | 1.984 | 12.397 | 12.643 |
| mppX | 0.028 | 0.096 | 0.022 | 0.043 | LGG_02011 | 3.244 | 0.778 | 4.665 | 2.736 |
| LGG_00877 | 0.030 | 0.100 | 0.027 | 0.046 | LGG_01770 | 0.100 | 0.024 | 0.144 | 0.127 |
| thiM | 0.029 | 0.095 | 0.015 | 0.044 | LGG_01870 | 2.402 | 0.587 | 3.466 | 2.629 |
| LGG_02407 | 0.026 | 0.086 | 0.015 | 0.040 | ytgB | 6.797 | 1.679 | 9.825 | 12.594 |
| LGG_00556 | 0.004 | 0.014 | 0.009 | 0.007 | ligA | 2.916 | 0.731 | 4.225 | 2.399 |
| sgaB | 0.005 | 0.017 | 0.004 | 0.008 | LGG_01404 | 0.081 | 0.021 | 0.117 | 0.089 |
| LGG_00531 | 0.004 | 0.014 | 0.001 | 0.007 | LGG_00440 | 0.315 | 0.080 | 0.458 | 1.370 |
| LGG_00835 | 3.963 | 12.432 | 4.153 | 5.992 | nrdE | 11.090 | 2.832 | 16.122 | 16.243 |
| LGG_00816 | 4.028 | 12.432 | 4.153 | 6.070 | LGG_00631 | 0.163 | 0.042 | 0.237 | 0.205 |
| rpe | 0.035 | 0.106 | 0.012 | 0.052 | ycnE | 0.262 | 0.068 | 0.382 | 0.065 |
| srtC2 | 0.048 | 0.148 | 0.032 | 0.073 | LGG_01221 | 1.798 | 0.469 | 2.623 | 1.188 |
| LGG_00552 | 0.054 | 0.163 | 0.027 | 0.081 | vanZ | 0.859 | 0.224 | 1.253 | 0.669 |
| LGG_00304 | 4.257 | 12.819 | 3.388 | 6.383 | LGG_02597 | 0.969 | 0.254 | 1.416 | 0.935 |
| LGG_02505 | 4.258 | 12.819 | 3.388 | 6.385 | ltaS | 1.838 | 0.482 | 2.684 | 1.094 |
| LGG_01890 | 4.259 | 12.819 | 3.388 | 6.385 | LGG_02389 | 0.012 | 0.003 | 0.017 | 0.010 |
| LGG_02808 | 0.025 | 0.074 | 0.011 | 0.037 | LGG_01313 | 0.329 | 0.087 | 0.481 | 0.400 |
| comFA | 0.044 | 0.132 | 0.035 | 0.066 | LGG_01355 | 3.535 | 0.942 | 5.179 | 4.203 |
| LGG_02344 | 0.013 | 0.038 | 0.010 | 0.019 | LGG_01207 | 1.608 | 0.431 | 2.358 | 1.113 |
| mleP | 0.040 | 0.118 | 0.012 | 0.059 | hup | 4.793 | 1.286 | 7.030 | 2.796 |
| ulaA | 0.027 | 0.081 | 0.018 | 0.041 | LGG_02331 | 2.636 | 0.710 | 3.869 | 3.522 |
| LGG_00658 | 0.004 | 0.013 | 0.002 | 0.007 | LGG_01946 | 0.081 | 0.022 | 0.118 | 0.094 |
| LGG_00815 | 3.614 | 10.707 | 2.899 | 5.402 | LGG_02904 | 1.015 | 0.276 | 1.493 | 1.644 |
| LGG_00834 | 3.614 | 10.705 | 2.899 | 5.402 | LGG_02805 | 0.498 | 0.138 | 0.735 | 0.811 |
| LGG_00551 | 0.037 | 0.109 | 0.032 | 0.055 | pbpX | 1.431 | 0.397 | 2.113 | 1.647 |

TABLE 7-continued

Top 50 mRNAs and Proteins Differentially Expressed in LGG
Treated with GELNs Analyzed with mRNA Sequencing (read #/average
read #) and LC/MS (iBAQ (area)), Respectively mRNA

| Induction | In vivo | | In vitro | | Reduction | In vivo | | In vitro | |
|---|---|---|---|---|---|---|---|---|---|
| Gene ID | PBS | GELN | PBS | GELN | Gene ID | PBS | GELN | PBS | GELN |
| LGG_01529 | 0.005 | 0.014 | 0.002 | 0.007 | usp | 2.127 | 0.605 | 3.154 | 2.661 |
| LGG_00104 | 0.100 | 0.291 | 0.053 | 0.149 | spaC | 3.955 | 1.128 | 5.867 | 1.263 |
| LGG_02875 | 0.016 | 0.045 | 0.015 | 0.023 | cggR | 5.293 | 1.512 | 7.855 | 3.495 |
| LGG_02106 | 0.042 | 0.120 | 0.034 | 0.062 | LGG_02127 | 0.142 | 0.041 | 0.211 | 0.143 |
| LGG_00091 | 0.043 | 0.123 | 0.021 | 0.063 | LGG_01518 | 0.429 | 0.123 | 0.637 | 0.392 |
| LGG_02735 | 0.033 | 0.092 | 0.030 | 0.048 | LGG_02845 | 0.103 | 0.030 | 0.153 | 0.203 |
| proV | 0.042 | 0.118 | 0.031 | 0.062 | pbp2A | 4.214 | 1.225 | 6.275 | 3.370 |
| gbuC | 0.026 | 0.074 | 0.014 | 0.039 | lexA | 5.165 | 1.509 | 7.699 | 4.857 |
| LGG_01765 | 0.017 | 0.047 | 0.009 | 0.025 | LGG_00688 | 1.138 | 0.333 | 1.697 | 1.084 |

TABLE 8

Gut Microbiota Composition Treated with PBS, GELNs, GNV/GELN-RNAs and Analyzed by 16S rRNA Sequencing

| | Bacteria Percentage (%) | | |
|---|---|---|---|
| Taxonomy | PBS | GELNs | GNV/GELN-RNAs |
| Unassigned; Other; Other; Other; Other | 3.23 | 3.90 | 5.50 |
| k_Bacteria; p_Bacteroidetes; c_Bacteroidia; o_Bacteroidales; Other | 0.10 | 0.55 | 0.20 |
| k_Bacteria; p_Bacteroidetes; c_Bacteroidia; o_Bacteroidales; f_Bacteroidaceae | 0.49 | 1.20 | 8.02 |
| k_Bacteria; p_Bacteroidetes; c_Bacteroidia; o_Bacteroidales; f_Porphyromonadaceae | 0.14 | 0.80 | 0.50 |
| k_Bacteria; p_Bacteroidetes; c_Bacteroidia; o_Bacteroidales; f_Prevotellaceae | 2.16 | 4.70 | 7.80 |
| k_Bacteria; p_Bacteroidetes; c_Bacteroidia; o_Bacteroidales; f_Rikenellaceae | 3.03 | 1.40 | 1.50 |
| k_Bacteria; p_Bacteroidetes; c_Bacteroidia; o_Bacteroidales; f_S24-7 | 22.07 | 44.25 | 30.40 |
| k_Bacteria; p_Bacteroidetes; c_Bacteroidia; o_Bacteroidales; f_[Odoribacteraceae] | 0.90 | 0.30 | 0.40 |
| k_Bacteria; p_Bacteroidetes; c_Bacteroidia; o_Bacteroidales; f_[Paraprevotellaceae] | 0.17 | 0.65 | 0.80 |
| k_Bacteria; p_Deferribacteres; c_Deferribacteres; o_Deferribacterales; f_Deferribacteraceae | 1.19 | 0.50 | 0.50 |
| k_Bacteria; p_Firmicutes; c_Bacilli; o_Lactobacillales; f_Lactobacillaceae | 0.30 | 30.00 | 24.20 |
| k_Bacteria; p_Firmicutes; c_Clostridia; o_Clostridiales; Other | 34.70 | 2.10 | 8.70 |
| k_Bacteria; p_Firmicutes; c_Clostridia; o_Clostridiales; f_Clostridiaceae | 17.72 | 1.60 | 0.10 |
| k_Bacteria; p_Firmicutes; c_Clostridia; o_Clostridiales; f_Dehalobacteriaceae | 0.10 | 0.05 | 0.00 |
| k_Bacteria; p_Firmicutes; c_Clostridia; o_Clostridiales; f_Lachnospiraceae | 3.50 | 1.10 | 2.00 |
| k_Bacteria; p_Firmicutes; c_Clostridia; o_Clostridiales; f_Peptostreptococcaceae | 0.00 | 0.00 | 0.80 |
| k_Bacteria; p_Firmicutes; c_Clostridia; o_Clostridiales; f_Ruminococcaceae | 6.98 | 3.55 | 3.40 |
| k_Bacteria; p_Firmicutes; c_Clostridia; o_Clostridiales; f_[Mogibacteriaceae] | 0.04 | 0.00 | 0.00 |
| k_Bacteria; p_Firmicutes; c_Erysipelotrichi; o_Erysipelotrichales; f_Erysipelotrichaceae | 0.00 | 0.05 | 0.00 |
| k_Bacteria; p_Proteobacteria; c_Betaproteobacteria; o_Burkholderiales; f_Alcaligenaceae | 0.32 | 1.60 | 0.90 |
| k_Bacteria; p_Proteobacteria; c_Deltaproteobacteria; o_Desulfovibrionales; f_Desulfovibrionaceae | 0.65 | 0.35 | 3.40 |
| k_Bacteria; p_Proteobacteria; c_Epsilonproteobacteria; o_Campylobacterales; f_Helicobacteraceae | 1.72 | 0.75 | 0.00 |
| k_Bacteria; p_TM7; c_TM7-3; o_CW040; f_F16 | 0.17 | 0.15 | 0.00 |
| k_Bacteria; p_Tenericutes; c_Mollicutes; o_Mycoplasmatales; f_Mycoplasmataceae | 0.00 | 0.05 | 0.00 |

* Each group was pooled from five independent samples

What is claimed is:

1. A method for modulating gut microbiota, the method comprising administering to a subject an effective amount of a composition comprising a first edible plant-derived nanoparticle encapsulating an effective amount of an miRNA selected from the group consisting of miR166c, miRNA167a, miR319a, miR396e, miR842, and miR827, optionally wherein the miRNA is obtained from a second edible-plant derived nanoparticle, wherein the effective amount results in a change in the makeup of the subject's gut microbiota relative to that present prior to the administering step.

2. The method of claim 1, wherein the first edible plant-derived nanoparticle, the second edible plant-derived nanoparticle, or both are derived from an edible plant selected from the group consisting of ginger, grapefruit, carrot, garlic, and turmeric.

3. The method of claim 2, wherein the edible plant is ginger.

4. The method of claim 1, wherein the gut microbiota that is modulated is a Lactobacillaceae, a Bacteroidaceae, a Clostridiaceae, a Ruminococcaceae, or any combination thereof.

5. The method of claim 4, wherein the modulating comprises increasing numbers of Lactobacillaceae and/or Bacteroidaceae, decreasing numbers of Clostridiaceae and/or Ruminococcaceae, or both in the gut microbiota of the subject.

* * * * *

SEQUENCE LISTING

<160> NUMBER OF SEQ ID NOS: 164

<210> SEQ ID NO 1
<211> LENGTH: 32
<212> TYPE: DNA
<213> ORGANISM: Artificial Sequence
<220> FEATURE:
<223> OTHER INFORMATION: Artificially synthesized oligonucleotide

<400> SEQUENCE: 1
gcgcatgcct gcaactaatt ttgtcgcaaa cg        32

<210> SEQ ID NO 2
<211> LENGTH: 28
<212> TYPE: DNA
<213> ORGANISM: Artificial Sequence

```
<220> FEATURE:
<223> OTHER INFORMATION: Artificially synthesized oligonucleotide

<400> SEQUENCE: 2
cctctagaac agttttcagc aggcatcc                                          28

<210> SEQ ID NO 3
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 3
ctgtaggtgc tgtaactgcc tgaataccgt aatac                                  35

<210> SEQ ID NO 4
<211> LENGTH: 35
<212> TYPE: DNA
<213> ORGANISM: Artificial Sequence
<220> FEATURE:
<223> OTHER INFORMATION: Artificially synthesized oligonucleotide

<400> SEQUENCE: 4
gtattacggt attcaggcag ttacagcacc tacag                                  35

<210> SEQ ID NO 5
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 5
agagtttgat cctggctcag                                                   20

<210> SEQ ID NO 6
<211> LENGTH: 17
<212> TYPE: DNA
<213> ORGANISM: Artificial Sequence
<220> FEATURE:
<223> OTHER INFORMATION: Artificially synthesized oligonucleotide

<400> SEQUENCE: 6
attaccgcgg ctgctgg                                                      17

<210> SEQ ID NO 7
<211> LENGTH: 30
<212> TYPE: DNA
<213> ORGANISM: Artificial Sequence
<220> FEATURE:
<223> OTHER INFORMATION: Artificially synthesized oligonucleotide

<400> SEQUENCE: 7
ccatctcatc cctgcgtgtc tccgactcag                                        30

<210> SEQ ID NO 8
<211> LENGTH: 30
<212> TYPE: DNA
<213> ORGANISM: Artificial Sequence
<220> FEATURE:
<223> OTHER INFORMATION: Artificially synthesized oligonucleotide

<400> SEQUENCE: 8
cctatcccct gtgtgccttg gcagtctcag                                        30
```

```
<210> SEQ ID NO 9
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 9
ugaagcugcc agcaugaucu a                                              21

<210> SEQ ID NO 10
<211> LENGTH: 18
<212> TYPE: DNA
<213> ORGANISM: Artificial Sequence
<220> FEATURE:
<223> OTHER INFORMATION: Artificially synthesized oligonucleotide

<400> SEQUENCE: 10
tcggcctcgt ggatggac                                                  18

<210> SEQ ID NO 11
<211> LENGTH: 18
<212> TYPE: DNA
<213> ORGANISM: Artificial Sequence
<220> FEATURE:
<223> OTHER INFORMATION: Artificially synthesized oligonucleotide

<400> SEQUENCE: 11
tcggcctcgt ggatggac                                                  18

<210> SEQ ID NO 12
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 12
tttcggtagt taactgctga gg                                             22

<210> SEQ ID NO 13
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 13
tttccgactc gcactcatgc                                                20

<210> SEQ ID NO 14
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 14
tcatggtcag atccgtcatc                                                20

<210> SEQ ID NO 15
<211> LENGTH: 21
<212> TYPE: DNA
<213> ORGANISM: Artificial Sequence
<220> FEATURE:
<223> OTHER INFORMATION: Artificially synthesized oligonucleotide
```

<400> SEQUENCE: 15
tgacattgta gatctacgtg c                                             21

<210> SEQ ID NO 16
<211> LENGTH: 19
<212> TYPE: DNA
<213> ORGANISM: Artificial Sequence
<220> FEATURE:
<223> OTHER INFORMATION: Artificially synthesized oligonucleotide

<400> SEQUENCE: 16
ctcagcagtc gactgtacc                                                19

<210> SEQ ID NO 17
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 17
aatcgttgag gctgaagtcg t                                             21

<210> SEQ ID NO 18
<211> LENGTH: 19
<212> TYPE: DNA
<213> ORGANISM: Artificial Sequence
<220> FEATURE:
<223> OTHER INFORMATION: Artificially synthesized oligonucleotide

<400> SEQUENCE: 18
gaatgacgtc cggtctgaa                                                19

<210> SEQ ID NO 19
<211> LENGTH: 19
<212> TYPE: DNA
<213> ORGANISM: Artificial Sequence
<220> FEATURE:
<223> OTHER INFORMATION: Artificially synthesized oligonucleotide

<400> SEQUENCE: 19
tcattgctgg tgctcgttg                                                19

<210> SEQ ID NO 20
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 20
cgtgacgaac ataatcaaac g                                             21

<210> SEQ ID NO 21
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 21
ggagagtggt cggattgtag                                               20

<210> SEQ ID NO 22

<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 22
agtgctgcta gcaactacaa g                                              21

<210> SEQ ID NO 23
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 23
ggttagatga ccatcaacaa act                                            23

<210> SEQ ID NO 24
<211> LENGTH: 19
<212> TYPE: DNA
<213> ORGANISM: Artificial Sequence
<220> FEATURE:
<223> OTHER INFORMATION: Artificially synthesized oligonucleotide

<400> SEQUENCE: 24
catccagcca tccacccca                                                 19

<210> SEQ ID NO 25
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 25
caagcagtgg catcacataa c                                              21

<210> SEQ ID NO 26
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 26
cgccgaatag tccatacgaa ta                                             22

<210> SEQ ID NO 27
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 27
gtcctttgtg ccatggtatt g                                              21

<210> SEQ ID NO 28
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 28
tgcagcacct acaggttatc                                                   20

<210> SEQ ID NO 29
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 29
aggatgaggc aacggttaaa                                                   20

<210> SEQ ID NO 30
<211> LENGTH: 22
<212> TYPE: DNA
<213> ORGANISM: Artificial Sequence
<220> FEATURE:
<223> OTHER INFORMATION: Artificially synthesized oligonucleotide

<400> SEQUENCE: 30
cgtgacactt gggaagtaca ta                                                22

<210> SEQ ID NO 31
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 31
catgtggttt aattcgatga t                                                 21

<210> SEQ ID NO 32
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 32
agctgacgac aaccatgcag                                                   20

<210> SEQ ID NO 33
<211> LENGTH: 16
<212> TYPE: DNA
<213> ORGANISM: Artificial Sequence
<220> FEATURE:
<223> OTHER INFORMATION: Artificially synthesized oligonucleotide

<400> SEQUENCE: 33
gcacaagcag tggagt                                                       16

<210> SEQ ID NO 34
<211> LENGTH: 18
<212> TYPE: DNA
<213> ORGANISM: Artificial Sequence
<220> FEATURE:
<223> OTHER INFORMATION: Artificially synthesized oligonucleotide

<400> SEQUENCE: 34
cttcctccgt tttgtcaa                                                     18

<210> SEQ ID NO 35
<211> LENGTH: 22
<212> TYPE: DNA

```
<213> ORGANISM: Artificial Sequence
<220> FEATURE:
<223> OTHER INFORMATION: Artificially synthesized oligonucleotide

<400> SEQUENCE: 35
gcaggcctaa cacatgcaag tc                                              22

<210> SEQ ID NO 36
<211> LENGTH: 19
<212> TYPE: DNA
<213> ORGANISM: Artificial Sequence
<220> FEATURE:
<223> OTHER INFORMATION: Artificially synthesized oligonucleotide

<400> SEQUENCE: 36
tgctgcctcc cgtaggagt                                                  19

<210> SEQ ID NO 37
<211> LENGTH: 21
<212> TYPE: DNA
<213> ORGANISM: Artificial Sequence
<220> FEATURE:
<223> OTHER INFORMATION: Artificially synthesized oligonucleotide

<400> SEQUENCE: 37
gcagcagtag ggaatcttcc a                                               21

<210> SEQ ID NO 38
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 38
gcattycacc gctacacatg                                                 20

<210> SEQ ID NO 39
<211> LENGTH: 19
<212> TYPE: DNA
<213> ORGANISM: Artificial Sequence
<220> FEATURE:
<223> OTHER INFORMATION: Artificially synthesized oligonucleotide

<400> SEQUENCE: 39
atggctgtcg tcagctcgt                                                  19

<210> SEQ ID NO 40
<211> LENGTH: 23
<212> TYPE: DNA
<213> ORGANISM: Artificial Sequence
<220> FEATURE:
<223> OTHER INFORMATION: Artificially synthesized oligonucleotide

<400> SEQUENCE: 40
cctacttctt ttgcaaccca ctc                                             23

<210> SEQ ID NO 41
<211> LENGTH: 19
<212> TYPE: DNA
<213> ORGANISM: Artificial Sequence
<220> FEATURE:
<223> OTHER INFORMATION: Artificially synthesized oligonucleotide

<400> SEQUENCE: 41
caaccggtcc atgaaccgt                                                  19
```

```
<210> SEQ ID NO 42
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 42
tacggggact tgtacatcgt                                                   20

<210> SEQ ID NO 43
<211> LENGTH: 20
<212> TYPE: DNA
<213> ORGANISM: Artificial Sequence
<220> FEATURE:
<223> OTHER INFORMATION: Artificially synthesized oligonucleotide

<400> SEQUENCE: 43
actgagaggt tgaacggcca                                                   20

<210> SEQ ID NO 44
<211> LENGTH: 23
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (17)..(17)
<223> OTHER INFORMATION: w is a or t

<400> SEQUENCE: 44
cctttacacc cagtaawtcc gga                                               23

<210> SEQ ID NO 45
<211> LENGTH: 19
<212> TYPE: DNA
<213> ORGANISM: Artificial Sequence
<220> FEATURE:
<223> OTHER INFORMATION: Artificially synthesized oligonucleotide

<400> SEQUENCE: 45
ctcctacggg aggcagcag                                                    19

<210> SEQ ID NO 46
<211> LENGTH: 18
<212> TYPE: DNA
<213> ORGANISM: Artificial Sequence
<220> FEATURE:
<223> OTHER INFORMATION: Artificially synthesized oligonucleotide

<400> SEQUENCE: 46
gtattaccgc ggctgctg                                                     18

<210> SEQ ID NO 47
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 47
uugacagaag auagagagca c                                                 21

<210> SEQ ID NO 48
```

```
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 48
ugacagaaga uagagagcac                                                      20

<210> SEQ ID NO 49
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 49
uuuggauuga agggagcucu a                                                    21

<210> SEQ ID NO 50
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 50
ugccuggcuc ccuguaugcc a                                                    21

<210> SEQ ID NO 51
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 51
ucgauaaacc ucugcaucca g                                                    21

<210> SEQ ID NO 52
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 52
aaucguugag gcugaagucg u                                                    21

<210> SEQ ID NO 53
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 53
uggagaagca gggcacgugc a                                                    21

<210> SEQ ID NO 54
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 54
```

```
ucggaccagg cuucauuccc c                                              21

<210> SEQ ID NO 55
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 55
ggaauguugu cuggcucgag g                                              21

<210> SEQ ID NO 56
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 56
ugaagcugcc agcaugaucu a                                              21

<210> SEQ ID NO 57
<211> LENGTH: 22
<212> TYPE: RNA
<213> ORGANISM: Artificial Sequence
<220> FEATURE:
<223> OTHER INFORMATION: Artificially synthesized oligonucleotide

<400> SEQUENCE: 57
ugaagcugcc agcaugaucu gg                                             22

<210> SEQ ID NO 58
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 58
cccgccuugc aucaacugaa u                                              21

<210> SEQ ID NO 59
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 59
ucgcuuggug caggucggga a                                              21

<210> SEQ ID NO 60
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 60
uagccaagga ugacuugccu g                                              21

<210> SEQ ID NO 61
<211> LENGTH: 21
<212> TYPE: RNA
```

```
<213> ORGANISM: Artificial Sequence
<220> FEATURE:
<223> OTHER INFORMATION: Artificially synthesized oligonucleotide

<400> SEQUENCE: 61
ugauugagcc gcgccaauau c                                            21

<210> SEQ ID NO 62
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 62
uugagccgug ccaauaucac g                                            21

<210> SEQ ID NO 63
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 63
agaaucuuga ugaugcugca u                                            21

<210> SEQ ID NO 64
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 64
gaaucuugau gaugcugcau                                              20

<210> SEQ ID NO 65
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 65
uuggacugaa gggagcuccc u                                            21

<210> SEQ ID NO 66
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 66
cgugacgaac auaaucaaac g                                            21

<210> SEQ ID NO 67
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 67
aagcucagga gggauagcgc c                                            21
```

```
<210> SEQ ID NO 68
<211> LENGTH: 22
<212> TYPE: RNA
<213> ORGANISM: Artificial Sequence
<220> FEATURE:
<223> OTHER INFORMATION: Artificially synthesized oligonucleotide

<400> SEQUENCE: 68
uccaaaggga ucgcauugau cc                                            22

<210> SEQ ID NO 69
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 69
uuggcauucu guccaccucc                                               20

<210> SEQ ID NO 70
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 70
cugaaguguu uggggggaacu c                                            21

<210> SEQ ID NO 71
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 71
guucaauaaa gcuguggggaa g                                            21

<210> SEQ ID NO 72
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 72
uuccacagcu uucuugaacu g                                             21

<210> SEQ ID NO 73
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 73
uuccacagcu uucuugaacu u                                             21

<210> SEQ ID NO 74
<211> LENGTH: 21
<212> TYPE: RNA
<213> ORGANISM: Artificial Sequence
<220> FEATURE:
```

```
<223> OTHER INFORMATION: Artificially synthesized oligonucleotide

<400> SEQUENCE: 74
ucauugagug cagcguugau g                                              21

<210> SEQ ID NO 75
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 75
augcacugcc ucuucccugg c                                              21

<210> SEQ ID NO 76
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 76
ucgcucugau accaaaugau g                                              21

<210> SEQ ID NO 77
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 77
uuucguuguc uguucgaccu u                                              21

<210> SEQ ID NO 78
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 78
ugacagaaga gagagagcac                                                20

<210> SEQ ID NO 79
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 79
ggaaucuuga ugaugcugca u                                              21

<210> SEQ ID NO 80
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 80
augaugauga ugaugaugaa a                                              21
```

```
<210> SEQ ID NO 81
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 81
uuagaugacc aucaacaaac u                                              21

<210> SEQ ID NO 82
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 82
ucauggucag auccgucauc c                                              21

<210> SEQ ID NO 83
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 83
uucguugucu guucgaccuu g                                              21

<210> SEQ ID NO 84
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 84
ugacagaaga gagagagcac a                                              21

<210> SEQ ID NO 85
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 85
ugccuggcuc ccuguaugcc                                                20

<210> SEQ ID NO 86
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 86
cucggaccag gcuucauucc c                                              21

<210> SEQ ID NO 87
<211> LENGTH: 21
<212> TYPE: RNA
<213> ORGANISM: Artificial Sequence
<220> FEATURE:
<223> OTHER INFORMATION: Artificially synthesized oligonucleotide
```

```
<400> SEQUENCE: 87
ucucggacca ggcuucauuc c                                              21

<210> SEQ ID NO 88
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 88
uagccaagga ugacuugccu a                                              21

<210> SEQ ID NO 89
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 89
ugauugagcc gugccaauau c                                              21

<210> SEQ ID NO 90
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 90
ugagccgaac caauaucacc c                                              21

<210> SEQ ID NO 91
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 91
uccaaaggga ucgcauugau c                                              21

<210> SEQ ID NO 92
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 92
ugaaguguuu gggggaacuc                                                20

<210> SEQ ID NO 93
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 93
auugagugca gcguugauga a                                              21

<210> SEQ ID NO 94
<211> LENGTH: 21
```

```
<212> TYPE: RNA
<213> ORGANISM: Artificial Sequence
<220> FEATURE:
<223> OTHER INFORMATION: Artificially synthesized oligonucleotide

<400> SEQUENCE: 94
uguguucuca ggucgcccu g                                              21

<210> SEQ ID NO 95
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 95
uugcugccuc aagcuugcug c                                             21

<210> SEQ ID NO 96
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 96
agugcugcua gcaacuacaa g                                             21

<210> SEQ ID NO 97
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 97
ucauugcugg ugcucguugg a                                             21

<210> SEQ ID NO 98
<211> LENGTH: 23
<212> TYPE: RNA
<213> ORGANISM: Artificial Sequence
<220> FEATURE:
<223> OTHER INFORMATION: Artificially synthesized oligonucleotide

<400> SEQUENCE: 98
ggagaguggu cggauuguag cuc                                           23

<210> SEQ ID NO 99
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 99
aaccaggcuc ugauaccaug                                               20

<210> SEQ ID NO 100
<211> LENGTH: 18
<212> TYPE: RNA
<213> ORGANISM: Artificial Sequence
<220> FEATURE:
<223> OTHER INFORMATION: Artificially synthesized oligonucleotide

<400> SEQUENCE: 100
```

```
auuggaguga agggagcu                                                    18

<210> SEQ ID NO 101
<211> LENGTH: 22
<212> TYPE: RNA
<213> ORGANISM: Artificial Sequence
<220> FEATURE:
<223> OTHER INFORMATION: Artificially synthesized oligonucleotide

<400> SEQUENCE: 101
uugacagaag agagagagca ca                                               22

<210> SEQ ID NO 102
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 102
acagaagaua gagagcacag                                                  20

<210> SEQ ID NO 103
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 103
ucgauaaacc ucugcaucca                                                  20

<210> SEQ ID NO 104
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 104
uggagaagca gggcacgugc                                                  20

<210> SEQ ID NO 105
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 105
cggaccaggc uucauucccc                                                  20

<210> SEQ ID NO 106
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 106
ucggaccagg cuucauuccc                                                  20

<210> SEQ ID NO 107
<211> LENGTH: 20
<212> TYPE: RNA
<213> ORGANISM: Artificial Sequence
```

```
<220> FEATURE:
<223> OTHER INFORMATION: Artificially synthesized oligonucleotide

<400> SEQUENCE: 107
ucucggacca ggcuucauuc                                               20

<210> SEQ ID NO 108
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 108
ugaagcugcc agcaugaucu g                                             21

<210> SEQ ID NO 109
<211> LENGTH: 19
<212> TYPE: RNA
<213> ORGANISM: Artificial Sequence
<220> FEATURE:
<223> OTHER INFORMATION: Artificially synthesized oligonucleotide

<400> SEQUENCE: 109
ucgcuuggug caggucggg                                                19

<210> SEQ ID NO 110
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 110
uugagccgcg ccaauaucac u                                             21

<210> SEQ ID NO 111
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 111
ggaaucuuga ugaugcugca g                                             21

<210> SEQ ID NO 112
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 112
agaaucuuga ugaugcugca                                               20

<210> SEQ ID NO 113
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 113
ugaaucuuga ugaugcugca u                                             21
```

```
<210> SEQ ID NO 114
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 114
uuggacugaa gggagcuccc                                                    20

<210> SEQ ID NO 115
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 115
uuuuggacug aagggagcuc c                                                  21

<210> SEQ ID NO 116
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 116
agcucaggag ggauagcgcc                                                    20

<210> SEQ ID NO 117
<211> LENGTH: 22
<212> TYPE: RNA
<213> ORGANISM: Artificial Sequence
<220> FEATURE:
<223> OTHER INFORMATION: Artificially synthesized oligonucleotide

<400> SEQUENCE: 117
uuccaaaggg aucgcauuga uc                                                 22

<210> SEQ ID NO 118
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 118
uucaauaaag cugugggaag                                                    20

<210> SEQ ID NO 119
<211> LENGTH: 22
<212> TYPE: RNA
<213> ORGANISM: Artificial Sequence
<220> FEATURE:
<223> OTHER INFORMATION: Artificially synthesized oligonucleotide

<400> SEQUENCE: 119
uuccacagcu uucuugaacu gu                                                 22

<210> SEQ ID NO 120
<211> LENGTH: 20
<212> TYPE: RNA
<213> ORGANISM: Artificial Sequence
<220> FEATURE:
<223> OTHER INFORMATION: Artificially synthesized oligonucleotide
```

```
<400> SEQUENCE: 120
uccacagcuu ucuugaacug                                           20

<210> SEQ ID NO 121
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 121
ugcacugccu cuucccuggc                                           20

<210> SEQ ID NO 122
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 122
aggcaguggc uugguuaagg g                                         21

<210> SEQ ID NO 123
<211> LENGTH: 19
<212> TYPE: RNA
<213> ORGANISM: Artificial Sequence
<220> FEATURE:
<223> OTHER INFORMATION: Artificially synthesized oligonucleotide

<400> SEQUENCE: 123
ggacagucuc agguagaca                                            19

<210> SEQ ID NO 124
<211> LENGTH: 18
<212> TYPE: RNA
<213> ORGANISM: Artificial Sequence
<220> FEATURE:
<223> OTHER INFORMATION: Artificially synthesized oligonucleotide

<400> SEQUENCE: 124
gucguuguag uauagugg                                             18

<210> SEQ ID NO 125
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 125
uugacagaag agagagagca c                                         21

<210> SEQ ID NO 126
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 126
uugagccgcg ucaauaucuc c                                         21

<210> SEQ ID NO 127
```

```
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 127
uugagugcag cguugaugaa a                                               21

<210> SEQ ID NO 128
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 128
ugacaacgag agagagcacg c                                               21

<210> SEQ ID NO 129
<211> LENGTH: 26
<212> TYPE: RNA
<213> ORGANISM: Artificial Sequence
<220> FEATURE:
<223> OTHER INFORMATION: Artificially synthesized oligonucleotide

<400> SEQUENCE: 129
cauccagcca uccaccccag gccauc                                          26

<210> SEQ ID NO 130
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 130
ucggaccagg cuucauuccu c                                               21

<210> SEQ ID NO 131
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 131
ggaauguugg cuggcucgag g                                               21

<210> SEQ ID NO 132
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 132
ugauugagcc gcgucaauau c                                               21

<210> SEQ ID NO 133
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 133
```
agauugagcc gcgccaauau c                                              21

<210> SEQ ID NO 134
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 134
agagcuuccu ucaguccacu c                                              21

<210> SEQ ID NO 135
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 135
uuggacugaa gggagcuccc a                                              21

<210> SEQ ID NO 136
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 136
gaaugacguc cggucugaag a                                              21

<210> SEQ ID NO 137
<211> LENGTH: 22
<212> TYPE: RNA
<213> ORGANISM: Artificial Sequence
<220> FEATURE:
<223> OTHER INFORMATION: Artificially synthesized oligonucleotide

<400> SEQUENCE: 137
cucagcaguc gacuguaccg ug                                             22

<210> SEQ ID NO 138
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 138
guucaauaaa gcugugggaa                                                20

<210> SEQ ID NO 139
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 139
uccacaggcu uucuugaacg g                                              21

<210> SEQ ID NO 140
<211> LENGTH: 22
<212> TYPE: RNA

```
<213> ORGANISM: Artificial Sequence
<220> FEATURE:
<223> OTHER INFORMATION: Artificially synthesized oligonucleotide

<400> SEQUENCE: 140
ugaggaggaa cauauuuacu ag                                              22

<210> SEQ ID NO 141
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 141
ucggccucgu ggauggacca g                                               21

<210> SEQ ID NO 142
<211> LENGTH: 22
<212> TYPE: RNA
<213> ORGANISM: Artificial Sequence
<220> FEATURE:
<223> OTHER INFORMATION: Artificially synthesized oligonucleotide

<400> SEQUENCE: 142
uagccaagga ugacuugccu gc                                              22

<210> SEQ ID NO 143
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 143
cauccaaagg gaucgcauug a                                               21

<210> SEQ ID NO 144
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 144
ugacauugua gaucuacgug c                                               21

<210> SEQ ID NO 145
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 145
cuuggacuga agggagcucc                                                 20

<210> SEQ ID NO 146
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 146
cuuggacuga agggagcucc c                                               21
```

-continued

```
<210> SEQ ID NO 147
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 147
ugcacugccu cuucccuggc u                                              21

<210> SEQ ID NO 148
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 148
cucucccuca aaggcuucca                                                20

<210> SEQ ID NO 149
<211> LENGTH: 19
<212> TYPE: RNA
<213> ORGANISM: Artificial Sequence
<220> FEATURE:
<223> OTHER INFORMATION: Artificially synthesized oligonucleotide

<400> SEQUENCE: 149
ucucccucaa aggcuucca                                                 19

<210> SEQ ID NO 150
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 150
ugacagaaga gagggagcac                                                20

<210> SEQ ID NO 151
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 151
uuggacugaa gggagcuccu                                                20

<210> SEQ ID NO 152
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 152
uuccacggcu uucuugaacu u                                              21

<210> SEQ ID NO 153
<211> LENGTH: 20
<212> TYPE: RNA
<213> ORGANISM: Artificial Sequence
<220> FEATURE:
```

<223> OTHER INFORMATION: Artificially synthesized oligonucleotide

<400> SEQUENCE: 153
ucggaccagg cuucauuccu					20

<210> SEQ ID NO 154
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 154
uagccaagga ugacuugccu					20

<210> SEQ ID NO 155
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 155
ggaaucuuga ugaugcugca					20

<210> SEQ ID NO 156
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 156
cugacagaag agagugagca					20

<210> SEQ ID NO 157
<211> LENGTH: 19
<212> TYPE: RNA
<213> ORGANISM: Artificial Sequence
<220> FEATURE:
<223> OTHER INFORMATION: Artificially synthesized oligonucleotide

<400> SEQUENCE: 157
agaaucuuga ugaugcugc					19

<210> SEQ ID NO 158
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 158
ucggaccagg cuucauuccc c					21

<210> SEQ ID NO 159
<211> LENGTH: 23
<212> TYPE: RNA
<213> ORGANISM: Artificial Sequence
<220> FEATURE:
<223> OTHER INFORMATION: Artificially synthesized oligonucleotide

<400> SEQUENCE: 159
uuuccgacuc gcacucaugc cgu					23

```
<210> SEQ ID NO 160
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 160
ugauugagcc gcgccaauau                                                  20

<210> SEQ ID NO 161
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 161
uugagccgug ccaauaucac                                                  20

<210> SEQ ID NO 162
<211> LENGTH: 21
<212> TYPE: RNA
<213> ORGANISM: Artificial Sequence
<220> FEATURE:
<223> OTHER INFORMATION: Artificially synthesized oligonucleotide

<400> SEQUENCE: 162
guucaagaaa gcuguggaag a                                                21

<210> SEQ ID NO 163
<211> LENGTH: 22
<212> TYPE: RNA
<213> ORGANISM: Artificial Sequence
<220> FEATURE:
<223> OTHER INFORMATION: Artificially synthesized oligonucleotide

<400> SEQUENCE: 163
uuucgguagu uaacugcuga gg                                               22

<210> SEQ ID NO 164
<211> LENGTH: 20
<212> TYPE: RNA
<213> ORGANISM: Artificial Sequence
<220> FEATURE:
<223> OTHER INFORMATION: Artificially synthesized oligonucleotide

<400> SEQUENCE: 164
ugacagaaga gagugagcac                                                  20
```